(12) United States Patent
Scilimati et al.

(10) Patent No.: US 12,011,433 B2
(45) Date of Patent: Jun. 18, 2024

(54) MOFEZOLAC DERIVATIVES AS MULTI-FUNCTIONS SELECTIVE COX-1 INHIBITORS

(71) Applicants: UNIVERSITÁ DEGLI STUDI DI BARI "ALDO MORO", Bari BA (IT); ITEL Telecomunicazioni S.r.l., Ruvo di Puglia BA (IT)

(72) Inventors: Antonio Scilimati, Bari BA (IT); Maria Grazia Perrone, Bari BA (IT); Paola Vitale, Bari BA (IT)

(73) Assignee: ITEL Telecomunicazioni S.r.l., Ruvo di Puglia BA (IT)

( * ) Notice: Subject to any disclaimer, the term of this patent is extended or adjusted under 35 U.S.C. 154(b) by 895 days.

(21) Appl. No.: 17/062,269

(22) Filed: Oct. 2, 2020

(65) Prior Publication Data
US 2021/0023055 A1 Jan. 28, 2021

Related U.S. Application Data

(63) Continuation of application No. 16/097,126, filed as application No. PCT/IB2017/052395 on Apr. 26, 2017, now abandoned.

(60) Provisional application No. 62/328,604, filed on Apr. 27, 2016.

(51) Int. Cl.
| | | |
|---|---|---|
| A61K 31/415 | (2006.01) |
| A61K 31/7024 | (2006.01) |
| A61P 37/06 | (2006.01) |
| C07D 261/08 | (2006.01) |
| C07D 413/12 | (2006.01) |
| C07D 413/14 | (2006.01) |
| C07H 13/04 | (2006.01) |

(52) U.S. Cl.
CPC ........ *A61K 31/415* (2013.01); *A61K 31/7024* (2013.01); *A61P 37/06* (2018.01); *C07D 261/08* (2013.01); *C07D 413/12* (2013.01); *C07D 413/14* (2013.01); *C07H 13/04* (2013.01)

(58) Field of Classification Search
None
See application file for complete search history.

(56) References Cited

U.S. PATENT DOCUMENTS

| | | | | |
|---|---|---|---|---|
| 5,399,577 A | * | 3/1995 | Shindo | C07F 9/653 514/378 |
| 2003/0220266 A1 | * | 11/2003 | Sales | A61K 45/06 514/420 |
| 2008/0138282 A1 | * | 6/2008 | Mann | A61K 51/0455 424/1.89 |

FOREIGN PATENT DOCUMENTS

JP H02223568 A * 9/1990 ............. A61K 31/42

* cited by examiner

*Primary Examiner* — Dale R Miller
(74) *Attorney, Agent, or Firm* — ArentFox Schiff LLP

(57) ABSTRACT

The invention relates to a new class of compounds targeting COX-1. The invention also relates to the use of some of such compounds as a tool to investigate the structure and function of the enzyme, in the treatment targeting COX-1 or detection of COX-1 in relating disorders or diseases such as cancer and neuroinflammation, in particular in neurological (e.g. autism spectrum disorders) and neurodegenerative diseases (e.g. Alzheimer's diseases, Parkinson's diseases, amyotrophic lateral sclerosis (ALS), multiple sclerosis (MS), traumatic brain injury (TBI), HIV dementia and prion diseases), and in gynecological tumor (e.g. ovarian cancer), neck and head tumor, and haematological tumors (e.g. multiple myeloma) and in the detection of COX-1 in "in vitro" (cells and tissues) and in "in vivo".

12 Claims, 12 Drawing Sheets

MOFEZOLAC DERIVATIVES AS MULTI-FUNCTIONS SELECTIVE COX-1 INHIBITORS

CROSS-REFERENCE TO RELATED APPLICATION

This application is a continuation of U.S. patent application Ser. No. 16/097,126 filed Oct. 26, 2018, which is a 35 U.S.C. § 371 National Phase Application of PCT Application No. PCT/IB2017/052395 filed Apr. 26, 2017, which claims priority to U.S. Application No. 62/328,604 filed Apr. 27, 2016. The disclosure of these prior applications are hereby incorporated by reference herein in their entirety.

DESCRIPTION

Technical Field of the Invention

The invention relates to a new class of compounds targeting COX-1. The invention also relates to the use of some of such compounds as a tool to investigate the structure and function of the enzyme, in the treatment targeting COX-1 or detection of COX-1 in relating disorders or diseases such as cancer and neuroinflammation (i.e. the inflammation of the nervous tissue), in particular in neurological (e.g. autism spectrum disorders) and neurodegenerative diseases (e.g. Alzheimer's diseases, Parkinson's diseases, amyotrophic lateral sclerosis (ALS), multiple sclerosis (MS), traumatic brain injury (TBI), HIV dementia and prion diseases), and in gynecological tumour (e.g. ovarian cancer), neck and head tumor, and haematological tumours (e.g. multiple myeloma) and in the detection of COX-1 in "in vitro" (cells and tissues) and in "in vivo".

BACKGROUND OF THE INVENTION

Cyclooxygenases (COXs), known as two isoforms COX-1 and COX-2, are the key enzymes in the conversion of arachidonic acid into prostaglandins and thromboxane. Arachidonic acid (AA) is released from the cell membrane also upon inflammatory and mitogen stimuli. Inflammation is a common phase of many diseases.

COX-1 plays a previously unrecognized role in the neuroinflammation. Genetic ablation or pharmacological inhibition of COX-1 catalytic activity attenuates the inflammatory response and neuronal loss. In this context, the treatment of LPS-stimulated microglial cell (a worldwide accepted neuroinflammation model) by selective COX-1 inhibitors (P6, P10, SC-560, aspirin) and coxibs (celecoxib and etoricoxib) determines the total suppression of the expression of either COX-1 or COX-2 by their respective selective inhibitors; NF-kB remained almost completely inactive in the presence of coxibs, as expected, and totally inactive in the presence of P6; P6 also markedly counteracted LPS enhancing cPGES mRNA expression and $PGE_2$ production. Then, since COX-1 is predominantly localized in microglia, its highly selective inhibition, rather than COX-2 (by coxibs), is more likely to reduce neuroinflammation and hence should be considered as a potential therapeutic approach to treat neuroinflammation and pharmacologically prevent neurological (e.g. autism spectrum disorders) and neurodegenerative diseases (e.g. Alzheimer's diseases, Parkinson's diseases, amyotrophic lateral sclerosis (ALS), multiple sclerosis (MS), traumatic brain injury (TBI), HIV dementia and prion diseases) with a marked inflammatory component [Scilimati et al. *Pharmacol. Res.* 65 (2012) 137-148]. Up to now, among the traditional non-steroidal anti-inflammatory drugs (tNSAIDs), only few examples of selective COX-1 inhibitors have been identified.

Thus, there remains a need in the art for potent COX-1 specific inhibitors that are effective in the treatment or detection of COX-1 relating disorders or diseases such as cancer and neuroinflammation.

Early diagnosis of ovarian cancer is nowadays a challenge to increase the patient 5-year survival rate for this malignancy. Despite the introduction of intensive surgical treatments and advances in the use of novel therapeutic agents, new diagnostic biomarkers are welcome as an attempt to reduce the morbidity and mortality caused from advanced stage of ovarian cancer. Most epithelial ovarian cancer cells express high levels of COX-1, rather than COX-2. Therefore, COX-1 has been recently proposed as an ideal biomarker for the ovarian cancer detection. COX-1 protein is moderately to highly express in 99% of high-grade tumours and COX-1 expression is significantly higher than COX-2 in high-grade tumours, and across all serous tumours compared to endometrioid, mucinous, and clear cell tumours. Moreover, the downregulation of COX-1 gene expression inhibits multiple protumorigenic pathways and knockdown of COX-1 inhibits protumorigenic functions such as cell viability, clonogenicity, and migration/invasion in COX-1 expressing ovarian cancer cells. All these data support the idea of COX-1 as an ovarian cancer biomarker.

Another noteworthy use of some of the new compounds is that being constituted by two COX-inhibitory moieties bond by a linker of different length or constituted by an COX-inhibitory portion and the COX-substrate are tools to investigated COX structure and function. The inhibitory portion is mofezolac, a known highly selective COX-1 inhibitor, and the arachidonic acid is the substrate part of these compounds. Such an investigation is needed because the chemical features of a compound that make it a selective COX-1 inhibitor are not yet definitively identified. Almost fifty amino acids of the COX catalytic site are involved in the inhibitor/substrate recognition. Known structure-activity relationship (SAR)investigations do not provide yet indications to project a highly selective COX-1 inhibitor.

SUMMARY OF THE INVENTION

The present invention relates to new compounds endowed with high affinity and selectivity for COX-1 as well as good pharmacokinetic properties. The present invention relates also to new compounds targeting the COX-1 and able to cross the blood-brain barrier and hence useful to treat the neuroinflammation. The present invention relates also to compounds capable to detect the COX presence in cells and tissues (healthy, representative of diseases, inflammed and tumours) and compounds to be used as tools to study the COX structure and function.

Hence, object of the present invention is a family of compounds having the general formula as indicated in claim 1.

A second object of the invention is mofezolac (R-G=OH) or its methyl ester for use in the treatment of inflammation in neurological (e.g. autism spectrum disorders) or neurodegenerative diseases (e.g. Alzheimer's diseases, Parkinson's diseases, amyotrophic lateral sclerosis (ALS), multiple sclerosis (MS), traumatic brain injury (TBI), HIV dementia and prion diseases).

A third object of the invention are compounds selected from the above-indicated families for use as medicaments, advantageously for use in the treatment of any condition susceptible of being improved or prevented by selective inhibition of COX-1. In particular, in the treatment of COX-1 relating disorders such as cancer more in particular in gynecological tumour (e.g. ovarian cancer), neck and head tumor, and haematological tumours (e.g. multiple myeloma), and in the treatment of inflammation in neurological (e.g. autism spectrum disorders) or neurodegenerative diseases (e.g. Alzheimer's diseases, Parkinson's diseases, amyotrophic lateral sclerosis (ALS), multiple sclerosis (MS), traumatic brain injury (TBI), HIV dementia and prion diseases).

A fourth object of the invention is the use of compounds selected from the above-indicated families for detecting and treating neuroinflammation targeting COX-1 and, hence, neurological and neurodegenerative diseases, because such selected compounds are able to cross the blood-brain barrier (through GLUT carriers) and then reach the central nervous system.

A fifth object of the invention is the use of compounds selected from the above-indicated families for detecting in vitro, ex-vivo or in vivo the presence of COX-1 in cells and tissues.

A sixth object of the invention is the use of compounds selected from the above-indicated families to investigate COX-1 structure and function.

A seventh object of the invention are the compounds herein disclosed isotopically radiolabeled.

A further object of the invention is a pharmaceutical composition comprising the compounds of the invention and a pharmacologically acceptable excipient.

Other objects will be made evident in the light of the following detailed description.

DETAILED DESCRIPTION OF THE INVENTION

Compounds of the Invention

Figure 1:
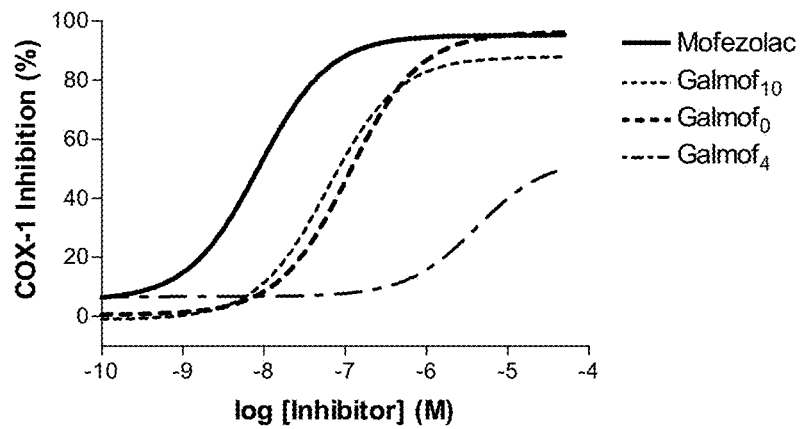
FIG. 1. Concentration-response curves of mofezolac and $GALMOF_n$ COX-1 inhibitory activity (n=0, 4, 10).

The invention relates to a family of novel compounds having the following general formula I thereof:

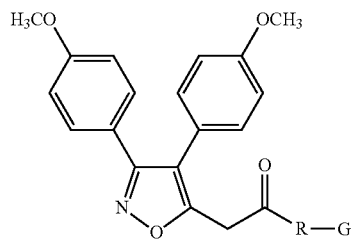

wherein
R-G is OH or OCH$_3$; or
R is a linker selected from benzidine, phenylenediamine, α,α'-diamino-p-xylene, alkyldiamine, O—(CH$_2$)$_n$ or NH—(CH$_2$)$_n$, NH—(CH$_2$)$_n$CO or NH—(CH$_2$)$_n$NH wherein n is from 0 to 12 and
G is selected from the group consisting of a sugar, an amino acid, a fluorescent moiety, mofezolac or arachidonic acid, hydrogen, OH, OCH$_3$, According to one embodiment the compound having the following formula I wherein G is selected from: galactose, glucose, fructose, glycine, valine, isoleucine, alanine, arginine, leucine, asparagine, lysine, histidine, aspartic acid, methionine, cysteine, phenylalanine, glutamic acid, threonine, glutamine, tryptophan, proline, selenocysteine, serine, tyrosine, mofezolac or arachidonic acid, nile blue or 6-(7-nitrobenzenfurazan-4-ylamino)hexanoic acid (NBD-C$_6$ acid) or 6-(7-nitrobenzenfurazan-4-ylamino)dodecanoic acid (NBD-C$_{12}$ acid) or rhodamine.

According to one embodiment the compound having the formula (I) reported above wherein R-G is OH or OCH$_3$ that correspond to mofezolac or its methyl ester for use in the treatment of neuroinflammation, in particular for use in the treatment of neurological (e.g. autism spectrum disorders) and/or neurodegenerative diseases (e.g. Alzheimer's diseases, Parkinson's diseases, amyotrophic lateral sclerosis (ALS), multiple sclerosis (MS), traumatic brain injury (TBI), HIV dementia and prion diseases).

According to one embodiment the compound having the following formula I wherein mofezolac is directly linked to the galactose through an ester bond.

According to one embodiment the compound having the following formula I wherein R is the NH—(CH$_2$)$_n$CO and n is from 4 to 10 and G is the galactose.

According to one embodiment the compound having the following formula I wherein mofezolac is directly linked to the glycine or glycine methyl ester through an amide bond.

According to one embodiment the compound having the following formula I wherein R is the NH—(CH$_2$)$_n$CO wherein n is from 0 to 10 and G is selected from OH, OCH$_3$, glycine or glycine methyl ester.

According to one embodiment the compound having the following formula I wherein R is the NH—(CH$_2$)$_n$NH wherein n is 2, 4, 6 or 12 and G is selected from a hydrogen, glycine, mofezolac, arachidonic acid, rhodamine or nile blue.

In one embodiment the mofezolac moiety [3,4-bis(4-methoxyphenyl)isoxazole] in the compounds with formula (I) can be replaced by P6-COOH 2-[3-(5-chlorofuran-2-yl)-4-phenylisoxazol-5-yl]acetic acid, a derivative of P6 [5-chlorofuran-2-yl)-3-phenylisoxazole] and, R is HN(CH$_2$)$_4$ NH and G is rhodamine.

According to one embodiment the compound having the following formula I wherein R is benzidine and G is selected from a hydrogen, mofezolac, arachidonic acid, NBD-C$_6$ or NBD-C$_{12}$.

According to one embodiment the compound having the following formula I wherein R is phenylenediamine and G is selected from a hydrogen, mofezolac, arachidonic acid.

According to one embodiment the compound having the following formula I wherein R is α,α'-diamino-p-xylene and G is selected from a hydrogen or mofezolac.

Specific examples of compounds of the invention are:

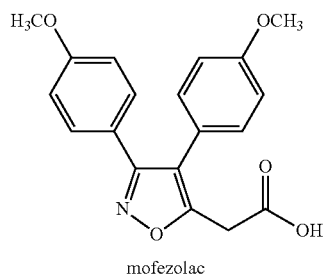

mofezolac

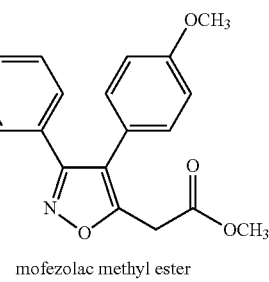

mofezolac methyl ester

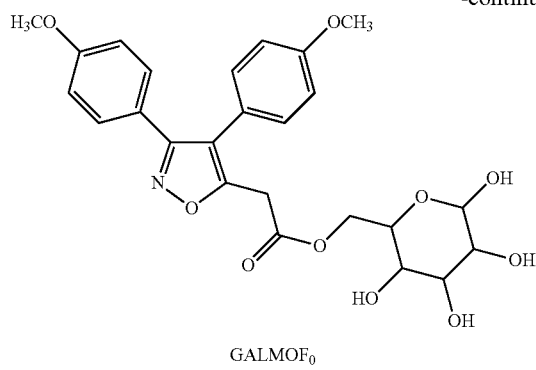
GALMOF₀
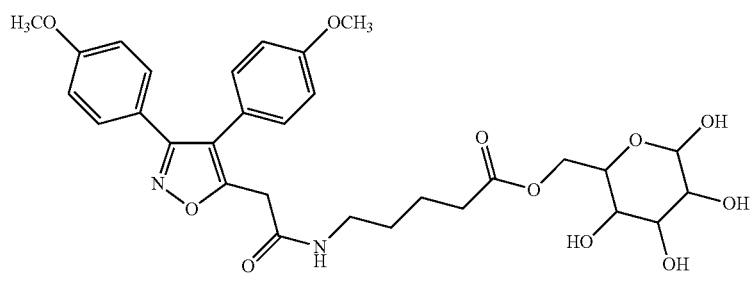
GALMOF₅
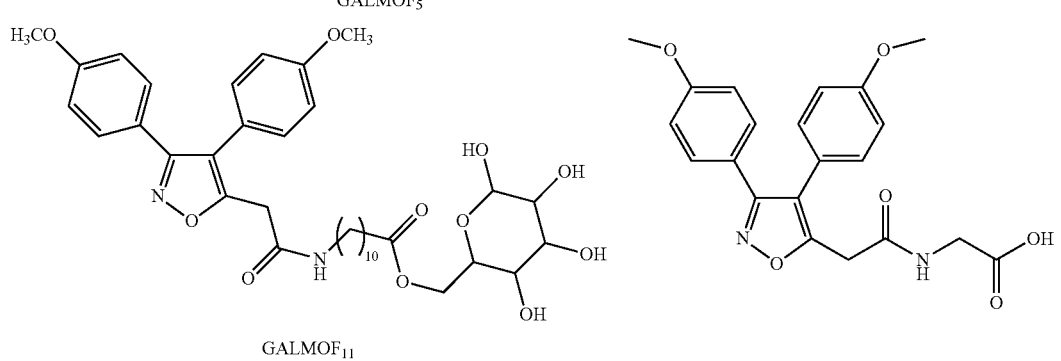
GALMOF₁₁
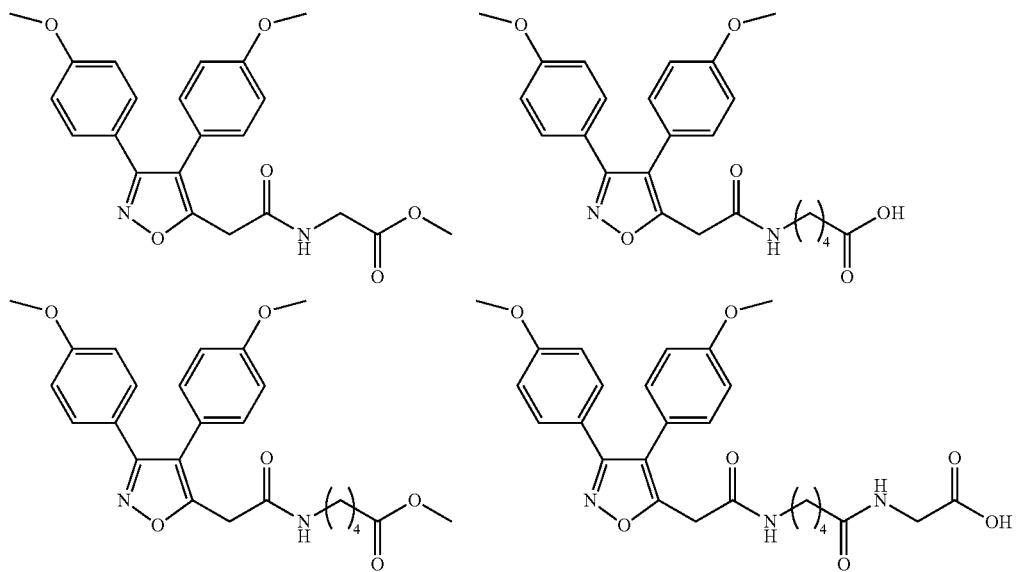

-continued
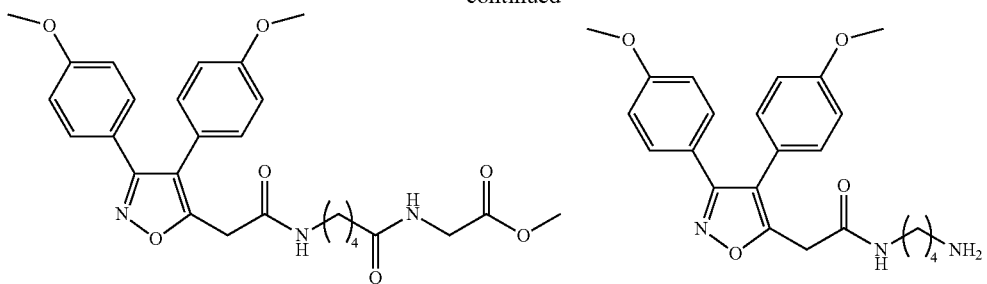
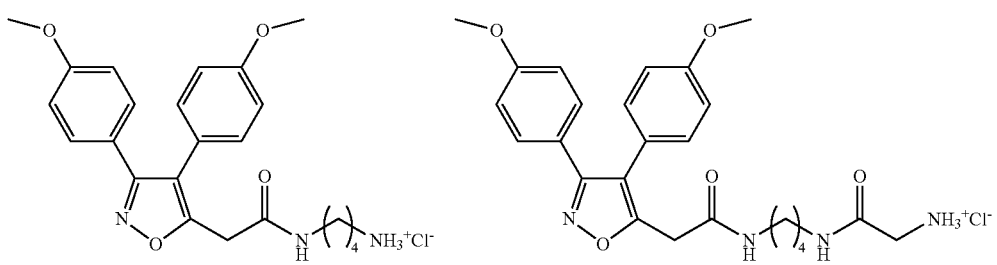
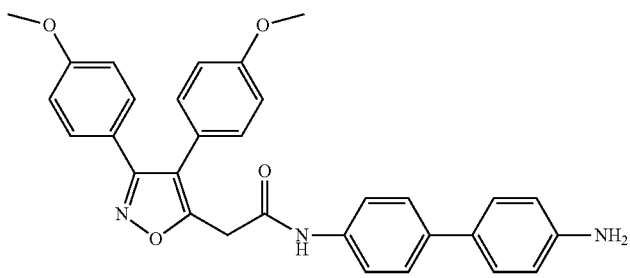
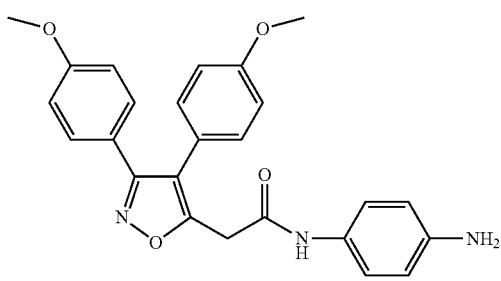
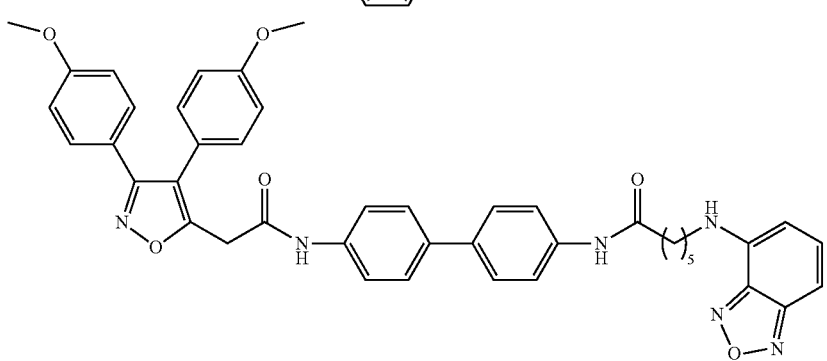

-continued
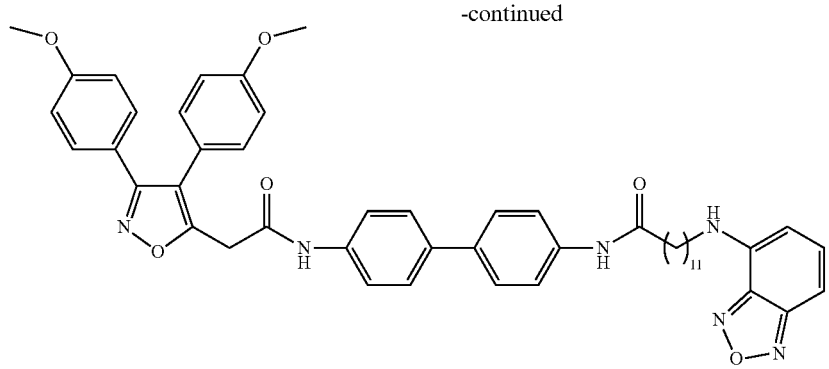
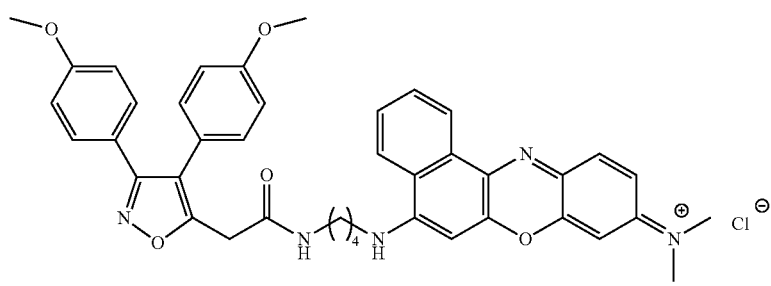
Mof-C4-Nile blue
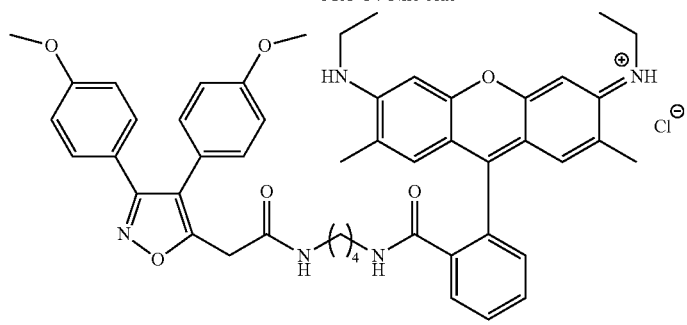
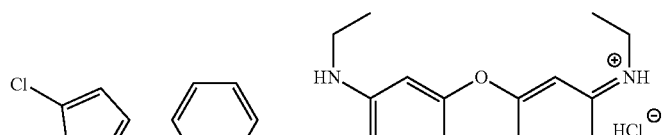
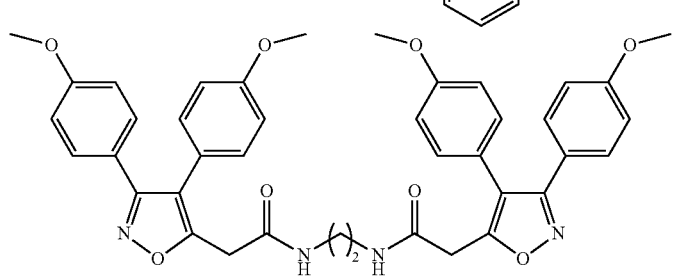

-continued
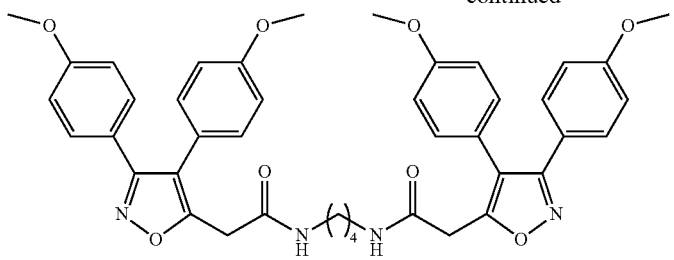
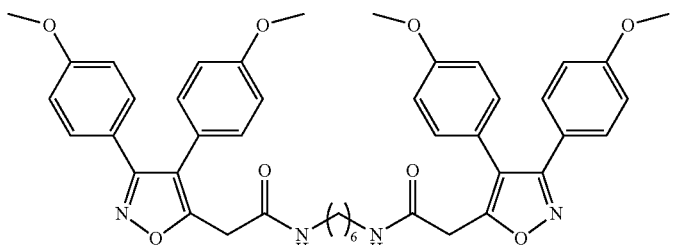
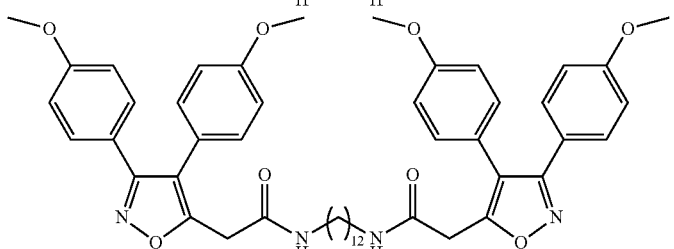
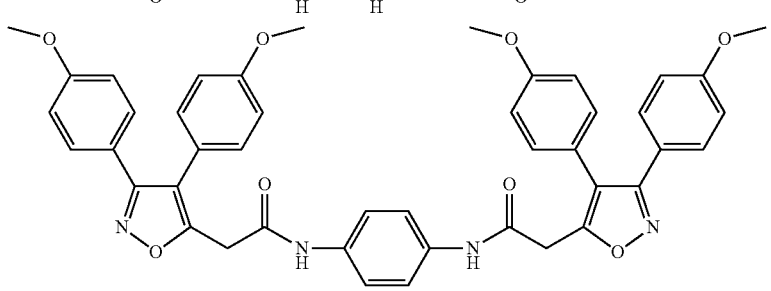
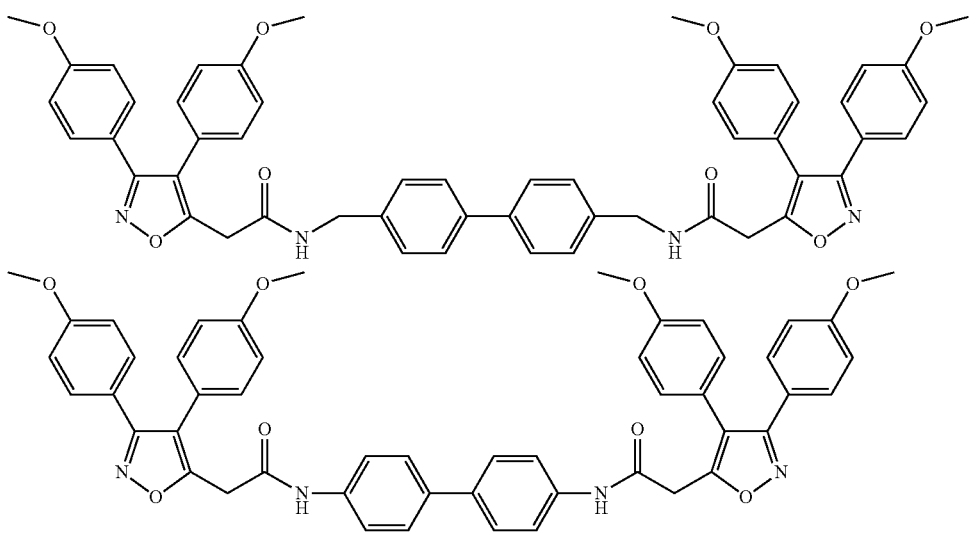

-continued

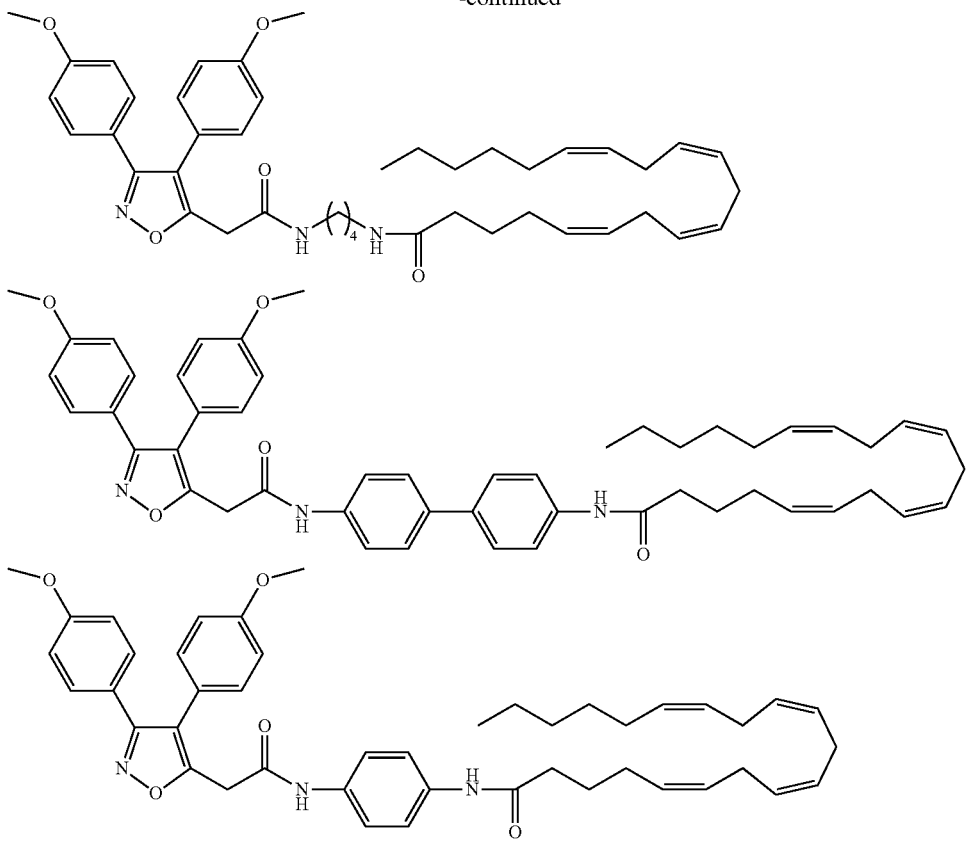

Compounds of the Invention Targeting COX-1 in the Central Nervous System (CNS)

More in details the compounds of the present invention are useful in the treatment of inflammatory processes that are tightly connected to the brain degenerative processes. Neuroinflammation is the primary step in the progression of several neurodegenerative disorders such as Alzheimer disease, Parkinson disease, amyotrophic lateral sclerosis, multiple sclerosis, traumatic brain injury, and HIV encephalitis, and in mental diseases such as the autism spectrum disorders.

Cyclooxygenase (COX)-1 exerts an important role in the neuroinflammatory process being constitutively expressed in microglia which in turn is activated by central nervous system (CNS) injuries. Microglial COX-1 rapidly responses to these inciting stimuli by producing the pro-inflammatory prostaglandin, such as the $PGE_2$. Thus, a selective COX-1 inhibition is expected to be useful in treating early stage of neuroinflammation.

The blood-brain barrier (BBB) crossing by drugs is one of the challenge of all scientists which target central nervous system diseases. The low permeability of BBB is the major impediment for drugs targeting CNS. Some of the compounds of the present invention are capable to "carry" the entire molecule into the CNS by the GLUT-1 carrier, which is located on the membrane of vascular endothelial cells. GLUT-1 belongs to the family of homologous proteins GLUTs (GLUT-1-5 that differ in their tissue distribution and affinity for hexoses). GLUT-1 is present in erythrocyte, BBB and placenta and has the same affinity constant for D-glucose and D-galactose (Km=17 nM).

Hence, according to one embodiment of the present invention mofezolac conjugated with D-galactose by linkers with different length ($GALMOF_n$) may be used in pharmaceutical composition for the treatment of inflammatory processes and the treatment of several diseases selected for example from the group consisting of cancer, neuroinflammation, neurological diseases, neurodegenerative diseases, ovarian cancer, neck cancer and head cancer. Examples of neurodegenerative disorders are Alzheimer disease, Parkinson disease, amyotrophic lateral sclerosis, multiple sclerosis, traumatic brain injury, and HIV encephalitis. The preferred compounds are $GALMOF_0$, $GALMOF_5$ and $GALMOF_{11}$.

Compounds of the Invention for Use In Vitro, Ex-Vivo and In Vivo Diagnosis by Detecting COX Compounds of the present invention [formula (I)] wherein G is a fluorescent probe, in particular when G is Nile blue or $NBD-C_6$ or $NBD-C_{12}$ or rhodamine, are useful for in vitro, ex-vivo and in vivo diagnosis or imaging. It is a further object of the invention an in vivo method for diagnosis of cancer, in particular ovarian cancer comprising a step of administering to a mammal, preferably a human, an effective amount of a compound of the families described above, in particular a compound wherein G is Nile blue or $NBD-C_6$ or $NBD-C_{12}$ or rhodamine. The Nile blue, NBDs and rhodamine probes have advantages of optical properties with NIR absorption (630 nm) and emission (670 nm) and can detect cancer cells by the fluorescence imaging method. According to one preferred embodiment of the invention, the cancer cells detect by the in vivo or in vitro or ex-vivo imaging method are ovarian cancer cells. The imaging technique may be for example a fluorescence imaging method to detect COX in cancer cells/tumour tissues during surgical resection and inflamed cells and tissues. Failure to adequately recognize tumour margins and an incomplete resection may increase tumour recurrence and decrease the survival rate.

The effective amount administered of the compounds of the present invention will depend on the particular condition to be diagnosed, the age, weight and the overall physical condition of the particular patient as it is well known to the experts in the field. The diagnostically effective amount of the compounds of the present invention to be administered before conducting the in vivo diagnosis is within a range from 0.1 ng to 100 mg per kg body weight, preferably within a range of from 1 ng to 10 mg per kg body weight.

It is a further object of the invention an in vitro method for diagnosis of cancer, in particular ovarian cancer comprising a step of administering an effective amount of a compound of the families described above, in particular a compound wherein G is a fluorescent probe, more in particular wherein G is Nile blue or NBDs or rhodamine, with a sample of cells or tissues.

Compounds of the Invention Isotopically Labeled.

The present invention also encompasses isotopically radiolabeled compounds which are identical to the compounds according to any embodiment herein disclosed but for the fact that one or more atoms are replaced by an atom having atomic mass or mass number different from the atomic mass or mass number usually found in nature. Example of isotopes that can be incorporated into the intermediates or compounds of the invention include isotopes of hydrogen, carbon, nitrogen, oxygen and fluorine, such as $^{3}H$, $^{11}C$, $^{14}C$, $^{13}N$, $^{15}O$, $^{18}F$, respectively. The incorporation of radioactive atom into the compounds of the present invention may be performed using techniques known in the art, for example by the incorporation of radioactive 11-Carbon or 18-Fluorine atom into the compounds of the present invention.

Imaging Composition

A further object of the invention is a diagnostic imaging composition comprising as imaging agents the compounds selected from the above-indicated families, in one embodiment isotopically labeled and a carrier. In accordance with the invention, the compounds according to Formula (I) may be administered in a single unit injectable dose. Any of the common carriers known to those with skill in the art, such as sterile saline solution or plasma, can be utilized after radiolabelling of compounds for preparing the injectable solution to diagnostically imaging in accordance with the invention. Such techniques include the step of bringing into association the active ingredient and the pharmaceutical carrier(s) or diluent(s). In general the formulations are prepared by uniformly and intimately bringing into association the active ingredient with the liquid carrier.

For diagnostic purposes after intravenous administration, imaging of the organ in vivo can take place in a matter of a few minutes. However, imaging takes place, if desired, in hours or even longer, after injecting into patients. In most instances, a sufficient amount of the administered dose will accumulate in the area to be imaged within about 1 hour to permit the taking of diagnostic images. Any conventional method of imaging for diagnostic purposes can be utilized in accordance with this invention as positron emission tomography (PET) or Single photon emission computed tomography (SPECT).

The diagnostic imaging compositions of the invention are useful for use in vivo diagnosis or imaging of a condition in which the COX-1 is the molecular target.

Pharmaceutical Compositions

A further object of the invention is a pharmaceutical composition comprising the compounds selected from the above-indicated families and/or their "pharmacologically accepted salts", and a pharmacologically acceptable excipient and/or carrier. This pharmaceutical compositions and formulation types may contain from 0.1 to about 500 mg of the active ingredient selected from the compounds described in the present invention. Typical unit dosage forms contain from 1 to 100 mg of the active ingredient.

The pharmaceutical compositions of the invention are useful in the treatment or detection of COX-1 relating disorders or diseases such as cancer and neuroinflammation, in particular in neurological and neurodegenerative diseases, and in ovarian cancer, neck and head tumour.

Therapeutic Applications

A further object of the present invention is a compound selected from the above-indicated for use as medicament.

The compounds of the invention find therapeutic applications in the treatment of any condition susceptible of being improved or prevented by selective inhibition of COX-1, in particular in the treatment of COX-1 relating disorders such as cancer and neuroinflammation, more in particular in neurological and neurodegenerative diseases, and in ovarian cancer, neck and head tumour.

More in details a neuroinflammation is difficult to treat due to the difficulty that most of the traditional non-steroidal anti-inflammatory drugs (tNSAIDs) has to cross the blood-brain barrier and, hence, reach the central nervous system. According to one embodiment of the invention the compounds of formula (I) wherein G is a sugar, in particular a galactose, are enable to be recognized by the sugar transporters (GLUT 1 and GLUT 2) expressed at the blood-brain barrier as also showed in the experimental section of the present application.

Method for Treatment

It is a further object of the invention a method for treating any disorders or diseases susceptible of being improved or prevented by selective inhibition of COX-1, comprising administering to a mammal requiring such treatment an effective amount of any compounds herein disclosed. In particular, said disease is selected from the group consisting of cancer, neuroinflammation, neurological diseases, neurodegenerative diseases, ovarian cancer, neck cancer and head cancer, in particular in neurological (e.g. autism spectrum disorders) and/or neurodegenerative diseases (e.g. Alzheimer's diseases, Parkinson's diseases, amyotrophic lateral sclerosis (ALS), multiple sclerosis (MS), traumatic brain injury (TBI), HIV dementia and prion diseases.

In the method of treatment, the effective amount administered and frequency of administration of the compounds of the present invention will depend on the particular condition to be treated, the severity of the condition to be treated, age, weight and the overall physical condition of the particular patient, as well as on other medicaments the patient is taking, as it is well known to the experts in the field.

The effective amount of the compounds of the invention to be administered daily or per dosage, is within a range of from 0.1 ng to 100 mg per kg body weight, preferably within a range of from 1 ng to 10 mg per kg body weight.

EXAMPLES, CHEMICAL AND BIOLOGICAL DATA

The invention is detailed hereinafter via the following examples of preparation of the new compounds and through their biological testing.

Examples

1.1 Synthesis of the GALMOF$_n$ Compounds (n=0, 4, 10)

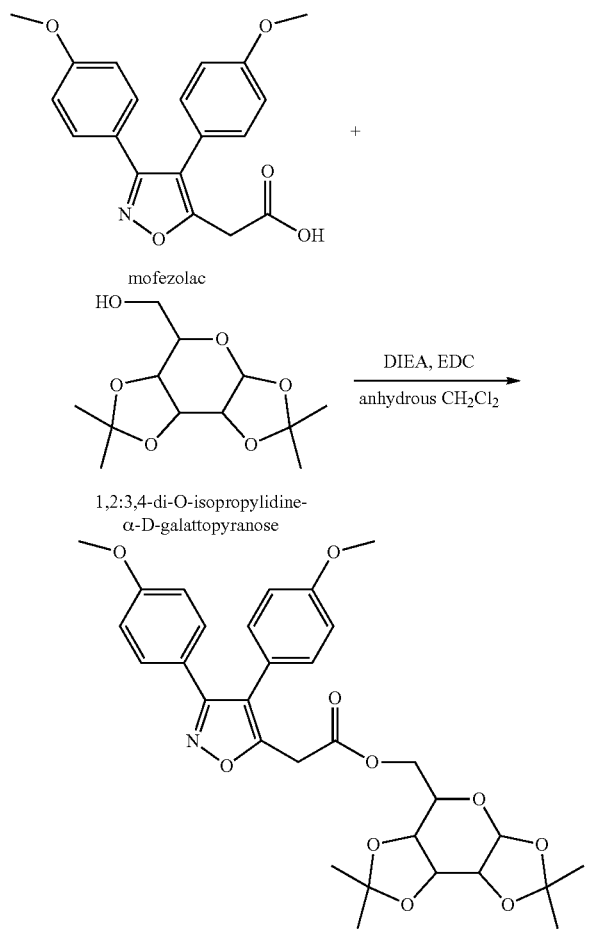

1,2:3,4-Di-O-isopropylidene-6-O-{2-[3,4-bis(4-methoxyphenyl)isoxazol-5-yl]acetyl}-D-galactopyranose.
To a cold (ice-bath) solution of 2-(3,4-bis(4-methoxyphenyl)isoxazol-5-yl)acetic acid (mofezolac, 300 mg, 0.885 mmol) and 1,2:3,4-Di-O-isopropylidene-D-galactose (230 mg, 0.885 mmol) in CH$_2$Cl$_2$ (5 mL), 4-(dimethylamino)pyridine (DMAP) (27 mg, 0.22 mmol), and 1V-(3-dimethylaminopropyl)-N'-ethylcarbodiimide hydrochloride (EDC HCl, 680 mg, 3.56 mmol) were added in portions under argon atmosphere. The reaction mixture was stirred at room temperature for 24 h and then quenched by adding distilled water. The aqueous phase was extracted three times with EtOAc. The combined organic phases were dried over anhydrous Na$_2$SO$_4$, filtered, and the solvent removed under reduced pressure. The product (375 mg) was isolated by column chromatography (silica gel; CHCl$_3$/MeOH 95:5) of the reaction crude. 73% Yield. $^1$H NMR (300 MHz, CDCl$_3$, δ): 7.41-7.36 (m, 2H, aromatic protons); 7.19-7.14 (m, 2H, aromatic protons); 6.94-6.89 (m, 2H, aromatic protons); 6.85-6.81 (m, 2H, aromatic protons); 5.53 (d, 1H, J=4.95 Hz); 4.61 (dd, 1H, J=8.0 Hz, J=2.5 Hz); 4.34-4.25 (m, 2H); 4.18 (dd, 2H, J=8.0 Hz, J=1.9 Hz); 4.05-3.99 (m, 1H); 3.83 (s, 3H OCH$_3$); 3.80 (s, 3H, OCH$_3$); 3.79 (s, 2H, CH$_2$); 1.45 (s, 6H, 2CH$_3$); 1.32 (s, 3H); 1.31 (s, 3H). ESI-MS m/z (%): C$_{31}$H$_{35}$NO$_{10}$ (M+Na)$^+$: 604.

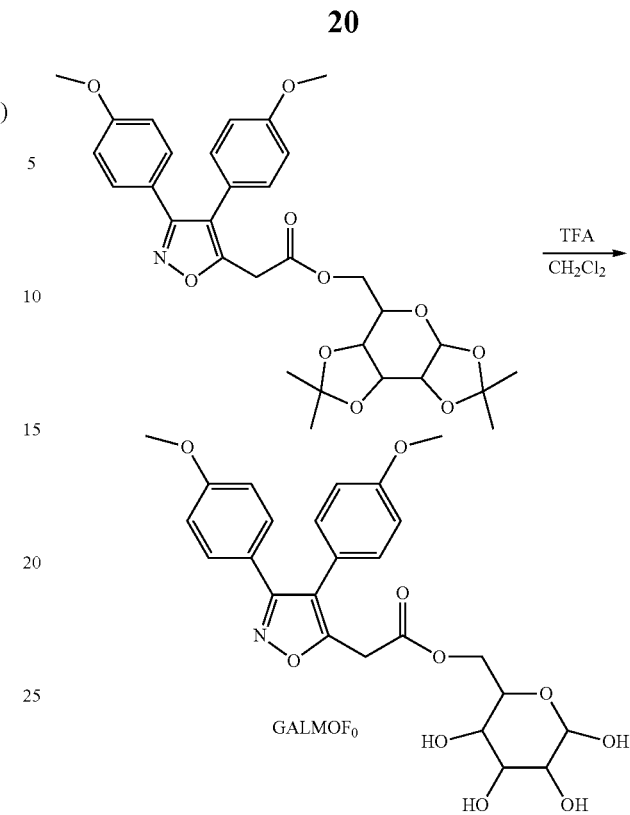

((2S,3R,4S,6R)-3,4,5,6-tetrahydroxytetrahydro-2H-pyrano-2-yl-) methyl-(2-(3,4-di(4-metoxyphenyl)isoxazol-5-yl)acetate. Trifluoracetic acid (TFA, 1.3 mL, d=1.47 g/mL, 16.7 mmol)) was added to a solution of 1,2:3,4-di-O-isopropylidene-6-O-{2-[3,4-bis(4-methoxyphenyl)isoxazol-5-yl]acetyl}-D-galactopyranose (440 mg, 0.76 mmol) in dry CH$_2$Cl$_2$ (5 mL). The reaction mixture was stirred at room temperature for 24 h. The progress of the reaction was monitored by TLC. Then, the solvent was distilled under reduced pressure and the product isolated as a white solid (148 mg, 39% yield) by a column chromatography (silica gel; CHCl$_3$/MeOH=9:1) of the crude residue. Mp 117-119° C. $^1$H NMR (500 MHz, CDCl$_3$, δ): 7.29-7.27 (m, 2H, aromatic protons); 7.26-7.05 (m, 2H, aromatic protons); 6.81-6.80 (m, 2H, aromatic protons); 6.76-6.73 (m, 2H, aromatic protons); 5.50-5.35 (bs, 4H, OH: exchange with D$_2$O); 5.38 (s, 1H, 1'H galactose); 4.60 (s, 1H, 3'H galactose); 4.29-4.22 (m, 2H, 2'H-4'H galactose); 4.07-4.02 (m, 1H, 5'H galactose); 3.84-3.81 (dd, 2H, 6'H galactose); 3.84 (s, 3H, OCH$_3$); 3.73 (s, 3H, OCH$_3$); 3.74 (s, 2H, OCH$_2$). $^{13}$C NMR (75 MHz, CDCl$_3$, δ): 168.1, 161.9, 161.8, 160.7, 160.5, 159.3, 131, 129.7, 121.2, 120.8, 117.5, 114.3, 113.9, 72.4, 55.15, 31.6, 29.6. ESI-MS m/z (%): C$_{25}$H$_{27}$NO$_{10}$ (M+Na)$^+$: 524.

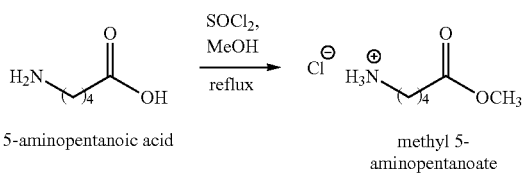

Methyl 5-aminopentanoate hydrochloride. To a stirred solution 5-aminopentanoic acid (500 mg, 4.27 mmol) in dry MeOH (5 mL) kept at −10° C., SOCl₂ (1.1 mL, d=1.631 g/mL, 15 mmol) was dropwise added. The obtained reaction mixture was refluxed for 3 h. Then, SOCl₂ excess and MeOH were distilled under reduced pressure, using a NaOH trap. The product was obtained as a white solid in 79% yield (645 mg) and used in the following reaction without any further purification. ¹H NMR (300 MHz, CDCl₃, δ): 8.28 (bs, 3H, NH₃); 3.67 (s, 3H, OCH₃); 3.04 (m, 2H, CH₂NH₂); 2.38 (t, 2H, CH₂CO); 1.8-1.73 (m, 4H, CH₂CH₂).

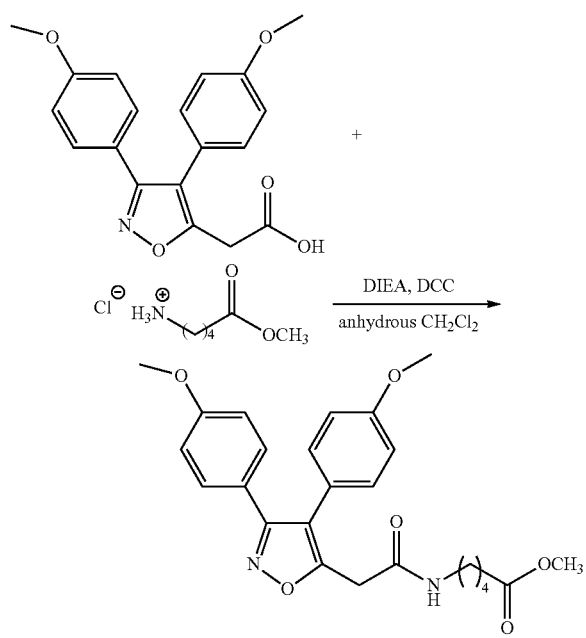

Methyl 5-{2-[3,4-di(4-methoxyphenyl)isoxazol-5-yl]acetamido}pentanoate. Diisopropyl ethylamine (DIEA, 0.215 mL, 1.237 mmol) and methyl 5-aminopentanoate hydrochloride (100 mg, 0.60 mmol) were solubilized in dry CH₂Cl₂ (5 mL) and stirred at 0° C. for 1 h. Then, this solution was dropwise added to a stirred solution of N,N'-dicyclohexylcarbodiimide (DCC, 170 mg, 0.825 mmol), 1-hydroxybenzotriazole monohydrate (HOBt H₂O, 180 mg, 1.05 mmol) and 2-[3,4-bis(4-methoxyphenyl)isoxazol-5-yl] acetic acid (mofezolac) (200 mg, 0.59 mmol) in dry CH₂Cl₂ (20 mL) kept at 0° C. The reaction was stirred for 19 h at room temperature. Then, H₂O was added and the aqueous solution extracted with CH₂Cl₂. The combined organic layers were washed with a sat. solution of K₂CO₃, dried over anhydrous Na₂SO₄, and the solvent was removed under reduced pressure. Column chromatography of the crude residue (silica gel; EtOAc/Hexane=3:7) afforded the product as a solid (107 mg, 40% yield). FT-IR (KBr): 3458, 3089, 2987, 2948, 1737, 1652, 1609, 1562, 1516, 1455, 1441, 1426, 1253, 1233, 1175, 1108, 1029, 1019, 949, 831, 729 cm⁻¹. ¹H NMR (300 MHz, CDCl₃, δ): 7.41-7.37 (m, 2H, aromatic protons), 7.17-7.14 (m, 2H, aromatic protons), 6.92-6.89 (m, 4H, aromatic protons), 5.9 (bs, 1H, NH: exchanges with D₂O), 3.83 (s, 3H, OCH₃), 3.80 (s, 3H, OCH₃), 3.67 (s, 2H, CH₂CONH), 3.65 (s, 3H, OCH₃), 3.27 (q, 2H, J=6.9 Hz, NHCH₂), 2.33 (t, 2H, J=6.9 Hz, CH₂CO₂), 1.65-1.50 (m, 4H, CH₂CH₂). ¹³C NMR (75 MHz, CDCl₃, δ): 174.1, 166.8, 162.8, 161.4, 160.8, 159.7, 131.2, 130.0, 121.6, 121.2, 117.8, 114.6, 114.2, 55.5, 55.4, 39.7, 34.4, 33.6, 29.0, 22.2. ESI-MS: m/z (%): C₂₅H₂₈N₂O₆ (M+Na)⁺: 475.

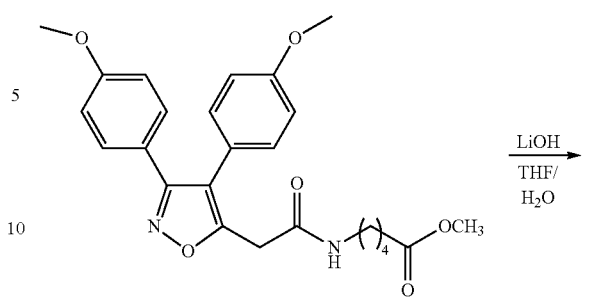

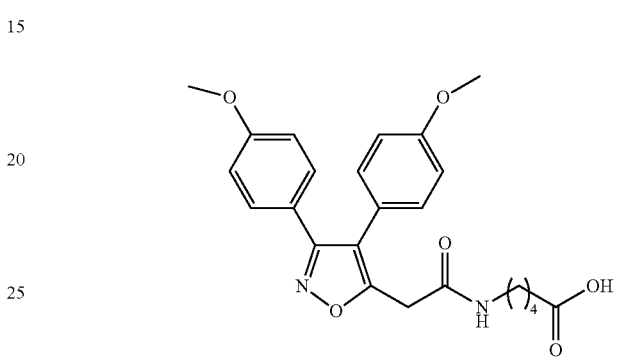

5-(2-(3,4-di(4-methoxyphenyl)isoxazol-5-yl)acetamido) pentanoic acid. To a solution of methyl 5-(2-(3,4-bis(4-methoxyphenyl)isoxazol-5-yl)acetamido)pentanoate (50 mg, 0.11 mmol) in THF (2 mL) was dropwise added a solution of 0.5 N LiOH (68 mg, 2.83 mmol, in 6 mL of H₂O) at room temperature. After 2 h, 1N HCl (5 mL) was added and the aqueous phase was extracted with EtOAc. The combined organic layers were dried over anhydrous Na₂SO₄ and the solvent evaporated under reduced pressure affording the product as a white solid (30 mg, 63% yield). FT-IR (KBr): 3330, 2921, 1720, 1641, 1607, 1540, 1514, 1468, 1424, 1406, 1303, 1247, 1180, 1030, 952, 901, 831 cm⁻¹. ¹H NMR (300 MHz, CDCl₃, δ): 7.37-7.34 (m, 2H, aromatic protons), 7.15-7.12 (m, 2H, aromatic protons); 6.90-6.87 (m, 2H, aromatic protons), 6.83-6.81 (m, 2H, aromatic protons), 6.28 (bs, 1H, NH: exchanges with D₂O), 3.81 (s, ³H, OCH₃); 3.78 (s, 3H, OCH₃); 3.67 (s, 2H, CH₂CONH); 3.26 (q, 2H, J=6.1 Hz, NHCH₂); 2.37 (t, 2H, J=6.6 Hz, CH₂CO₂); 1.61-1.41 (m, 4H, CH₂CH₂). ¹³C NMR (75 MHz, CDCl₃, δ): 177.2, 166.9, 162.8, 161.4, 160.9, 159.7, 131.3, 130.1, 121.5, 121.1, 117.8, 114.6, 114.2, 55.6, 55.4, 39.7, 34.4, 33.3, 28.9, 21.9. ESI-MS m/z (%): C₂₄H₂₆N₂O₆ (M+Na)⁺: 461; (M−H)⁻: 437.

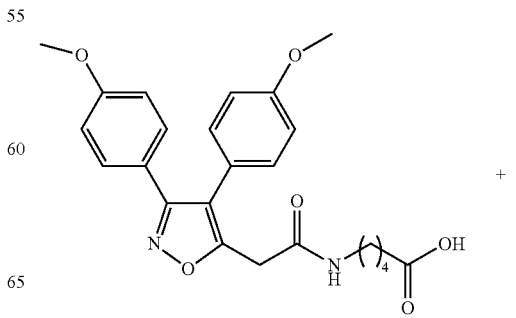

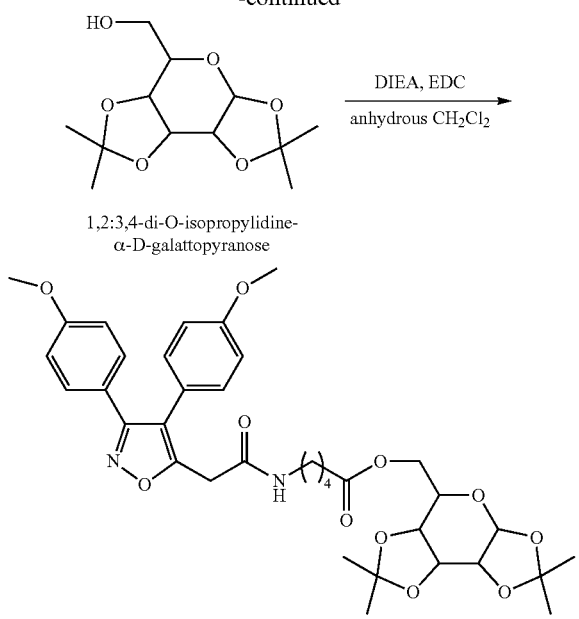

1,2:3,4-di-O-isopropylidine-α-D-galattopyranose

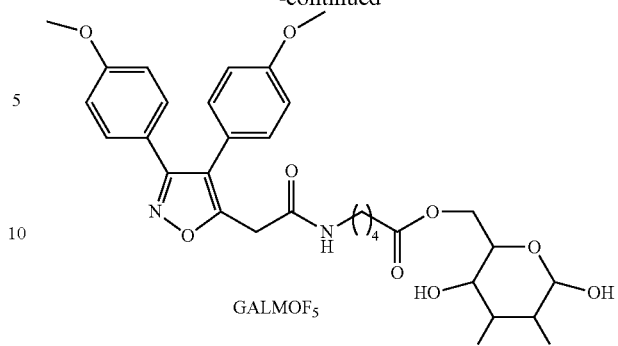

GALMOF₅

6-O-(5-{2-[3,4-bis(4-methoxyphenyl)isoxazol-5-yl] acetamido}pentanoyl)-D-galactopyranose. Trifluoroacetic acid (TFA, 0.31 mL, d=1.47 g/mL, 4 mmol) was added to a solution of 1,2:3,4-di-O-isopropylidene-6-O-(5-{2-[3,4-bis (4-methoxyphenyl) isoxazol-5-yl]acetamido}pentanoyl)-D-galactopyranose (68 mg, 0.10 mmol) in $CH_2Cl_2$ (2 mL) and the mixture was kept at room temperature for 48 hours and monitored by TLC. The solvent was evaporated to dryness under reduced pressure, to give a semi-solid residue which column chromatography (silica gel; $CHCl_3/MeOH=9:1$), allowed to isolate the product (35 mg, 58%, α/ρ 1/3.7). Mp 85-87° C. ¹H NMR (500 MHz, $CDCl_3$, δ): 7.36-7.28 (m, 2H, aromatic protons); 7.20-7.18 (m, 2H, aromatic protons); 6.98-6.90 (m, 2H, aromatic protons); 6.90-6.84 (m, 2H, aromatic protons); 5.65-5.40 (bs, 4H, OH: exchange with $D_2O$); 5.32-5.31 (m, 1H); 4.30-4.27 (m, 1H); 4.10-4.09 (m, 2H); 3.85-3.83 (m, 2H); 3.76 (s, 3H, $OCH_3$); 3.73 (s, 3H, $OCH_3$); 3.53-3.50 (m, 3H, $CH_2CONH$ and $H_{gal}$); 3.07-3.01 (m, 2H, $NHCH_2$); 2.38-2.30 (m, 2H, $CH_2CO_2$); 1.5-1.38 (m, 4H, $CH_2CH_2$). ESI-MS m/z (%): $C_{30}H_{36}N_2O_{11}$ (M+Na)⁺: 623.

1,2:3,4-Di-O-isopropylidene-6-O-(5-{2-[3,4-bis(4-methoxyphenyl)isoxazol-5-yl]acetamido}pentanoyl)-D-galactopyranose. To a solution of 5-{2-[3,4-bis(4-methoxyphenyl)isoxazol-5-yl]acetamido}pentanoic acid (85 mg, 0.194 mmol) and 1,2:3,4-Di-O-isopropylidene-D-galactose (51 mg, 0.196 mmol) in $CH_2Cl_2$ (5 mL), kept under stirring and at 0° C., 4-(dimethylamino)pyridine (DMAP, 5 mg, 0.041 mmol), and N-(3-dimethylaminopropyl)-N'-ethylcarbodiimide hydrochloride (EDC HCl, 149 mg, 0.78 mmol) were added in portions under argon atmosphere. Then, the reaction mixture was stirred at room temperature for 24 h, the organic layer was washed with water and brine, dried over $Na_2SO_4$, filtered, and the solvent removed under reduced pressure. The product was isolated as a white solid (71.3 mg, 54% yield) by column chromatography (silica gel; $CHCl_3$/MeOH 95:5) of the reaction crude. ¹H NMR (300 MHz, $CDCl_3$, δ): 7.38-7.35 (m, 2H, aromatic protons); 7.25-7.15 (m, 2H, aromatic protons); 6.92-6.85 (m, 2H, aromatic protons); 6.84-6.80 (m, 2H, aromatic protons); 6.16-6.13 (bs, 1H, NH: exchanges with $D_2O$), 5.52 (m, 1H); 4.61-4.58 (m, 1H); 4.33-4.19 (m, 5H); 3.81 (s, 3H, $OCH_3$); 3.78 (s, 3H, $OCH_3$); 3.65 (s, 2H, $CH_2CONH$); 3.33-3.17 (m, 2H, $NHCH_2$); 2.34-2.29 (m, 2H, $CH_2CO_2$); 1.66-1.5 (m, 4H, $CH_2CH_2$); 1.50 (s, 3H, $CH_3$); 1.42 (s, 3H, $CH_3$); 1.317 (s, 3H, $CH_3$); 1.3 (s, 3H, $CH_3$). ESI-MS: m/z (%): $C_{36}H_{44}N_2O_{11}$ (M+Na)⁺: 703.

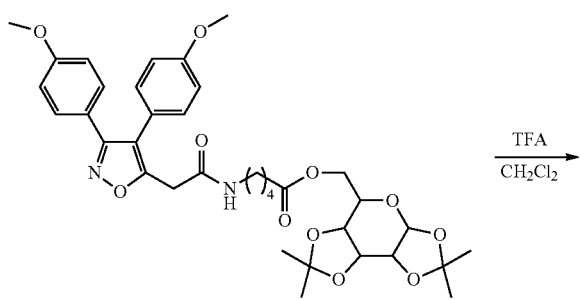

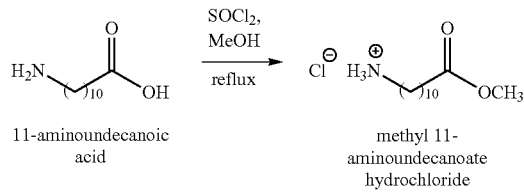

11-aminoundecanoic acid → methyl 11-aminoundecanoate hydrochloride

Methyl 11-aminoundecanoate hydrochloride. $SOCl_2$ (0.55 mL, 7.6 mmol) was dropwise added to a stirred solution of 11-aminoundecanoic acid (500 mg, 2.49 mmol) solubilized in dry MeOH (5 mL) kept at 0° C. The reaction mixture was refluxed for 5 h. When the reaction was completed, the $SOCl_2$ excess and MeOH were distilled under reduced pressure, using a NaOH trap. The product was isolated as a white solid (535 g, 86% yield). ¹H NMR (300 MHz, $CDCl_3$, δ): 3.64 (s, 3H, $OCH_3$); 2.8-2.5 (m, 2H, $NH_2CH_2$); 2.5-2.2 (m, 2H, $CH_2CO$); 2.19 (bs, 3H, $NH_3$: exchange with $D_2O$), 1.61-1.56 (m, 2H, $CH_2CH_2CO$); 1.42-1.41 (m, 2H, $CH_2CH_2NH_2$); 1.36-1.18 (m, 12H, $CH_2$).

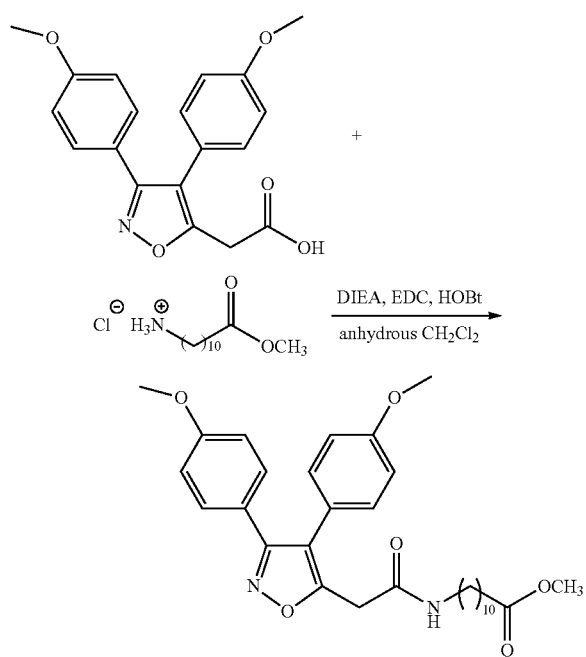

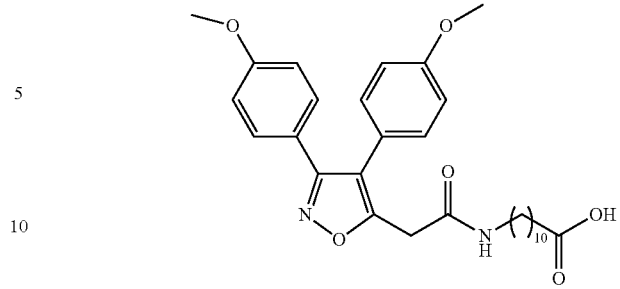

Methyl 11-{2-[3,4-bis(4-methoxyphenyl)isoxazol-5-yl]acetamido}undecanoate. To a stirred solution of mofezolac (500 mg, 1.47 mmol) in dry CH$_2$Cl$_2$ (25 mL), kept at 0° C. by an ice-bath, HOBt monohydrate (253 mg, 1.48 mmol) and EDC hydrochloride (303 mg, 1.58 mmol) were added. Separately a stirred solution of methyl 11-aminoundecanoate hydrochloride (370 mg, 1.38 mmol) in dry CH$_2$Cl$_2$ (13 mL) was mixed with DIEA (0.45 mL, 2.6 mmol) at room temperature. After 2 h, this solution was dropwise added to the reaction mixture and stirred overnight at room temperature. Then, sat. aq. NaHCO$_3$ was added and the aqueous solution extracted three times with EtOAc. The combined organic layers were dried over anhydrous Na$_2$SO$_4$, and the solvent distilled under reduced pressure. Column chromatography (silica gel; CHCl$_3$/MeOH=5:5) of the crude residue afforded the product as a white solid (573 mg, 72% yield). $^1$H NMR (300 MHz, CDCl$_3$, δ): 7.41-7.26 (m, 2H aromatic protons); 7.25-7.13 (m, 2H aromatic protons); 6.93-6.71 (m, 4H aromatic protons), 5.80 (bs, 1H, exchanges with D$_2$O), 3.82 (s, 3H, OCH$_3$), 3.80 (s, 3H, OCH$_3$), 3.67 (s, 2H, CH$_2$), 3.65 (s, 3H, COOCH$_3$), 3.23-3.21 (m, 2H, NHCH$_2$), 2.31-2.26 (t, 2H, CH$_2$CO), 1.62-1.57 (m, 2H, CH$_2$CH$_2$CO), 1.49-1.45 (m, 2H, CH$_2$CH$_2$NH); 1.25-1.10 (m, 12H, CH$_2$). ESI/MS m/z: C$_{31}$H$_{40}$N$_2$O$_6$ (M+Na)$^+$: 559.

Methyl 11-{2-[3,4-bis(4-methoxyphenyl)isoxazol-5-yl]acetamido}undecanoate. To a solution of methyl 11-{2-[3,4-bis(4-methoxyphenyl)isoxazol-5-yl]acetamido}undecanoate (345 mg, 0.64 mmol) in THF (10 mL) a 0.5M LiOH solution (36 mL, 18 mmol) was dropwise added. The reaction mixture was stirred at room temperature for 3 h. Then, 3 M HCl (3 mL) was added. The reaction mixture was extracted three times with EtOAc and the combined organic extracts were dried over anhydrous Na$_2$SO$_4$ and the solvent distilled under reduced pressure. The product was isolated as a white powder (261 mg, 78% yield). $^1$H NMR (300 MHz, CDCl$_3$, δ): 10.50-10.40 (bs, 1H, OH: exchanges with D$_2$O); 7.39-7.36 (m, 2H, aromatic protons); 7.17-7.12 (m, 2H, aromatic protons); 6.92-6.81 (m, 4H, aromatic protons); 5.81 (bs, 1H, NH: exchanges with D$_2$O); 3.82 (s, 3H, OCH$_3$), 3.80 (s, 3H, OCH$_3$); 3.68 (s, 2H, CH$_2$CONH); 3.28-3.21 (m, 2H, NHCH$_2$); 2.32 (t, 2H, CH$_2$CO$_2$H); 1.63-1.59 (t, 2H, CH$_2$CH$_2$CO$_2$H); 1.63-1.59 (t, 2H, CH$_2$CH$_2$CH$_2$CO$_2$H); 1.47-1.44 (t, 2H, CH$_2$CH$_2$NH); 1.42-1.19 (m, 10H, CH$_2$). $^{13}$C NMR (75 MHz, CDCl$_3$, δ): 178.7, 174.1, 167.0, 166.8, 162.9, 161.3, 160.9, 159.7, 131.2, 130.0, 121.4, 121.0, 117.7, 114.6, 114.2, 55.6, 55.3, 40.3, 34.4, 34.0, 29.5, 29.4, 29.3, 29.2, 29.1, 26.9, 24.8. ESI-MS m/z (%): C$_{30}$H$_{38}$N$_2$O$_6$ [M−H]$^-$: 521. ESI-MS-MS m/z (%): 489 (4), 388 (50), 356 (54), 320 (100), 293 (9).

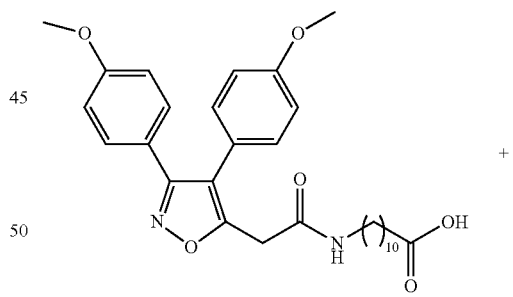

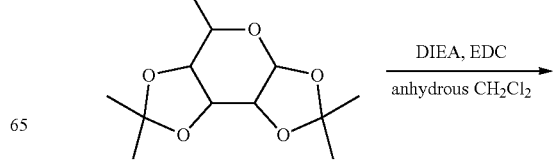

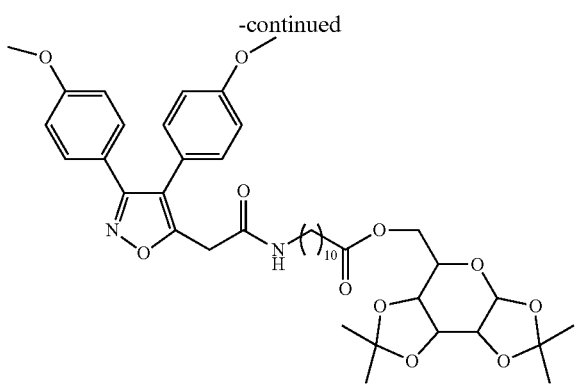

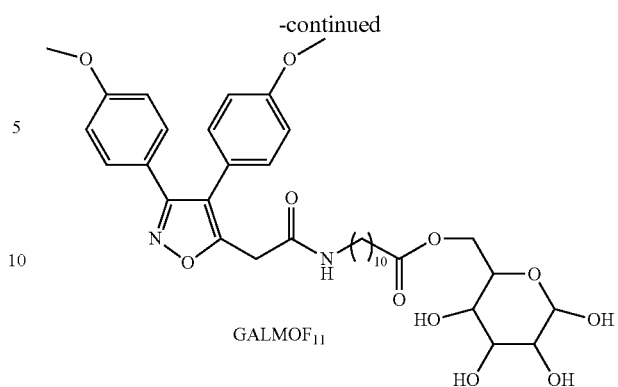

GALMOF$_{11}$ (2,2,7,7-Tetramethyltetrahydro-2αH-bis([1,3]dioxolo)[4,5-b:4'5'-d]pyran-5-yl)methyl 11-{2-[3,4-bis(4-methoxyphenyl)isoxazol-5-yl]acetamido}undecanoate. A cold (0° C. by an ice-bath) solution of methyl 11-{2-[3,4-bis(4-methoxyphenyl)isoxazol-5-yl]acetamido}undecanoate (260 mg, 0.5 mmol), DMAP (14 mg, 0.11 mmol) and EDC hydrochloride (383 mg, 2 mmol) in dry $CH_2Cl_2$ (5 mL) was added to 1,2:3,4-di-O-isopropylidene-α-D-galattopyranose (129 mg, 0.5 mmol) solubilized in dry $CH_2Cl_2$ (5 mL) and the obtained reaction mixture was stirred at room temperature for 24 h. The reaction was quenched with distilled water and extracted three times with EtOAc. The combined organic extracts were dried over anhydrous $Na_2SO_4$ and the solvent was distilled under reduced pressure. Column chromatography (silica gel; $CHCl_3$/MeOH=9:1) of the crude residue afforded the product as a white solid (95 mg, 25% yield). $^1$H NMR (300 MHz, $CDCl_3$, δ): 7.45-7.37 (m, 2H, aromatic protons); 7.19-7.13 (m, 2H, aromatic protons); 6.97-6.89 (m, 2H, aromatic protons); 6.86-6.82 (m, 2H, aromatic protons); 5.75 (bs, 1H, NH: exchanges with $D_2O$); 5.53 (d, 1H, J=4.9 Hz, 1'-H); 4.63-4.59 (dd, 1H, J=2.5 and 7.9 Hz, 3'-H); 4.33-4.28 (m, 2H, 2'-H and 4'-H); 4.25-4.13 (m, 2H, 6'-H); 4.04-3.98 (m, 1H, 5'-H); 3.83 (s, 3H, $OCH_3$); 3.80 (s, 3H, $OCH_3$); 3.67 (s, 2H, $CH_2CONH$); 3.28-3.21 (m, 2H, $NHCH_2$); 2.35-2.29 (m, 2H, $CH_2CO_2$); 1.57, 1.50, 1.44, 1.42 (4s, 12H, ketals); 1.33-1.24 (m, 16H, $CH_2(CH_2)_8CH_2$). ESI-MS m/z (%): $C_{42}H_{56}N_2O_{11}$ [M–H]$^-$:763. ESI-MS-MS m/z (%): 503 (36), 294 (100), 264 (66).

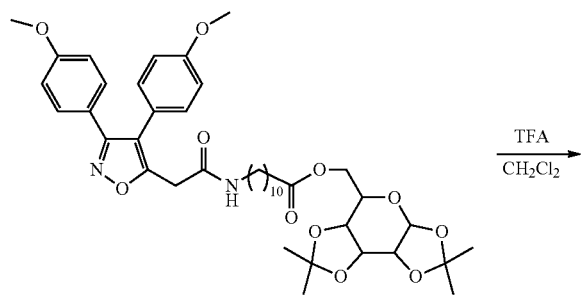

TFA
$CH_2Cl_2$

[(2S,3R,4S,6R)-3,4,5,6-tetrahydroxytetrahydro-2H-pyran-2-yl-]mhetyl 11-{2-[3,4-bis(4-methoxyphenyl)isoxazol-5-yl-]acetamido}undecanoate. Trifluoracetic acid (TFA, 0.7 mL, d=1.47 g/mL, 8.72 mmol)) was added to a solution of (2,2,7,7-Tetramethyltetrahydro-2αH-bis([1,3]dioxolo)[4,5-b:4'5'-d]pyran-5-yl)methyl 11-{2-[3,4-bis(4-methoxyphenyl)isoxazol-5-yl]acetamido}undecanoate (173 mg, 0.226 mmol) in dry $CH_2Cl_2$ (5 mL). The reaction mixture was stirred at room temperature for 48 h. Then, the solvent was distilled and the product isolated as a white solid (70 mg, 45% yield) by a column chromatography (silica gel; $CHCl_3$/MeOH=9:1) of the crude residue. Mp 88-90° C. $^1$H NMR (500 MHz, $CDCl_3$, δ): 7.32-7.30 (m, 2H, aromatic protons); 7.13-7.11 (m, 2H, aromatic protons); 6.86-6.84 (m, 2H, aromatic protons); 6.80-6.78 (m, 2H, aromatic protons); 5.80-5-65 (bs, 4H, OH: exchange with $D_2O$); 5.32-5.30 (m, 1H, 1'-H); 4.71-4.53 (m, 1H, 3'-H); 4.24-4.19 (m, 2H, 2'-H and 4'-H); 4.09-3.96 (m, 2H, 6'-H); 3.78 (s, 3H, $OCH_3$); 3.76 (s, 3H, $OCH_3$); 3.61-3.53 (m, 4H, $CH_2CONH$ and 5'-H); 3.20-3.19 (m, 2H, $NH_2CH_2$); 3.0-2.34 (m, 2H, $CH_2CO_2$); 1.55-1.46 (m, 4H, $NHCH_2CH_2$, $CH_2CH_2CO_2$); 1.26-1.11 (m, 12H, $CH_2(CH_2)_6CH_2$). $^{13}$C NMR (75 MHz, DMSO-d$_6$, δ): 173.6, 166.8, 165.0, 160.8, 159.6, 131.6, 130.0, 122.0, 121.6, 117.0, 114.8, 73.7, 72.4, 55.8, 55.7, 34.0, 33.5, 29.6, 29.4, 29.1, 27.0, 25.1. ESI$^-$/MS m/z: $C_{36}H_{48}N_2O_{11}$: 707 [M+Na]$^+$; ESI$^-$/MS/MS m/z: 689 (8), 647 (24), 584 (100), 545 (25). Anal. C, H, N [ ].

1.2 Cyclooxygenase Inhibition by GALMOF$_n$ (n=0, 4, 10)

Human cyclooxygenase inhibitory activity was determined by a colorimetric COX Inhibitor screening Assay which measures the peroxidase component of the cyclooxygenases, monitoring the appearance of oxidized N,N,N',N'-tetramethyl-p-phenylenediamine (TMPD) at 590 nm. Mofezolac is a selective and potent COX-1 inhibitor with IC$_{50}$=0.0079 μM and 38% inhibition on COX-2 at the highest inhibitor concentration of 50 μM (FIG. 1 and Table 1). The direct conjugation of mofezolac with D-galactose (GALMOF$_0$) determines a reduction of the inhibitory potency and selectivity: COX-1 IC$_{50}$=0.1 μM and COX-2 IC$_{50}$=3.1 μM with 87% inhibition on COX-2 isoform at 50 μM.

Detrimental is the insertion of a C$_4$-linker (GALMOF$_5$) between the two moieties (mofezolac and D-galactose) because COX-1 IC$_{50}$ is >50 μM and percentage of inhibition at 50 μM resulted to be 38 and 24% for COX-1 and COX-2, respectively.

A longer spacer as for C$_{10}$-linker (GALMOF$_{11}$) determines a recovery of COX-1 activity and selectivity, Galmof$_{11}$ resulted to be a potent COX-1 inhibitor with an IC$_{50}$ of 0.4 μM and a percentage of inhibition of COX-1 equal to 90% and but not selective in fact the $IC_{50}$ on COX-2 was 0.27 µM and a percentage of inhibition of 64%.

TABLE 1

COX inhibitory activity[a] of mofezolac and $GALMOF_n$.

| Inhibitor | COX-1 | | COX-2 | |
|---|---|---|---|---|
| | $IC_{50}$ µM | inhibition (%)[b] | $IC_{50}$ µM | inhibition (%)[b] |
| mofezolac | 0.0079 | 100 | — | 38 |
| $GALMOF_0$ | 0.1 | 100 | 3.1 | 87 |
| $GALMOF_5$ | >50 | 38 | >50 | 24 |
| $GALMOF_{11}$ | 0.4 | 90 | 0.27 | 64 |

[a]Values are the means of at least three independent measurements.
[b]Percentage (%) of inhibition determined at 50 µM, the highest concentration of the inhibitor tested.

1.3 $GALMOF_0$ Permeability Experiments

Figure 2:
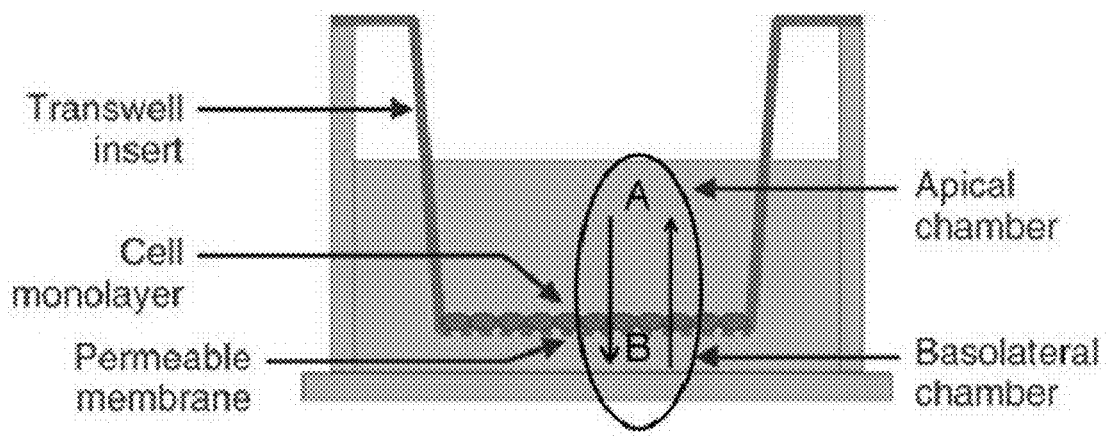
FIG. 2. Schematic representation of Caco-2 monolayer in a transwell system.

In a monolayer efflux assay, the Apparent Permeability (Papp) in both basolateral to apical [Papp(B→A)] and apical to basolateral [Papp(A→B)] directions was determined for each compound (FIG. 2). Human colonic adenocarcinoma cell line (Caco-2) presents a facilitated transport system at the apical and basolateral surface. Caco-2 cells express high levels of GLUT-1 that are localized to the basolateral membrane and transport glucose to the serosal side.

The Papp(B→A) flux of each compound alone or in the presence of phloretin, a GLUT-1 inhibitor, has been determined. Since GLUT-1 is express in the basolateral compartment a high B→A flux means that the transport is GLUT-1 mediated because B→A flux represents the active transport.

A→B flux, which represents the passive transport, has also been determined for each compound (Table 2).

TABLE 2

Papp (nm/sec) values of $GALMOF_n$ alone and in the presence of 100 mM Phloretin.

| | Papp B → A | | Papp A → B | |
|---|---|---|---|---|
| Mofezolac | 461 | — | 414 | — |
| | | Phloretin | | Phloretin |
| $GALMOF_0$ | 875 | 610 | 380 | 368 |
| $GALMOF_5$ | 749 | 472 | 321 | 321 |
| $GALMOF_{11}$ | 772 | 622 | 292 | 292 |

Mofezolac B→A and A→B fluxes were determined and the corresponding Papp, as expected, are comparable since no active transport is involved in mofezolac transport. Much higher Papp(B→A) values are observed for all GALMOFs with respect to mofezolac thus indicating that a carrier-mediated active transport mechanism is implicated.

$GALMOF_0$ shows an apparent permeability of 875 nm/sec whereas in the presence of phloretin a 30% reduction of the basolateral to apical flux was observed (Papp(B→A)= 610 nm/sec) whereas the passive transport is not influenced by the GLUT-1 inhibitor pretreatment.

For $GALMOF_5$ the percentage of the apparent permeability reduction is of 37%, similar to that of $GALMOF_0$ (Papp(B→A) varies from 749 to 472 nm/sec in the presence of the GLUT-1 inhibitor.

The apparent permeability of $GALMOF_{11}$ (Papp(B→A)= 772 nm/sec) in the presence of phloretin decreases by 20% (Papp(B→A)=622 nm/sec). Passive transport remains unchanged regardless of the length of the linker independently of the phloretin preincubation.

These reductions indirectly demonstrate the involvement of Glut-1 in GALMOFs transport across Caco-2 cells monolayer and it can be assumed that mofezolac linked to galactose is capable to cross the monolayer quicker than mofezolac alone, Papp(B→A) of 461 nm/sec becomes 875, 749 and 772 nm/sec for $GALMOF_0$, $GALMOF_5$ and $GALMOF_{11}$, respectively.

1.4 $GALMOF_n$ Immunofluorescence Experiments

To confirm the presence of GLUT-1 in Caco-2 cell line, cells were fixed and immunofluorescently stained with an anti-Glut1 mouse monoclonal antibody. The primary antibody was visualized using AlexaFluor® 594 labeled secondary antibody and the nuclei were counterstained with Hoechst 33342.

Figure 3:
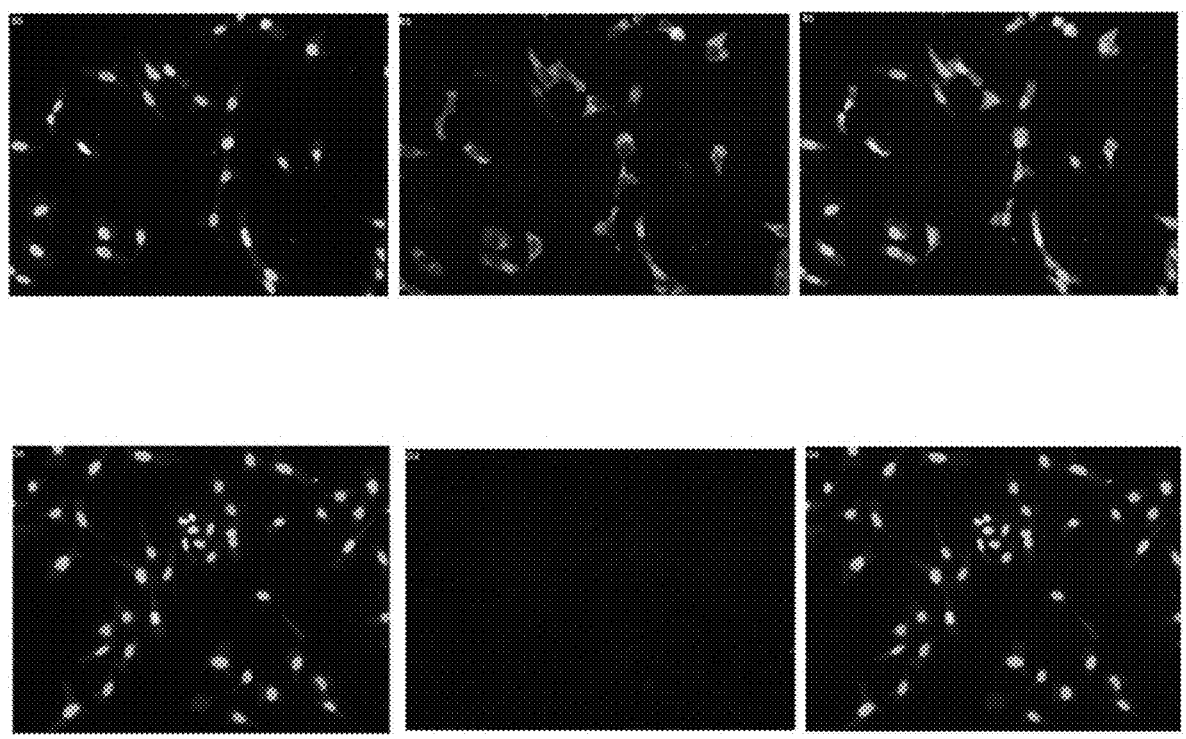
FIG. 3. Perkin-Elmer Operetta images (20× magnification) acquired from Hoechst 33342 ($\alpha,\alpha'$) and Alexa Fluor® 594 (b, b') channels (a,b: anti-Glut-1 mouse monoclonal antibody; a',b': non immune control). Merged images of a-b ad a'-b' are shown in c and c', respectively.

There was positive GLUT-1 signal staining in the cells incubated with anti-Glut-1 mouse monoclonal antibody, whereas no staining was observed in the cells incubated with BSA3% (non immune control) (FIG. 3).

1.5 $GALMOF_0$ Chemical Stability

HPLC analyses were performed to determine the chemical stability and the purity grade of $GALMOF_0$ as a representative compound of the set.

Aminica column was used, $CH_3CN$/10 mM Tris-HCl (pH=8) (15:85) was used as mobile phase, T=40° C.; λ=254 nm.

TABLE 3

Figure 4:
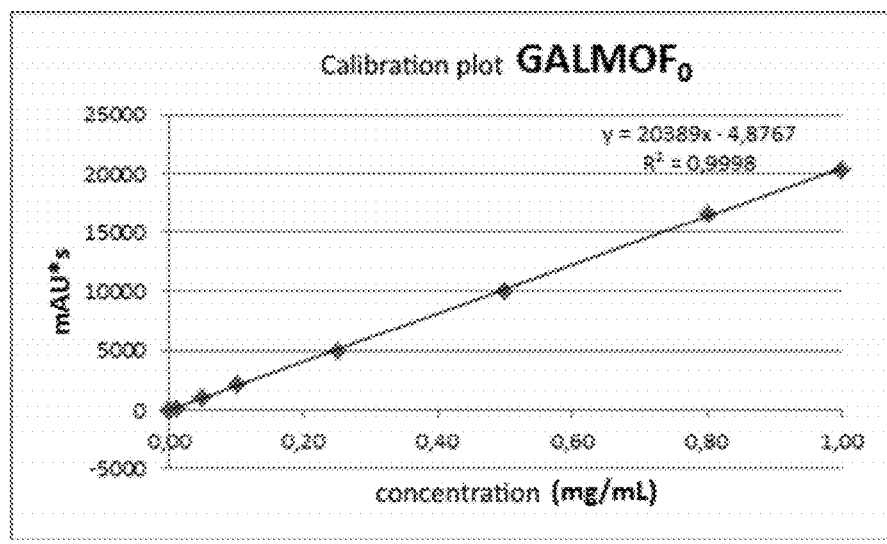
FIG. 4. Calibration plot of $GALMOF_0$.

$GALMOF_0$ concentrations used to build the "concentration plot" (FIG. 4).

| Concentration (mg/mL) | mAU*s | Conc. mg/mL | mAU*s |
|---|---|---|---|
| 0 | 0 | 0.1 | 20105.2 |
| 0.0001 | 1.33 | 0.25 | 4952.14 |
| 0.001 | 27.6 | 0.5 | $1.01e^4$ |
| 0.01 | 197.2 | 0.8 | $1.65e^4$ |
| 0.05 | 1043.9 | 1 | $2.03e^4$ |

200 µL of 2.5 mg/mL di $GALMOF_0$ in $CH_3CN$ were added to 1800 µL of a buffer (pH=1, 3, 7.3 and 8). Each sample was kept stirred at 37° C. Buffer with pH=1 and 3, obtained with 0.1N HCl and 50 mM HEPES, was selected to simulate the chemical stability at gastric level, whereas pH=7.3 and 8, obtained by 50 mM TRIS-HCl, simulated its stability in the blood and gut, respectively.

Figure 5:
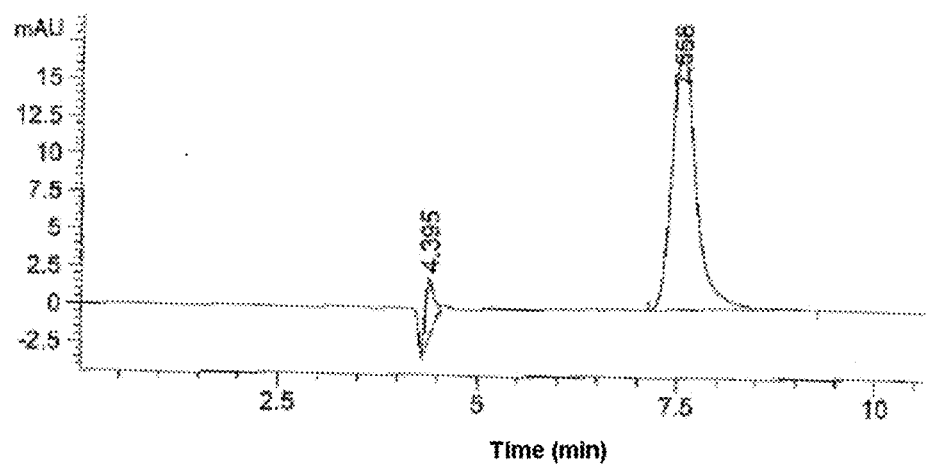
FIG. 5. HPLC elution profile of $GALMOF_0$.

At 15, 30, 60 min and 48 h, 300 µL of the sample were withdraw, diluted with 300 µL of $CH_3CN$ (final concentration=0.075 mg/mL) and tested by HPLC. For all the pH values and till 60 min, the retention time (Rt) remained constant (7.5 min) and no variation of the chromatogram profile was observed (FIG. 5).

Figure 6:
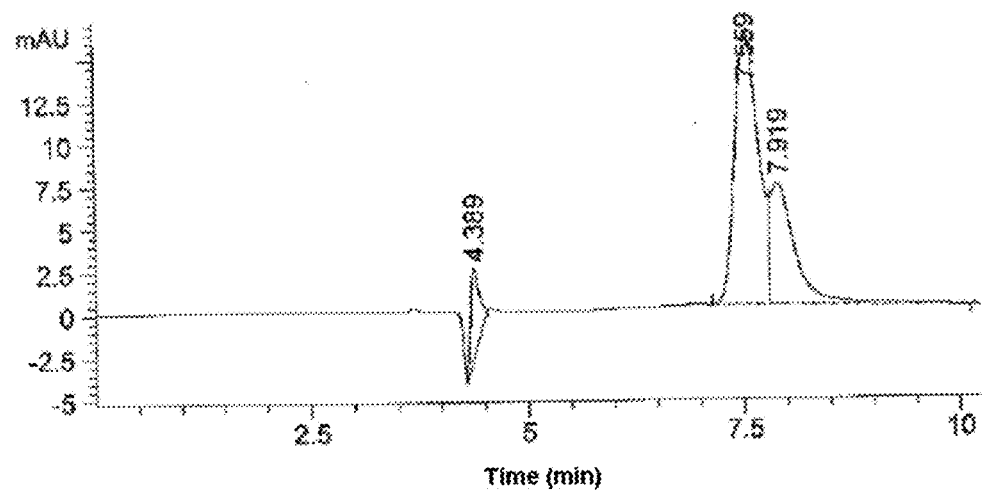
FIG. 6. HPLC elution profile of $GALMOF_0$ after 48 h incubation at 37° C. and pH=7.3.
Figure 7:
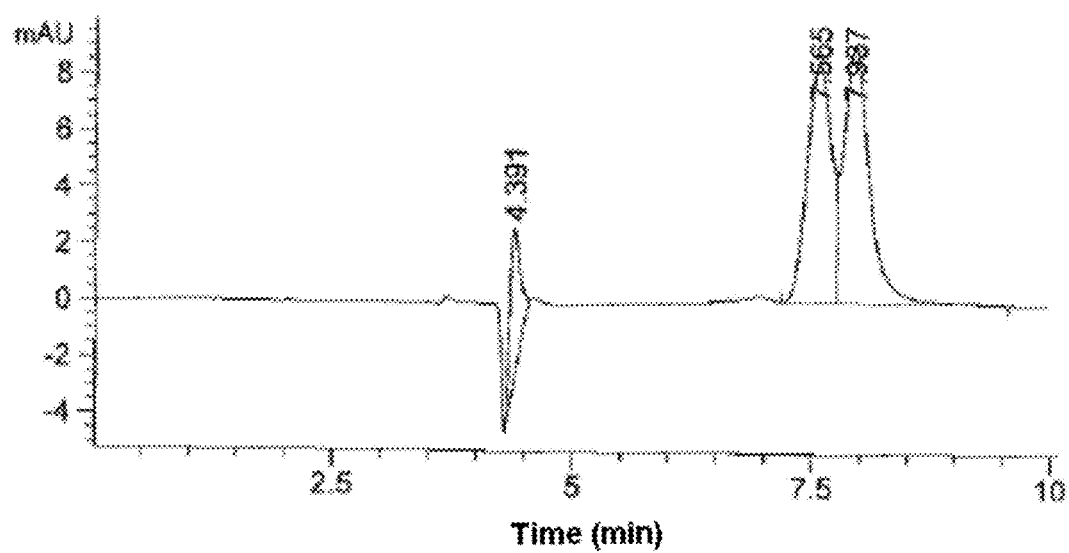
FIG. 7. HPLC elution profile of $GALMOF_0$ after 48 h incubation at 37° C. and pH=8.

At 48 h and pH=7.3 and 8, another peak at 7.9 min appeared in the chromatogram, that was 32% at pH=7.3 (FIG. 6) and 53% at pH=8 (FIG. 7).

1.6 $GALMOF_0$ Metabolic Stability $GALMOF_0$ metabolic stability was determined through its incubation with rat liver microsomes and monitoring the disappearance of its chromatogram peak within 30 min.

The in vitro test was carried out in the presence of rat liver S9 fraction (Tebu-bio, Milan, Italy).

Briefly, $GALMOF_0$ (10 µM) in 100 mM of phosphate buffer (pH=7.4) was mixed with the NADPH regeneration system to a final concentration of 1.3 mM $NADP^+$, 3.3 mM glucose 6-phosphate and 0.4 U/ml glucose 6-phosphate dihydrogenase and 3.3 mM $MgCl_2$. The experiment started with the addition of rat microsomes (1 mg/ml) that were incubated for 30 min at 37° C. The reaction was blocked by adding an equal volume of cold CH₃CN. The samples were centrifuged at 4,600 rpm for 15 min at 4° C. The supernatant was separated and the organic phase analysed by HPLC in the same conditions used for the samples of the "chemical stability study".

Figure 8:
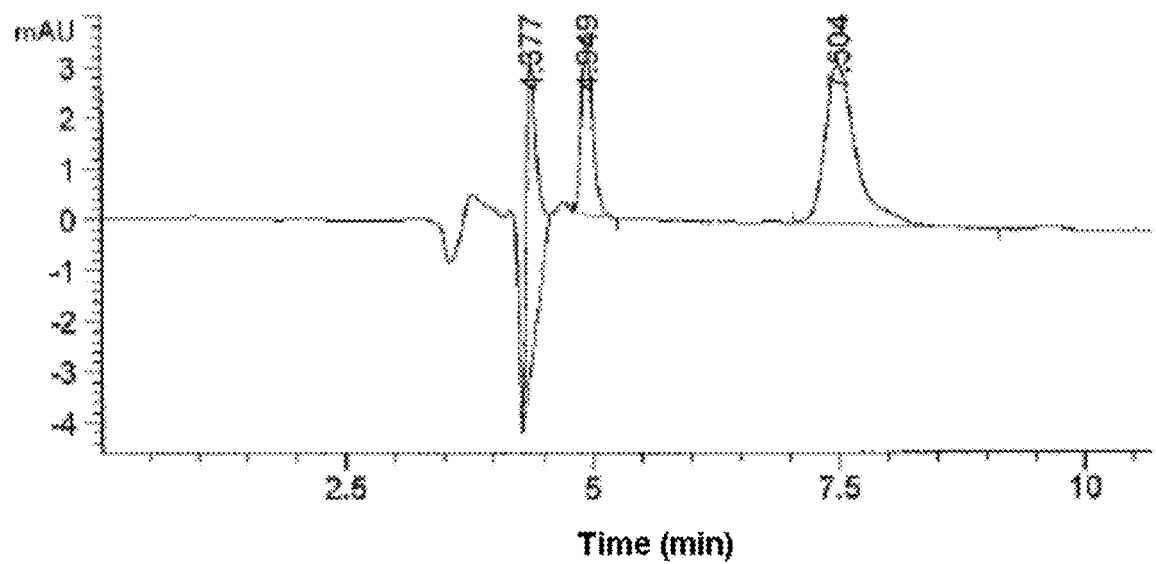
FIG. 8. HPLC elution profile of $GALMOF_0$ incubated with the microsomes and the NADPH regeneration system. $C_{micr+NADPH}$=68.02 mAU*s is the concentration after the incubation. $GALMOF_0$ was found to be metabolically stable. In fact, 96% residual $GALMOF_0$ was found after 30 min of treatment with microsomes.
Figure 9:
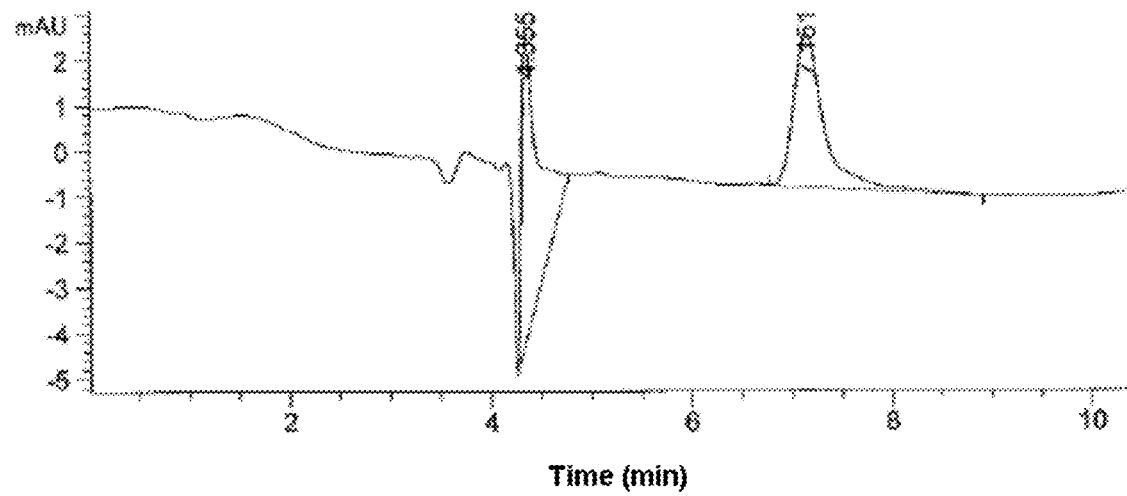
FIG. 9. HPLC elution profile of $GALMOF_0$ incubated with only the microsomes. $C_{micr}$=70.51 mAU*s is the concentration after the incubation.

The residual GALMOF$_0$ percentage after 30 min was calculated according the following equation:

Residual GALMOF$_0$(%) at 30 min=$C_{micr+NADPH}/C_{micr} \times 100$ where $C_{micr+NADPH}$ is the GALMOF$_0$ concentration after the incubation with the microsomes and the NADPH regeneration system (FIG. 8); $C_{micr}$ is the GALMOF$_0$ concentration after the incubation with only the microsomes (FIG. 9).

2. Procedure for the Preparation of Mofezolac-LK-Fluorescent Probe Compounds 2.1 Synthesis of N-{4'-{2-[3,4-bis(4-methoyphenyl)isoxazol-5-yl]acetamido}-(1,1'-biphenyl)-4-yl}-6-[(7-nitrobenzo[c][1,2,5]oxadiazol-4-yl)amino]hexanamide (n=5) and N-{4'-{2-[3,4-bis(4-methoyphenyl)isoxazol-5-yl]acetamido}-(1,1'-biphenyl)-4-yl}-12-[(7-nitrobenzo[c][1,2,5]oxadiazol-4-yl)amino]dodecanamide (n=11)

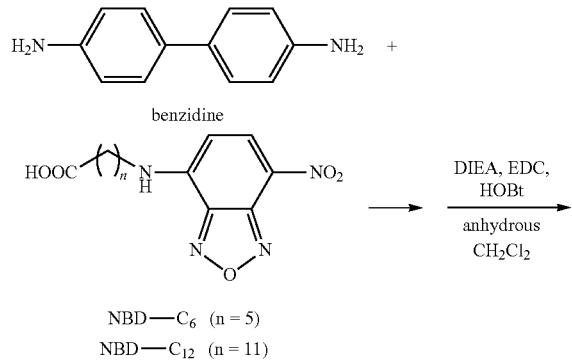

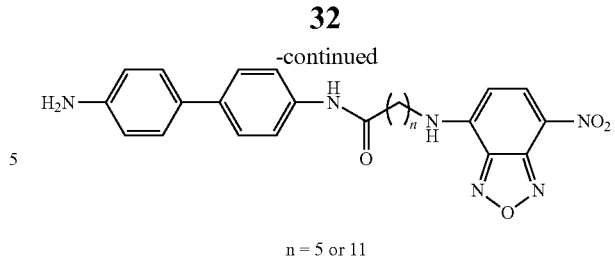

n = 5 or 11

To 6-(7-nitrobenzenfurazan-4-ylamino)hexanoic acid (NBD-C$_6$,100 mg, 0.34 mmol) [or NBD-C$_{12}$,12-(7-nitrobenzenfurazan-4-ylamino)dodecanoic acid] solubilized in anhydrous CH$_2$Cl$_2$ (30 mL) under argon atmosphere, N,N-diisopropylethylamine (DIEA) (0.066 mL, 0.38 mmol). The obtained limpid orange mixture was stirred at 0° C. for 10 min, and then, 1-(3-dimethylaminopropyl)-3-ethylcarbodimide hydrochloride (EDC☐HCl) (73 mg, 0.38 mmol) was added. After 20 min, 1-hydroxybenzotriazole monohydrate (HOBt H$_2$O) (66 mg, 0.38) was added followed by a slow addition, through a dropping funnel, of the benzidine (70 mg, 0.38 mmol) previously solubilized in CH$_2$Cl$_2$ (30 mL). The reaction mixture was stirred at room temperature for 24 h. The reaction progress was monitored by TLC (silica gel; CHCl$_3$/MeOH=9:1) and ESI-MS, verifying the product formation. The solvent was removed under reduced pressure and the product was isolated by column chromatography (silica gel; CHCl$_3$/MeOH=9:1). A red oil was isolated (94 mg, 60% yield). $^1$H NMR (500 MHz, DMSO-d$_6$, δ): 9.90 (bs, 1H, NH: exchange with D$_2$O); 8.49 (d, 1H, aromatic proton); 7.69-7.52 (m, 2H, aromatic protons); 7.52-7.35 (m, 2H, aromatic protons); 7.35-7.08 (m, 7H, 4 aromatic protons and 3 amine protons); 6.49 (d, 1H, aromatic proton); 3.63-3.39 (m, 2H, NHCH$_2$); 2.53-2.12 (m, 2H, CH$_2$); 1.75-1.46 (m, 6H, CH$_2$CH$_2$CH$_2$). ESI-MS m/z (%): C$_{24}$H$_{24}$N$_6$O$_4$ (M−H)$^+$: 459; (M+Na)$^+$: 483.

N-[4'-Amino-(1,1'-biphenyl)-4-yl]-12-[(7-nitrobenzo[c][1,2,5]oxadiazol-4-il)amino]dodecanamide (n=11). A red oil was isolated (139 mg, 75% yield). $^1$H NMR (500 MHz, DMSO-d$_6$, δ): 9.90 (bs, 1H, NH: exchange with D$_2$O); 8.58 (d, 1H, aromatic proton); 7.77-7.48 (m, 4H, benzidine aromatic protons); 7.23-7.10 (m, 7H, 4 aromatic protons and 3 amine protons); 6.47-6.30 (d, 1H, aromatic proton); 2.38-2.16 (m, 2H, CH$_2$); 1.71-1.47 (m, 4H, CH$_2$CH$_2$); 1.44-1.01 (m, 16H, 8CH$_2$). ESI-MS m/z (%): C$_{30}$H$_{36}$N$_6$O$_4$ (M−H)$^+$: 543; (M+Na)$^+$: 567.

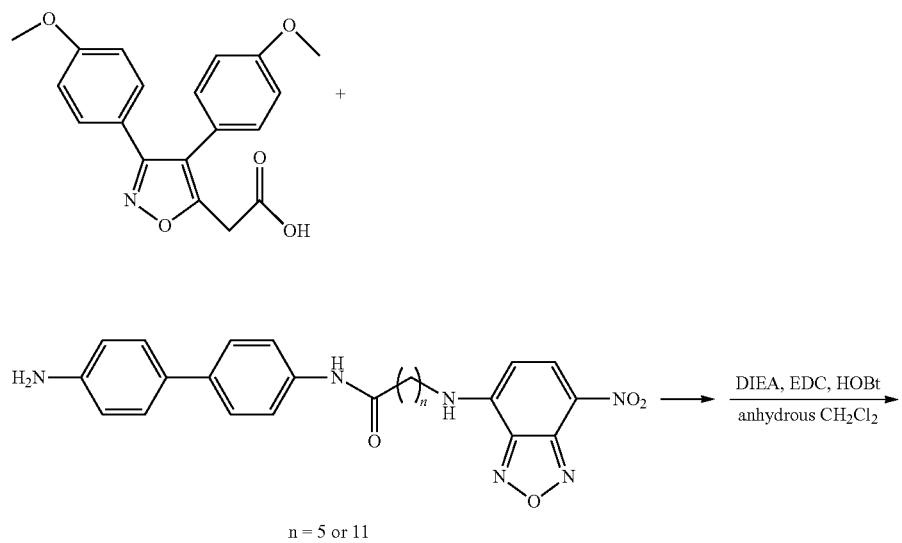

n = 5 or 11

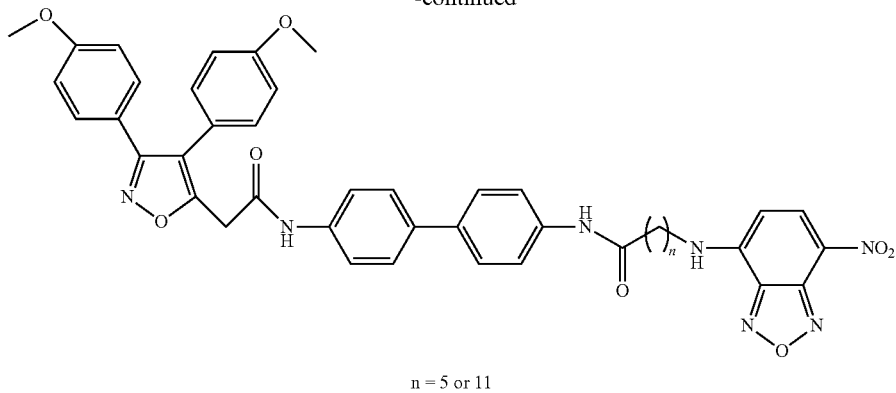

n = 5 or 11

To a limpid orange mofezolac (69 mg, 0.20 mmol) solution in anhydrous $CH_2Cl_2$ (10 mL), under argon atmosphere and stirred at 0° C., 1-(3-dimethylaminopropyl)-3-ethylcarbodimide hydrochloride (EDC HCl) (58 mg, 0.30 mmol) was added. After 20 min, 1-hydroxybenzotriazole monohydrate (HOBt $H_2O$) (52 mg, 0.204) was added followed by a slow addition, through a dropping funnel, of the N-[4'-amino-(1,1'-biphenyl)-4-yl]-6-[(7-nitrobenzo[c][1,2,5]oxadiazol-4-yl)amino]hexanamide (94 mg, 0.20 mmol) [or N-[4'-amino-(1,1'-biphenyl)-4-yl]-12-[(7-nitrobenzo[c][1,2,5]oxadiazol-4-yl)amino]dodecanamide] previously solubilized in anhydrous $CH_2Cl_2$ (14 mL) containing N,N-diisopropylethylamine (DIEA) (0.036 mL, 0.21 mmol). The reaction mixture was stirred at room temperature for 46 h. The reaction progress was monitored by TLC (silica gel; $CHCl_3$/MeOH=9:1) and ESI-MS, verifying the product formation. The solvent was removed under reduced pressure and the product was isolated by column chromatography (silica gel; $CHCl_3$/MeOH=9:1).

N-{4'-{2-[3,4-bis(4-methoyphenyl)isoxazol-5-yl]acetamido}-(1,1'-biphenyl)-4-yl}-6-[(7-nitrobenzo[c][1,2,5]oxadiazol-4-yl)amino]hexanamide (n=5). A red solid was isolated (38 mg, 24% yield). M.p. 135-140° C. FT-IR (KBr): 3290, 3063, 2923, 2852, 1661, 1589, 1541, 1444, 1397, 1298, 1250, 1177, 1119, 1022, 833, 738, 617, 595. $^1H$ NMR (500 MHz, DMSO-$d_6$, δ): 9.93 (bs, 1H, NH); 9.53 (bs, 1H, NH); 8.46 (d, 1H, aromatic proton); 7.63-7.62 (m, 8H, aromatic protons, benzidine moiety); 7.32-7.31 (m, 3H, aromatic protons, mofezolac part, and 1 amine proton); 7.20-7.19 (m, 2H, aromatic protons, mofezolac part); 6.98-6.94 (m, 4H, aromatic protons, mofezolac part); 6.40-6.39 (d, 1H, aromatic proton); 3.89 (m, 2H, $CH_2CO$, mofezolac part); 3.75 (s, 6H, $2OCH_3$); 2.61 (m, 2H, $CH_2$); 2.38-2.31 (m, 2H, $CH_2$); 1.73-1.64 (m, 4H, $2CH_2$); 1.43-1.41 (m, 2H, $CH_2$). $^{13}C$ NMR (750 MHz DMSO-$d_6$, δ): 171.66, 167.05, 165.69, 164.26, 160.78, 159.48, 138.86, 138.17, 135.47, 134.66, 131.99, 129.84, 126.91, 126.83, 121.76, 121.34, 120.84, 119.93, 117.25, 114.77, 114.65, 55.66, 40.82, 40.53, 40.26, 39.98, 39.71, 39.43, 39.14, 36.73, 34.29, 27.94, 26.49, 25.19. ESI-MS m/z (%): $C_{43}H_{39}N_7O_8$ (M−H)$^+$: 780; (M+Na)$^+$: 804.

A red solid was isolated (62 mg, 36% yield). M.p. 145-150° C. FT-IR (KBr): 3296, 3069, 2921, 2850, 1663, 1586, 1514, 1445, 1398, 1296, 1250, 1177, 1109, 1021, 833, 738, 617, 595 cm$^{-1}$. $^1H$ NMR (500 MHz, DMSO-$d_6$, δ): 9.90 (bs, 1H, NH); 9.52 (bs, 1H, NH); 8.50 (d, 1H, aromatic proton); 7.64-7.58 (m, 8H, aromatic protons, benzidine moiety); 7.31 (m, 3H, aromatic protons, mofezolac par, and 1 amine proton); 7.20 (m, 2H, aromatic protons, mofezolac part); 6.99-6.96 (m, 4H, aromatic protons, mofezolac part); 6.40-6.39 (d, 1H, aromatic proton); 3.89 (m, 2H, $CH_2CO$, mofezolac part); 3.76 (s, 6H, $2OCH_3$); 2.30-2.29 (m, 2H, $CH_2$); 1.66-1.58 (m, 4H, $2CH_2$); 1.27-1.25 (m, 16H, $8CH_2$). $^{13}C$ NMR (750 MHz DMSO-$d_6$, δ): 171.7, 165.7, 164.2, 160.7, 160.6, 159.4, 145.6, 144.8, 144.6, 138.9, 138.4, 138.1, 135.3, 134.5, 131.3, 129.8, 126.9, 126.8, 126.7, 121.7, 121.2, 120.9, 120.0, 119.8, 117.2, 114.7, 114.6, 99.9, 99.5, 55.6, 55.5, 43.8, 40.4, 40.3, 40.2, 40.0, 39.9, 39.7, 39.6, 39.5, 38.6, 34.2, 29.3, 29.2, 29.1, 29.0, 28.0, 26.8, 25.5. ESI-MS: m/z (%): $C_{49}H_{51}N_7O_8$ (M−H)$^+$: 864.

2.2 Synthesis of N-[4-(9-dimethylimino-9H-benzo[a]phenoxazin-5-ylamino)butyl]-2-(3,4-bis(4-methoxyphenyl)isoxazol-5-yl)acetamide chloride

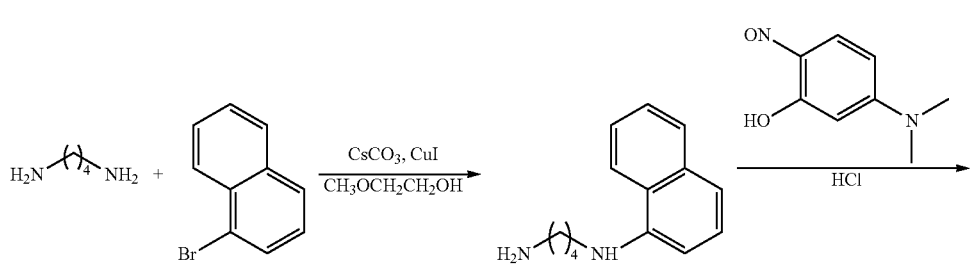

-continued

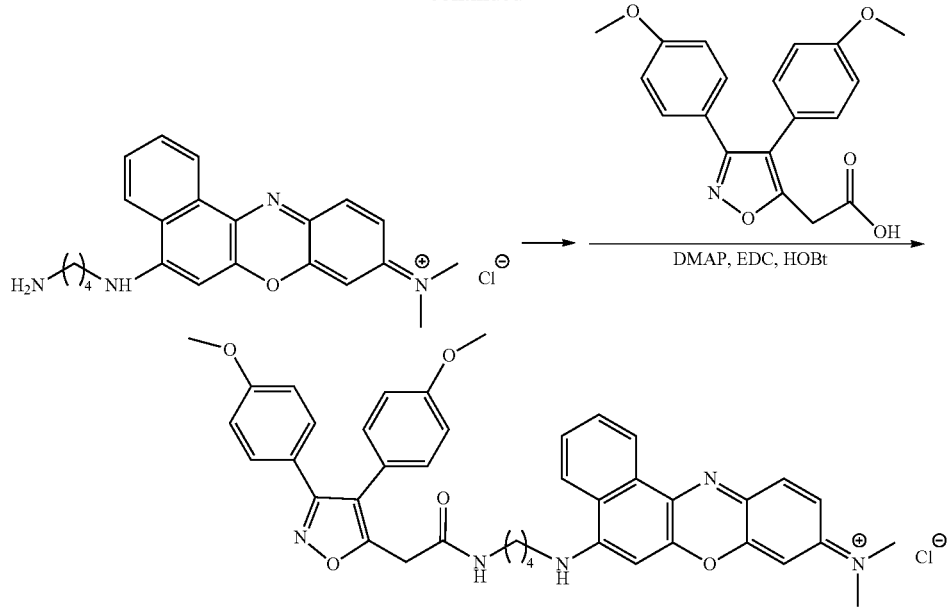

N-(4-Aminobutyl)naphthalen-1-amine. To a solution of 1-bromonaphthalene (1.0 g, 4.83 mmol, 0.67 mL) and 1,4-diaminoobutane (1.13 g, 12.84 mmol) in 2-methoxyethanol (10 mL) CuI (46 mg, 0.24 mmol) and $Cs_2CO_3$ (730 mg, 2.24 mmol) were added. The reaction mixture was refluxed at 125° C. for 24 h. After cooling to room temperature, the mixture was filtered and the yellow filtrate was concentrated under reduced pressure. The crude product, as a black semisolid, was extracted with hot hexane for three times. After the evaporation of the solvent under reduced pressure, the product was isolated as a yellow oil (0.63 g, 61% yield) by column chromatography (silica gel; mobile phase: first $CH_2Cl_2$ and then $CH_2Cl_2/CH_3OH=7:3$). Mp 184-187° C. $^1H$ NMR (500 MHz, $CDCl_3$, δ): 7.83-7.79 (m, 2H, aromatic protons); 7.49-7.41 (m, 2H, aromatic protons); 7.35 (t, 1H, J=7.83 Hz, aromatic proton); 7.23 (d, 1H, J=9.68 Hz, aromatic proton); 6.61 (d, 1H, J=7.34 Hz, aromatic proton); 3.80-3.72 (m, 1H, NH: exchanged with $D_2O$); 3.31 (t, 2H, J=7.10 Hz, $NHCH_2$); 2.81 (t, 2H, J=7.10 Hz, $CH_2NH_2$); 1.89-1.81 (m, 2H, $CH_2CH_2NH_2$); 1.69-1.63 (m, 2H, $NHCH_2CH_2$); 1.88-1.40 (bs, 2H, $NH_2$: exchanged with $D_2O$). ESI-MS m/z (%): $C_{14}H_{18}N_2$ $(M+H)^+$: 215; ESI-MS-MS (215): 198 (78), 72 (100).

N-(4-aminobutyl)-9-dimethylimino-9H-benzo[a]phenoxazin-5-amonium chloride. To an ice-bath cold solution of N-(4-aminobutyl)naphthalen-1-amine (630 mg, 2.94 mmol) in ethanol (20 mL) 5-(dimethylamino)-2-nitrosophenol (503 mg, 3.0 mmol) and conc. HCl (0.92 mL) were added. The reaction mixture was stirred at 0° C. for 10 minutes, then heated at 90° C. for 2.5 h. Then, the reaction mixture was allowed to reach room temperature. The solvent was removed under reduced pressure to give a violet solid (677 mg, 64% yield). Mp 184-187° C. $^1H$ NMR (500 MHz, $CDCl_3$, δ): 8.63 (d, 1H, J=7.83 Hz, aromatic proton); 8.37 (d, 1H, J=5.90 Hz, aromatic proton); 7.83 (t, 1H, J=6.25 Hz, aromatic proton); 7.74 (t, 1H, J=6.25 Hz, aromatic proton); 7.67-7.62 (m, 1H, aromatic proton); 7.15-7.10 (m, 1H, aromatic proton); 6.88 (s, 1H, aromatic proton); 6.65 (s, 1H, aromatic proton); 3.70 (t, 3H, J=7.10 Hz, $NHCH_2$); 3.25 (s, 6H, $(CH_3)_2N^+$); 3.08 (t, 2H, J=7.30 Hz, $CH_2NH_2$); 1.88-2.05 (m, 4H, $NHCH_2(CH_2)_2CH_2NH_2$); 1.88-1.40 (bs, 2H, $NH_2$: exchanged with $D_2O$). $^{13}C$ NMR (500 MHz, $CDCl_3$, δ): 157.87, 155.78, 151.56, 147.60, 133.44, 132.25, 131.62, 130.85, 130.03, 129.56, 124.06, 123.18, 122.87, 115.24, 95.65, 93.27, 48.22, 48.10, 48.05, 47.93, 47.88, 47.76, 47.71, 47.60, 47.53, 47.47, 47.42, 47.25, 47.08, 43.67, 39.81, 38.97, 25.25, 24.65; ESI-MS m/z (%): $C_{22}H_{24}ClN_4O$ $(M+H)^+$: 361; ESI-MS-MS (361): 290 (100).

N-[4-(9-dimethylimino-9H-benzo[a]phenoxazin-5-ylamino) butyl]-2-(3,4-bis(4-methoxyphenyl) isoxazol-5-yl) acetamide chloride. To a solution of N-(4-aminobutyl)-9-dimethylimino-9H-benzo[a]phenoxazin-5-amonium chloride (56 mg, 0.155 mmol) in anhydrous DMF (5 mL), mofezolac (53 mg, 0.155 mmol), 1-(3-dimethylaminopropyl)-3-ethylcarbodiimide hydrochloride (EDC) (39 mg, 0.20 mg), HOBt·$H_2O$ (35 mg, 0.20 mmol) and 4-dimethylaminopyridine (DMAP) (25 mg, 0.20 mmol) were added. The mixture was stirred at room temperature, under nitrogen atmosphere, for 24 h. Then, the solvent was removed under reduced pressure and a violet solid (34 mg, 31% yield) was isolated by chromatography (silica gel; $CH_2Cl_2/CH_3OH=9$: 1). Mp 142-144° C. FT-IR (KBr): 3427, 3235, 3063, 2921, 2851, 1641, 1588, 1328, 835, 717 $cm^{-1}$. $^1H$ NMR (500 MHz, $CDCl_3$, δ): 9.00-8.85 (bs, 1H, NH: exchange with $D_2O$); 8.80 (d, 1H, J=8.30 Hz, aromatic proton); 8.31 (d, 1H, J=8.30 Hz, aromatic proton); 7.90 (t, 1H, J=7.60 Hz, aromatic proton); 7.80 (t, 1H, J=7.80 Hz, aromatic proton); 7.70 (d, 1H, J=9.30 Hz, aromatic proton); 7.14-7.04 (m, 5H, aromatic protons); 6.92 (s, 1H, aromatic proton); 6.80 (d, 2H, J=8.80 Hz, aromatic protons); 6.70 (d, 2H, J=9.30 Hz, aromatic protons); 6.60 (s, 1H, aromatic proton); 3.80-3.74 (m, 6H, $OCH_3$, and $ArNHCH_2$); 3.72 (s, 3H $OCH_3$); 3.69 (s, 2H, $CH_2CONH$); 3.40 (t, 2H, J=6.40 Hz, $CH_2NHCO$); 3.20 (s, 6H, $(CH_3)_2N^+$); 1.92-1.88 (m, 2H, $ArNHCH_2CH_2$); 1.79-1.76 (m, 2H, $CONHCH_2CH_2$). ESI-MS m/z (%): $C_{41}H_{39}ClN_5O_5$ $[M+H-Cl]^+$: 682.5; ESI-MS-MS: 682.5: 361 (100), 290.

2.3 Synthesis of P6-COOH or Mofezolac Conjugated with Rhodamine by 1,4-diaminobutane

2.3.1 Synthesis of N-(9-{2-[(4-{2-[3-(5-chloro-furan-2-yl)-4-phenylisoxazol-5-yl]acetamido}butyl)carbamoyl] phenyl-6-(ethylamino)-2,7-dimethyl-3H-xanthen-3-ylidene}ethanaminium chloride

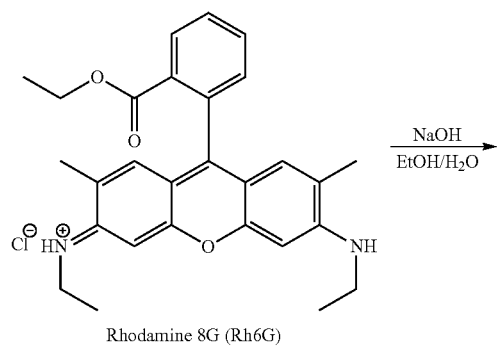

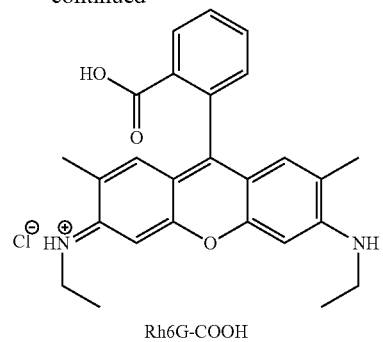

N-[9-(2-carboxyphenyl)-6-(ethylamino)-2,7-dimethyl-3H-xanthen-3-ylidene]ethanaminium (Rh6G-COOH). A solution of NaOH (75.6 mg, 1.89 mmol) in $H_2O$ (60 mL) was added to a stirred solution of rhodamine 6G (500 mg, 1.04 mmol) in absolute EtOH (50 mL) at room temperature. The reaction mixture was refluxed overnight. Then the EtOH was evaporated under reduced pressure and 37% HCl was added till acidic pH. The product was isolated after filtration as a pink solid (258 mg, 55% yield). $^1$H NMR (300 MHz, acetone-$d_6$, δ): 7.91 (d, 1H, J=7.6 Hz, aromatic proton); 7.75-7.59 (m, 2H, aromatic protons); 7.17 (d, 1H, J=7.6 Hz, aromatic proton); 6.36 (s, 2H, aromatic protons); 6.33 (s, 2H, aromatic protons); 4.67 (bs, 1H, NH: exchanges with $D_2O$); 3.24 (q, 4H, J=7.2 Hz, 2 $NCH_2CH_3$); 1.93 (s, 6H, 2 $ArCH_3$); 1.27 (t, 6H, J=7.2 Hz, 2 $NCH_2CH_3$); FT-IR (KBr): 3415, 2924, 1608, 1530, 1501, 1365, 1307, 1187, 1016, 793 cm-1; ESI-MS (m/z): $C_{26}H_{27}N_3O_3$ ($M^+$): 415; $(M+Na)^+$: 437.

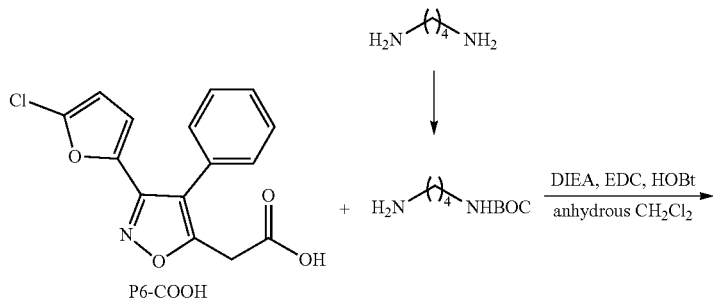

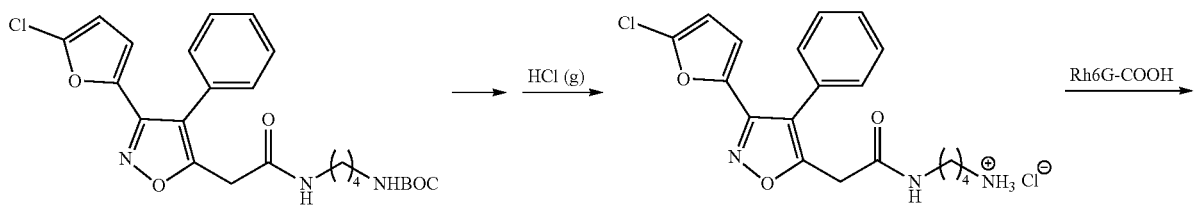

-continued

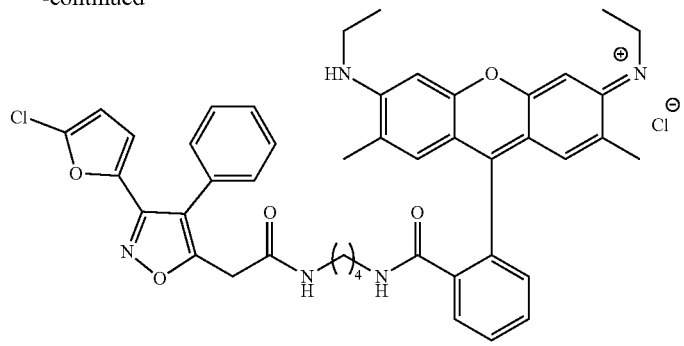

t-Butyl (4-{2-[3-(5-chlorofuran-2-yl)-4-phenylisoxazol-5-yl]acetamido}butyl)carbamate. To a solution of P6-COOH (160 mg, 0.588 mmol) solubilized in DMF (14 mL) and stirred in a nitrogen-flushed, were added tert-butyl (4-aminobutyl)carbamate (320 mg, 1.7 mmol), HOBt (151 mg. 0.81 mmol), DIEA (225 mg, 1.7 mmol), EDC hydrochloride (153 mg, 0.798 mmol). The mixture was stirred at room temperature for 48 h. Then, water was added, and the aqueous solution was extracted with EtOAc. The combined organic layers were washed with brine, dried over anhydrous $Na_2SO_4$, and the solvent was evaporated under reduced pressure. Column chromatography of the crude residue, on a silica gel and $CHCl_3$/MeOH (95:5) as a mobile phase, afforded the target compound as a yellow solid (125 mg, 45% yield). M.p.=126.5-127° C. FT-IR (KBr): 3346, 2941, 1683, 1658, 1539, 1521, 1437, 1366, 1261, 1172, 1019, 941, 892, 787, 699 cm$^{-1}$. $^1$H NMR (300 MHz, $CDCl_3$, δ): 7.48-7.44 (m, 3H, aromatic protons); 7.38-7.35 (m, 2H aromatic protons); 6.30 (d, 1H, J=3.5 Hz, furanyl proton); 6.16 (d, 1H, J=3.5 Hz, furanyl proton); 6.04 (bs, 1H, $CONHCH_2$: exchanges with $D_2O$); 4.58 (s, 1H, NHBoc: exchanges with $D_2O$); 3.66 (s, 2H, isoxazole-$CH_2CO$); 3.27 (q, 2H, J=6.8 Hz, $CONHCH_2$); 3.18-3.10 (m, 2H, $CH_2NHCO$); 1.54-1.48 (m, 4H, $CH_2CH_2$); 1.44 (s, 9H, $C(CH_3)_3$). $^{13}$C NMR (75 MHz, $CDCl_3$, δ): 166.1, 130.2, 129.1, 129.06, 114.4, 108.2, 59.7, 39.9, 38.3, 34.0, 32.1, 31.4, 31.1, 29.9, 29.5, 28.6, 27.8, 22.9, 14.3. ESI-MS (m/z): $C_{24}H_{28}ClN_3O_5$, 496 (M+Na)$^+$.

N-(4-aminobutyl)-2-[3-(5-chlorofuran-2-yl)-4-phenylisoxazol-5-yl]acetamide hydrochloride. Prepared as 4-2-[1-(4-chlorobenzoyl)-5-methoxy-2-methyl-1Hindol-3-yl]acetamidobutan-1-aminium chloride (4) (quantitative yield) using as a reagent the t-butyl(4-2-[3-(5-chlorofuran-2-yl)-4-phenylisoxazol-5-yl]acetamidobutyl)carbamate (2). FT-IR (KBr): 3405, 1633, 1266, 1134, 1017, 793 cm-1. 1H NMR (300 MHz, DMSO-$d_6$, δ): 8.50-8.40 (m, 1H, $CONHCH_2$: exchanges with $D_2O$); 8.14 (bs, 3H, $NH_3^+$: exchange with $D_2O$); 7.46-7.38 (m, 2H, aromatic protons); 7.36-7.30 (m, 3H, aromatic protons); 6.54 (d, 1H, J=3.5 Hz, furanyl proton); 6.38 (d, 1H, J=3.5 Hz, furanyl proton); 4.60 (m, 1H, $CONHCH_2$: exchanges with $D_2O$); 3.61 (s, 2H, $CH_2CO$); 3.20-2.96 (m, 2H, $CH_2NH_3^+$); 2.74-2.64 (m, 2H, $CONHCH_2$); 1.54-1.36 (m, 4H, $CH_2CH_2$). $^{13}$C NMR (75 MHz, DMSO-$d_6$, δ): 166.6, 165.9, 165.4, 152.4, 143.6, 137.6, 130.4, 130.2, 129.4, 129.2, 128.9, 116.8, 114.8, 109.5, 94.6, 70.4, 63.5, 38.9, 33.2, 26.5, 25.0. ESI-MS (m/z): $C_{19}H_{20}N_3O_3Cl$, 374 (M+H)$^+$.

N-(9-{2-[(4-{2-[3-(5-chlorofuran-2-yl)-4-phenylisoxazol-5-yl]acetamido}butyl)carbamoyl]phenyl-6-(ethylamino)-2,7-dimethyl-3H-xanthen-3-ylidene}ethanaminium chloride. To a stirred solution of N-[9-(2-carboxyphenyl)-6-(ethylamino)-2,7-dimethyl-3H-xanthen-3-ylidene]ethanaminium (77 mg, 0.158 mmol) in DMF (6 mL) were added EDC hydrochloride (30 mg, 0.158 mmol), HOBt (31.5 mg, 0.206 mmol), DIEA (114 mg, 0.735 mmol) and N-(4-aminobutyl)-2-[3-(5-chlorofuran-2-yl)-4-phenylisoxazol-5-yl]acetamide hydrochloride (5) (60 mg, 0.147 mmol). After, the reaction mixture was stirred overnight at room temperature. Then, the solvent was removed under reduced pressure. Column chromatography of the crude residue on a silica gel and Hexane/EtOAc (1:1) followed by $CHCl_3$/MeOH (95:5) as a mobile phase afforded the target compound as a brown oil (18 mg, 15% yield). $^1$H NMR (300 MHz, $CDCl_3$, δ): 7.82-7.79 (m, 1H, aromatic proton); 7.41-7.35 (m, 5H, aromatic protons); 7.04-6.96 (m, 1H, aromatic proton); 6.72-6.64 (bs, 1H, $CONHCH_2$: exchanges with $D_2O$); 6.31 (s, 2H, aromatic protons); 6.22 (d, 1H, J=2.8 Hz, furanyl proton); 6.18 (s, 2H, aromatic proton); 6.10 (d, 1H, J=2.8 Hz, furanyl proton); 3.61 (s, 2H, $CH_2CO$); 3.60-3.40 (bs, 2H, 2 $NHCH_2CH_3$: exchange with $D_2O$); 3.17 (q, 4H, J=7.1 Hz, 2 $NHCH_2CH_3$); 3.10-3.04 (m, 4H, $CH_2(CH_2)_2CH_2$); 1.87 (s, 6H, 2 $ArCH_3$); 1.30-1.22 (m, 10H, 2 $NHCH_2CH_3$ and $(CH_2)$ $2CH_2CH_2$ and $CH_2CH_2(CH_2)_2$). $^{13}$C NMR (100 MHz, $CDCl_3$, δ): 168.5, 166.0, 163.7, 162.5, 153.6, 152.4, 151.6, 147.4, 143.3, 138.5, 132.4, 131.0, 130.0, 128.8, 128.6, 128.57, 128.47, 128.0, 123.7, 122.6, 117.9, 116.9, 113.9, 107.9, 106.0, 96.5, 65.1, 39.6, 39.2, 38.3, 33.5, 29.7, 25.9, 25.2, 16.6, 14.7. ESI-MS m/z (%): $C_{45}H_{44}ClN_5O_5$ (M+Na)$^+$: 792.

2.3.2 N-(9-{2-[(4-{2-[3,4-bis(4-methoxyphenyl)isoxazol-5yl]acetamido}butyl)carbamoyl]phenyl}-6-(ethylamino)-2,7-dimethyl-3H-xanthen-3-ylidene) ethanaminium chloride

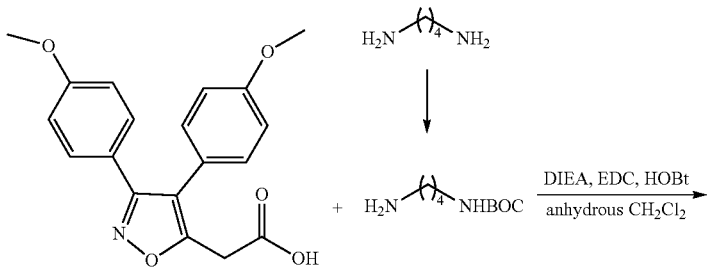

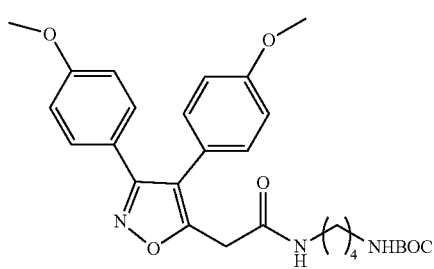

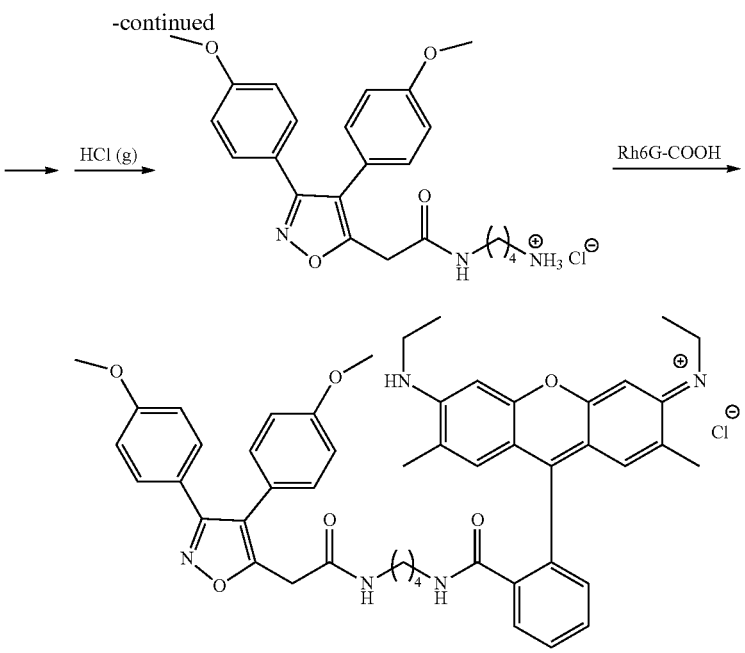

t-Butyl (4-{2-[3,4-bis(4-methoxyphenyl)isoxazol-5yl] acetamido}butyl)carbamate. To a solution of mofezolac (300 mg, 0.88 mmol) solubilized in dry DMF (15 mL), stirred in a nitrogen-flushed, three necked flask equipped with a magnetic stirrer, nitrogen inlet and two dropping funnels, were added t-butyl (4-aminobutyl)carbamate (478 mg, 2.54 mmol), HOBt monohydrate (205 mg, 1.20 mmol), dry DIEA (328 mg, 2.54 mmol), EDC hydrochloride (229 mg, 1.20 mmol). The mixture was stirred at room temperature for 48 h. Then, water was added, and the aqueous solution was extracted with EtOAc. The combined organic layers were washed with brine to further removal of the residual DMF, dried over anhydrous $Na_2SO_4$, and the solvent was distilled under reduced pressure. The product was isolated as a yellow solid (184 mg, 41% yield) by column chromatography (silica gel, $CHCl_3$/MeOH=95:5). $^1$H NMR (300 MHz, $CDCl_3$, δ): 7.38 (d, 2H, J=8.9 Hz, aromatic protons); 7.16 (d, 2H, J=8.8 Hz, aromatic protons); 6.90 (d, 2H, J=8.8 Hz, aromatic protons); 6.84 (d, 2H, J=8.9 Hz, aromatic protons); 6.09 (bs, 1H, NH: exchanges with $D_2O$); 4.60 (bs, 1H, NH: exchanges with $D_2O$); 3.83 (s, 3H, $OCH_3$); 3.80 (s, 3H, $OCH_3$); 3.68 (s, 2H, $ArCH_2CON$); 3.28 (q, 2H J=6.3 Hz, $NHCH_2$); 3.15-3.05 (m, 2H, $CH_2NH$); 1.54-1.53 (m, 4H, $CCH_2CH_2C$) 1.43 (s, 9H, $C(CH_3)_3$). $^{13}$C NMR (75 MHz, $CDCl_3$, δ): 166.8, 162.9, 161.4, 160.8, 159.7, 156.3, 131.3, 130.0, 121.6, 121.2, 117.7, 114.6, 114.2, 79.5, 55.6, 55.4, 40.2, 39.9, 34.4, 29.9, 28.6, 27.8, 27.6, 26.7. ESI-MS m/z (%): $C_{28}H_{35}N_3O_6$ (M+Na)$^+$: 532.4.

N-(4-Aminobutyl)-2-(3,4-bis(4-methoxyphenyl)isoxazol-5-yl)acetamide hydrochloride. Dry HCl (obtained by dripping 37% HCl in conc. $H_2SO_4$) was bubbled in a solution of t-butyl (4-2-[3,4-bis(4-methoxyphenyl)isoxazol-5-yl]acetamidobutyl)carbamate (170 mg, 0.33 mmol) in dry $CH_2Cl_2$ (15 mL). After 2 h, the reaction mixture appeared as a suspension. Then, the solvent was evaporated under vacuum, and the product was isolated as a brown solid (quantitative yield), used without any further purification. $^1$H NMR (300 MHz, $CDCl_3$, δ): 7.35 (d, 2H, J=8.80 Hz, aromatic protons); 7.15 (d, 2H, J=8.80 Hz, aromatic protons); 6.88 (d, 2H, J=8.80 Hz, aromatic protons); 6.81 (d, 2H, J=8.80 Hz, aromatic protons); 6.80-6.74 (bs, 1H, NH: exchanges with $D_2O$); 3.80 (s, 3H, $OCH_3$); 3.77 (s, 3H, $OCH_3$); 3.64 (s, 2H, $ArCH_2CON$); 3.25 (q, 2H, J=6.1 Hz, $NHCH_2$); 2.71 (t, 2H, J=6.6 Hz, $CH_2NH_2$); 1.57-1.43 (m, 4H, $CH_2CH_2$). $^{13}$C NMR (75 MHz, $CDCl_3$, δ): 166.9, 163.2, 161.3, 160.8, 159.6, 131.30, 131.27, 130.0, 129.9, 121.6, 121.2, 117.7, 114.5, 114.2, 55.5, 55.4, 41.7, 40.0, 34.3, 30.8, 27.1. ESI-MS m/z (%): $C_{23}H_{27}N_3O_4$ (M+H)$^+$: 410.

N-(9-{2-[(4-{2-[3,4-bis(4-methoxyphenyl)isoxazol-5yl] acetamido}butyl)carbamoyl]phenyl}-6-(ethylamino)-2,7-dimethyl-3H-xanthen-3-ylidene)ethanaminium chloride. To a stirred solution of N-[9-(2-carboxyphenyl)-6-(ethylamino)-2,7-dimethyl-3Hxanthen-3-ylidene]ethanaminium (146 mg, 0.03 mmol) in $CH_2Cl_2$/DMSO (3:1, 22 mL), were added PyBOP (benzotriazol-1-yl-oxytripyrrolidinophosphonium hexafluorophosphate) (338 mg, 0.650 mmol) and triethylamine (379 mg, 3.75 mmol, 0.052 mL). After 2 h, a solution of N-(4-aminobutyl)-2-(3,4-bis(4-methoxyphenyl) isoxazol-5-yl)acetamide (133 mg, 0.3 mmol in $CH_2Cl_2$/ DMSO (3:2, 22 mL) was added dropwise, and the reaction mixture stirred for 24 h at room temperature. Then, the solvent was removed under reduced pressure. Column chromatography of the crude residue on a silica gel and Hexane/ EtOAc (1:1) as a mobile afforded the target compound as a brown oil (21.7 mg, 90% yield). $^1$H NMR (300 MHz, $CDCl_3$, δ): 7.90-7.84 (m, 1H, aromatic proton); 7.46-7.41 (m, 2H, aromatic protons); 7.39-7.32 (m, 2H, aromatic protons); 7.22-7.16 (m, 2H, aromatic protons); 7.07-7.01 (m, 1H, aromatic proton); 6.90-6.80 (m, 3H, aromatic protons); 6.45-6.30 (bs, 2H, 2 NH: exchange with $D_2O$); 6.34 (s, 2H, aromatic protons); 6.21 (s, 2H, aromatic protons); 3.80 (s, 3H, $OCH_3$); 3.79 (s, 3H, $OCH_3$); 3.62 (s, 2H, $ArCH_2NCO$); 3.52 (bs, 2H, 2 $NHCH_2CH_3$: exchange with $D_2O$); 3.23-3.05 (m, 8H, 2 $NHCH_2CH_3$ and $CH_2(CH_2)_2CH_2$); 1.89 (s, 6H, 2 $ArCH_3$); 1.37-1.24 [m, 8H, 2$NHCH_2CH_3$ and $(CH_2)$ 2$CH_2CH_2$]; $_{1.14}$-1.05 (m, 2H, $CH_2CH_2(CH_2)_2$). $^{13}$C NMR (75 MHz, $CDCl_3$, δ): 168.7, 166.8, 163.2, 161.2, 160.7, 159.6, 153.8, 151.9, 147.6, 132.7, 131.4, 130.0, 128.8, 128.7, 128.3, 124.0, 122.9, 121.9, 121.5, 118.1, 117.7, 114.5, 114.1, 106.3, 96.8, 96.7, 65.3, 55.5, 55.4, 42.9, 39.9, 39.6, 34.2, 26.0, 25.8, 16.9, 14.9; FT-IR (neat): 3429, 3330, 3051, 2963, 2923, 2854, 1675, 1621, 1517, 1468, 1322, 1262, 1218, 1149, 1090, 1016, 925, 879, 801, 743, 693 cm-1. ESI-MS m/z (%): $C_{49}H_{51}N_5O_6$ (M+Na)$^+$: 828.

3. Synthesis of Mofezolac-LK-Mofezolac (Mof-LK-Mof) and Mofezolac-LK-Arachidonic Acid (Mof-LK-AA) Compounds 3.1 General Procedure for the Preparation of Mofezolac-LK-Mofezolac Compounds (Mof-LK-Mof)

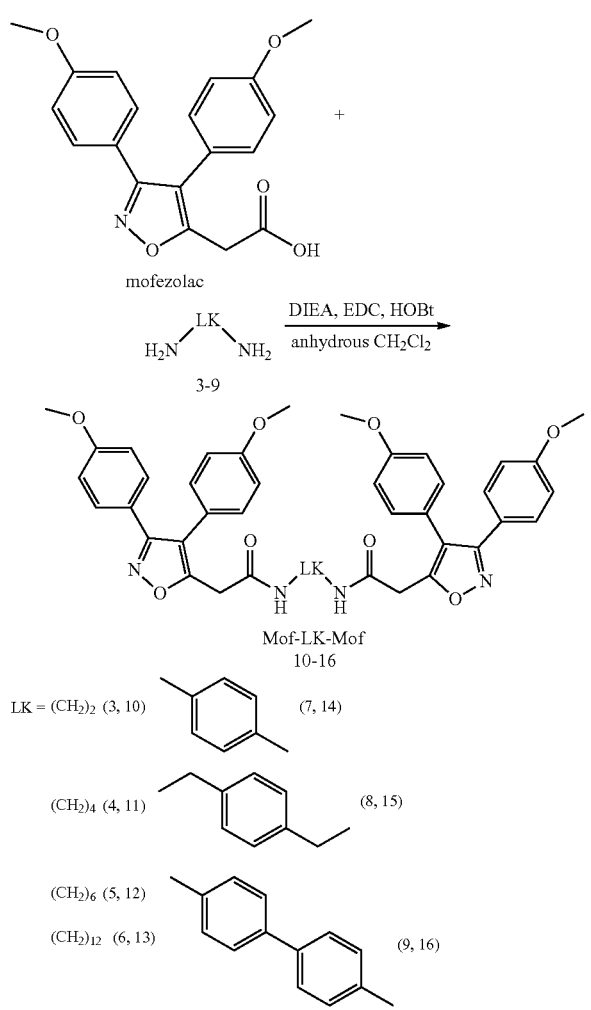

Mofezolac (3 mmol) was solubilized in anhydrous $CH_2Cl_2$ contained in an argon-flushed three-necked round bottom flask, equipped with a magnetic stirrer and an argon inlet. The resulting mixture, kept under argon atmosphere, was cold to 0° C. by an ice-bath. Then, 1-hydroxybenzotriazole monohydrate (HOBt, 3 mmol)) and 1-(3-dimethylaminopropyl)-3-ethylcarbodiimide hydrochloride (EDC, 3 mmol) were added. The yellow and limpid reaction mixture was stirred for 2 h at 0° C. Then, the proper diamine (3-9, 1 mmol) and N,N-diisopropylethylamine (DIEA, 3 mmol) were very slowly added by a syringe. Such a reaction mixture was stirred for 16 h (overnight). The reaction progress was monitored by TLC (silica gel; $CHCl_3$/MeOH=9:1). The reaction was blocked by adding $H_2O$ and the formed product together with the not reacted mofezolac were extracted by EtOAc (three times). The organic extracts were treated with $NaHCO_3$ saturated aq. solution and extracted by EtOAc (three times) to remove the not reacted mofezolac. 3N HCl was added to the aqueous phase till pH<6, and then extracted three times with EtOAc to recover the not reacted mofezolac. The combined organic extracts, contained the reaction product, were dried with anhydrous $Na_2SO_4$, filtered and the solvent removed under reduced pressure. A solid was obtained (10-16).

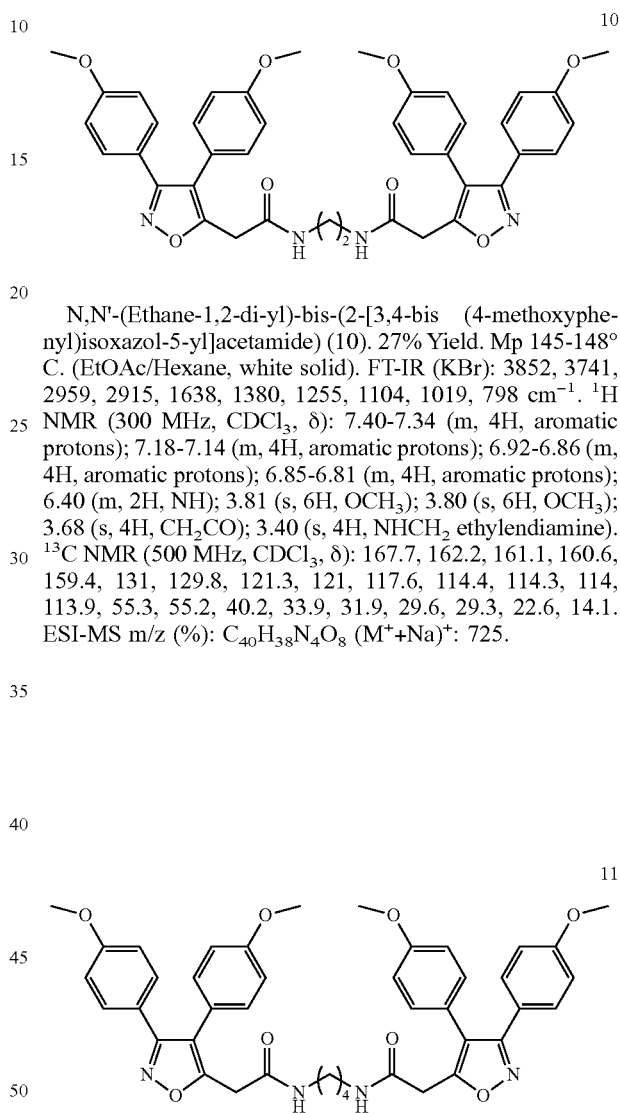

N,N'-(Ethane-1,2-di-yl)-bis-(2-[3,4-bis (4-methoxyphenyl)isoxazol-5-yl]acetamide) (10). 27% Yield. Mp 145-148° C. (EtOAc/Hexane, white solid). FT-IR (KBr): 3852, 3741, 2959, 2915, 1638, 1380, 1255, 1104, 1019, 798 cm$^{-1}$. $^1$H NMR (300 MHz, CDCl$_3$, δ): 7.40-7.34 (m, 4H, aromatic protons); 7.18-7.14 (m, 4H, aromatic protons); 6.92-6.86 (m, 4H, aromatic protons); 6.85-6.81 (m, 4H, aromatic protons); 6.40 (m, 2H, NH); 3.81 (s, 6H, OCH$_3$); 3.80 (s, 6H, OCH$_3$); 3.68 (s, 4H, CH$_2$CO); 3.40 (s, 4H, NHCH$_2$ ethylendiamine). $^{13}$C NMR (500 MHz, CDCl$_3$, δ): 167.7, 162.2, 161.1, 160.6, 159.4, 131, 129.8, 121.3, 121, 117.6, 114.4, 114.3, 114, 113.9, 55.3, 55.2, 40.2, 33.9, 31.9, 29.6, 29.3, 22.6, 14.1. ESI-MS m/z (%): $C_{40}H_{38}N_4O_8$ (M$^+$+Na)$^+$: 725.

N-(4-(2-(3,4-Bis(4-methoxyphenyl)isoxazol-5-yl)acetamido)butyl)-3,4-bis(4-methoxyphenyl)isoxazole-5-carboxyamide (11). 83% Yield. Mp 163-166° C. (EtOAc/Hexane, white solid). FT-IR (KBr): 3836, 3736, 3294, 2930, 1647, 1384, 1287, 1256, 1178, 1097, 1031, 1019, 826, 802 cm$^{-1}$. $^1$H NMR (300 MHz, CDCl$_3$, δ): 7.40-7.34 (m, 4H, aromatic protons); 7.19-7.13 (m, 4H, aromatic protons); 6.93-6.88 (m, 4H, aromatic protons); 6.85-6.82 (m, 4H, aromatic protons); 6.10 (m, 2H, NH); 3.82 (s, 6H, OCH$_3$); 3.80 (s, 6H, OCH$_3$); 3.67 (s, 4H, CH$_2$CO); 3.29-3.27 (m, 4H, NHCH$_2$); 1.53-1.49 (m, 4H, CH$_2$CH$_2$). $^{13}$C NMR (75 MHz, CDCl$_3$, δ): 167.0, 162.9, 161.3, 160.8, 159.6, 131.3, 130, 121.6, 121.2, 117.7, 114.5, 115.2, 55.5, 55.4, 39.6, 34.3, 29.9, 26.8, 1.2. ESI-MS m/z (%): $C_{42}H_{42}N_4O_8$ (M-H$^+$)$^+$: 729.

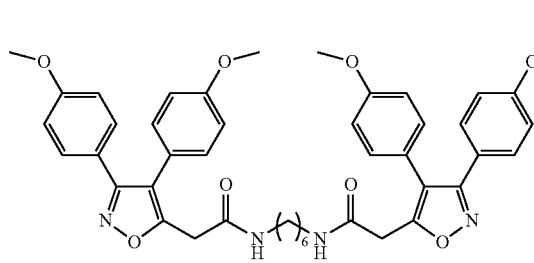

12

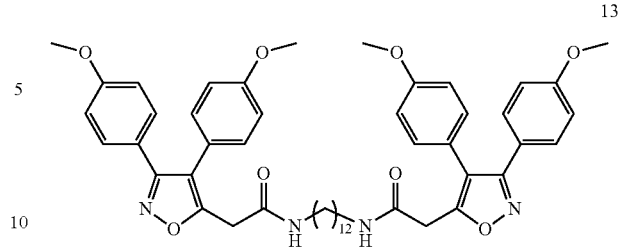

13

N-(4-(2-(3,4-Bis(4-methoxyphenyl)isoxazol-5-yl)acetamido)hexyl)-3,4-bis(4-methoxyphenyl)isoxazole-5-carboxyamide (12). The product was isolated by column chromatography (silica gel; CHCl$_3$/MeOH=11:1). Mp 159-161° C. (yellow solid). 20% Yield. FT-IR (KBr): 3834, 3733, 2924, 1644, 1509, 1384, 1259, 1174, 1100, 1031, 800 cm$^{-1}$. $^1$H NMR (500 MHz, CDCl$_3$, δ): 7.40-7.38 (m, 4H, aromatic protons); 7.18-7.16 (m, 4H, aromatic protons); 6.92-6.90 (m, 4H, aromatic protons); 6.86-6.84 (m, 4H, aromatic protons); 6.25 (m, 2H, NH); 3.83 (s, 6H, OCH$_3$); 3.81 (s, 6H, OCH$_3$); 3.67 (s, 4H, CH$_2$CO); 3.29-3.25 (q, 4H, NHCH$_2$); 1.52-1.49 (m, 4H, NHCH$_2$CH$_2$); 1.33-1.31 (m, 4H, NHCH$_2$CH$_2$). ESI-MS m/z (%): C$_{44}$H$_{46}$N$_4$O$_8$ (M+Na)$^+$: 781.

N-(4-(2-(3,4-Bis(4-methoxyphenyl)isoxazol-5-yl)acetamido)dodecyl)-3,4-bis(4-methoxyphenyl)isoxazole-5-carboxyamide (13). The product was isolated by column chromatography (silica gel; CHCl$_3$/MeOH=15:1). Mp 134-138° C. (yellow solid). 67% Yield. FT-IR (KBr): 3715, 3600, 2929, 2863, 1646, 1609, 1553, 1513, 1428, 1251, 1177, 1037, 831 cm$^{-1}$. $^1$H NMR (500 MHz, CDCl$_3$, δ): 7.41-7.39 (m, 4H, aromatic protons); 7.17-7.15 (m, 4H aromatic protons); 6.93-6.91 (m, 4H, aromatic protons); 6.87-6.84 (m, 4H, aromatic protons); 3.84 (s, 4H, CH$_2$CO); 3.29-3.24 (m, 4H, NHCH$_2$CH$_2$); 1.57-1.30 (m, 4H, NH—CH$_2$CH$_2$); 1.28-1.24 (m, 16H, CH$_2$ dodecandiamine). $^{13}$C NMR (300 MHz, CDCl$_3$, δ): 116.4, 162.7, 161.1, 160.6, 159.4, 131, 129.7, 121.3, 120, 117.4, 114.3, 113.9, 55.2, 40, 34.2, 29.3, 29.1, 26.7. ESI-MS m/z (%): C$_{50}$H$_{58}$N$_4$O$_8$ (M$^+$+Na)$^+$: 865.

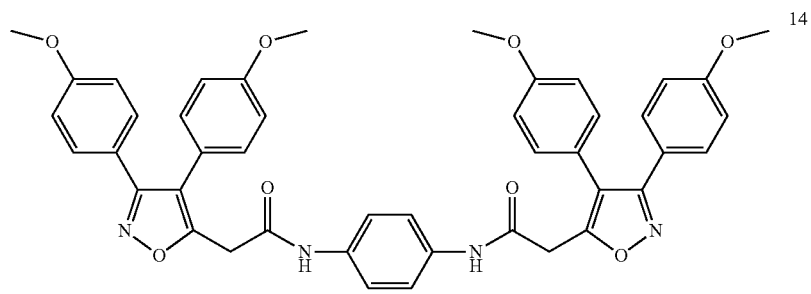

14

2-(3,4-Bis(4-mehoxyphenyl)isoxazol-5-yl)-N-(4-(3-(3,4-bis(4-methoxyphenyl)isoxazol-5-yl)-2-oxopropylamino)phenyl)acetamide (14). The product was isolated by column chromatography (silica gel; CHCl$_3$/MeOH=15:1). Mp 178-182° C. (pink solid). 45% Yield. FT-IR (KBr): 3749, 3653, 2915, 1639, 1384, 1251, 1107 cm$^{-1}$. $^1$H MNR (500 MHz, MeOH-d$_4$, δ): 7.50-7.49 (m, 4H, aromatic protons); 7.37-7.33 (m, 4H, aromatic protons); 7.21-7.19 (m, 4H, aromatic protons); 6.95-6.92 (m, 4H, aromatic protons); 6.90-6.87 (m, 4H, aromatic protons); 6.18 (s, 2H, NH); 3.87 (s, 6H, OCH$_3$); 3.86 (s, 6H, OCH$_3$); 3.81 (s, 4H, CH$_2$CO). ESI-MS m/z (%): C$_{44}$H$_{38}$N$_4$O$_8$ (M−H)$^+$: 749.

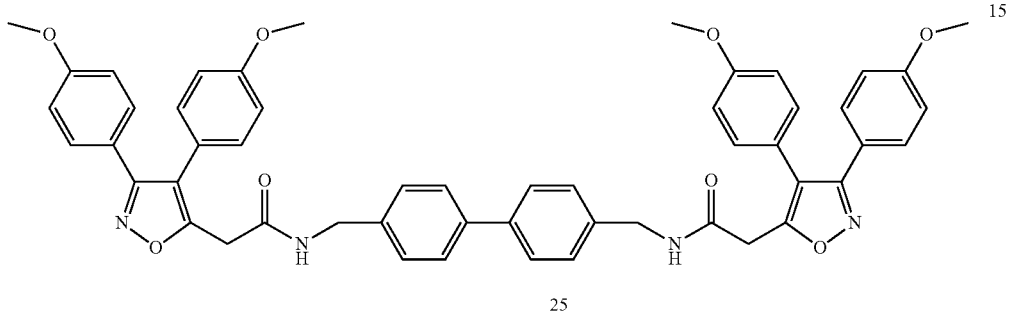

2-(3,4-Bis(4-methoxyphenyl)isoxazol-5-yl)-N-(4-((3-(3,4-bis(4-methoxyphenyl)isoxazol-5-yl)-2-oxopropylamino)methyl)benzyl)acetamide (15). The product was isolated by column chromatography (gel di silice; CHCl$_3$/MeOH=15:1). Mp: 168-172° C. (white solid). 26% Yield. $^1$H NMR (500 MHz, DMSO-d$_6$, δ): 8.69-8.68 (m, 2H, OCNH); 7.30-7.28 (m, 4H, aromatic protons); 7.26-7.25 (m, 4H, aromatic protons); 7.18-7.16 (m, 4H, aromatic protons); 7.13-6.95 (m, 4H, aromatic protons); 6.89-6.86 (m, 4H, aromatic protons); 4.26-4.24 (s, 4H, CH$_2$CO): 3.75 (s, 6H, OCH$_3$); 3.74 (s, 6H, OCH$_3$); 3.66 (s, 4H, CH$_2$NH). $^{13}$C NMR (300 MHz, DMSO-d$_6$, δ): 166.8, 164.6, 160.6, 159.4, 138.1, 131.3, 129.8, 127.8, 114.6, 114.6, 79.6, 55.6, 55.5, 42.9, 33.2. ESI-MS m/z (%): C$_{46}$H$_{42}$N$_4$O$_8$ (M$^+$+Na)$^+$: 801.

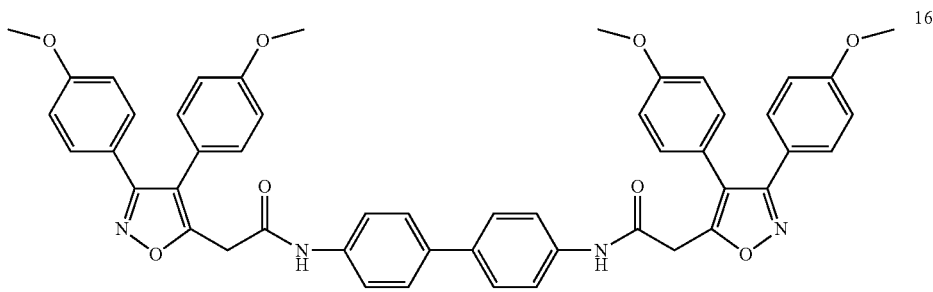

N,N'-(Biphenyl-4,4'-di-yl)bis(2-(3,4-bis(4-methoxyphenyl)isoxazol-5-yl)acetamide) (16). The product was isolated by column chromatography (silica gel; CHCl$_3$/MeOH=9:1). Mp 240-243° C. (yellow solid). 20% Yield. FT-IR (KBr): 3715, 3658, 2922, 1605, 1244, 1170, 1026, 827 cm$^{-1}$. $^1$H NMR (500 MHz, CDCl$_3$, δ): 8.10-8.00 (m, 2H, OCNH); 7.54-7.51 (m, 8H, benzidine aromatic protons); 7.43-7.41 (m, 4H, aromatic protons); 7.22-7.20 (m, 4H, aromatic protons); 6.95-6.94 (m, 4H, aromatic protons); 6.87-6.86 (m, 4H, aromatic protons); 3.89 (s, 4H, CH$_2$CO); 3.84 (s, 6H, OCH$_3$); 3.82 (s, 6H, OCH$_3$). ESI-MS: m/z (%): C$_{50}$H$_{42}$N$_4$O$_8$ (M−H)$^+$: 825.

3.2 General Procedure for the Preparation of Mofezolac-LK-Arachidonic Acid Compounds (Mof-LK-AA)

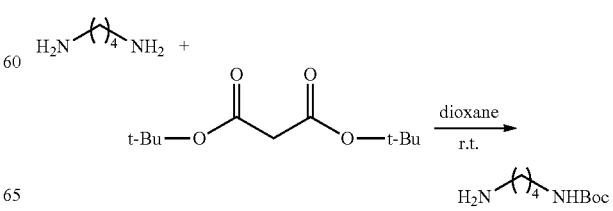

N-Boc-butandiamine. In an argon-flushed three-necked round bottom flask, equipped with a magnetic stirrer, a dropping funnel and an argon inlet, 1,4-diaminobutane (5 g, 56.72 mmol) was solubilized in anhydrous dioxane (40 mL). A yellow and limpid solution was obtained. Then, a solution of di-ter-butyl-carbonate (2.48 g, 11.34 mmol) in anhydrous dioxane (40 ml) was very slowly added by a dropping funnel. The obtained turbid reaction mixture was stirred for 16 h (overnight) at room temperature. Hence, the solvent was distilled under reduced pressure (T=60° C.) and, then, water (50 mL) was added to precipitate the di-protect derivative. The solid was filtered and solution was extracted with $CH_2Cl_2$ (5×30 mL). The combined organic phases were dried with anhydrous $Na_2SO_4$, filtered and the solvent removed under reduced pressure. The product was isolated as a yellow solid (yield=79%). FT-IR (KBr): 3359, 2976, 2933, 2866, 1694, 1528, 1453, 1391, 1365, 1276, 1252, 1174, 1042, 989, 867, 781 cm$^{-1}$. $^1$H NMR (400 MHz, CDCl$_3$, δ): 5.14 (s, 1H, NH); 2.94 (q, 2H, J=6.4 Hz); 2.53 (t, 2H, J=6.4 Hz); 1.36-1.26 (m, 13H); 1.07 (s, 2H, NH$_2$).

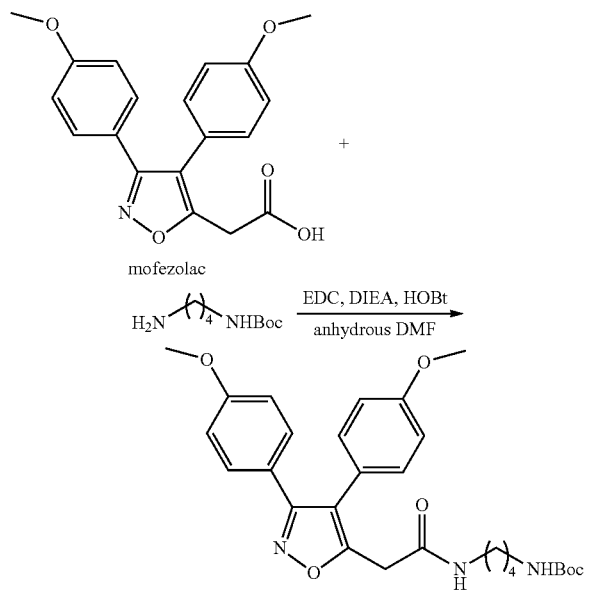

t-Butyl 4-(2-(3,4-bis(4-methoxyphenyl)isoxazol-5-yl)acetamido)butylcarbamate. In a three necked-flask (50 mL) equipped with a magnetic stirrer, mofezolac (500 mg, 1.47 mmol) was solubilized in dry DMF (35 mL). Then, N-BOC-butandiamine (800 mg, 4.25 mmol), 1-hydroxybenzotriazole monohydrate (HOBt H$_2$O, 309 mg, 1.80 mmol), N,N-diisopropylethylamine (0.74 ml, 4.25 mmol), 1-(3-dimethylaminopropyl)-3-ethylcarbodimide hydrochloride (EDC HCl, 294 mg, 1.54 mmol). The reaction mixture was stirred at room temperature for 16 h (overnight). The reaction progress is monitored by TLC (silica gel; CHCl$_3$/MeOH=9:1). The reaction was blocked by adding water (30 mL) and the aqueous phase was extracted with EtOAc (5×30 mL). The combined organic extracts were treated with sat. aq. NaCl to further removal of residual DMF, and then with anhydrous Na$_2$SO$_4$, filtered and the solvent distilled under reduced pressure. The product was isolated by column chromatography (silica gel; EtOAc/MeOH=95:0.5). 65% Yield. $^1$H NMR (400 MHz, CDCl$_3$, δ): 7.36-7.41 (m, 2H, aromatic protons); 7.14-7.18 (m, 2H, aromatic protons); 6.89-6.93 (m, 2H, aromatic protons); 6.82-6.87 (m, 2H, aromatic protons); 6.01 (s, 1H, CONHCH$_2$); 4.56 (s, 1H, NHBOC); 3.83 (s, 3H, OCH$_3$); 3.80 (s, 3H, OCH$_3$); 3.68 (s, 2H, CH$_2$CO); 3.27-3.29 (q, 2H, CONHCH$_2$); 3.11-3.13 (q, 2H, CH$_2$NHCO); 1.50-1.53 (m, 4H, CH$_2$CH$_2$); 1.43 (s, 9H, C(CH$_3$)$_3$). ESI-MS: m/z (%): C$_{28}$H$_{35}$N$_3$O$_6$ (M+Na)$^+$: 532.4.

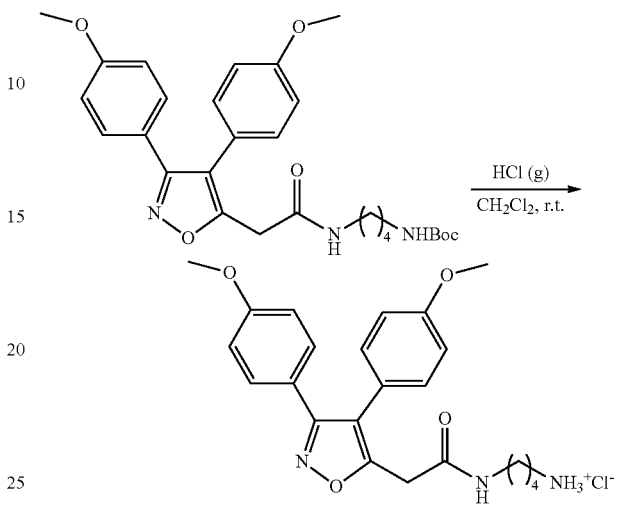

N-(4-Aminobutyl)-2-(3,4-bis(4-methoxyphenyl)isoxazol-5-yl)acetamide hydrochloride. In a three necked-flask (100 mL) equipped with a magnetic stirrer, t-butyl 4-(2-(3,4-bis(4-methoxyphenyl)isoxazol-5-yl)acetamido)butylcarbamate (120 mg, 0.236 mmol) was solubilized in CH$_2$Cl$_2$ (9 ml). HCl (g) was bubbled into the reaction flask for 1 h at 25° C. The limpid reaction mixture became from yellow to brown and turbid. The reaction progress was monitored by TLC (silica gel, CHCl$_3$/MeOH=9.5-0.5) following the disappearance of t-butyl 4-(2-(3,4-bis(4-methoxyphenyl)isoxazol-5-yl)acetamido)butylcarbamate. The product was isolated by removing the solvent under reduced pressure (92% yield). $^1$H NMR (400 MHz, CDCl$_3$, δ): 7.99 (s, 3H, NH$_3$$^+$); 7.35-7.40 (m, 2H, aromatic protons); 7.14-7.18 (m, 2H, aromatic protons); 6.81-6.92 (m, 4H, aromatic protons); 3.80 (s, 3H, OCH$_3$); 3.82 (s, 3H, OCH$_3$); 3.67 (s, 2H, CH$_2$CO); 3.24-3.30 (q, 2H, CH$_2$); 2.69-2.73 (t, 2H, CONHCH$_2$); 1.45-1.61 (m, 4H, CCH$_2$CH$_2$C).

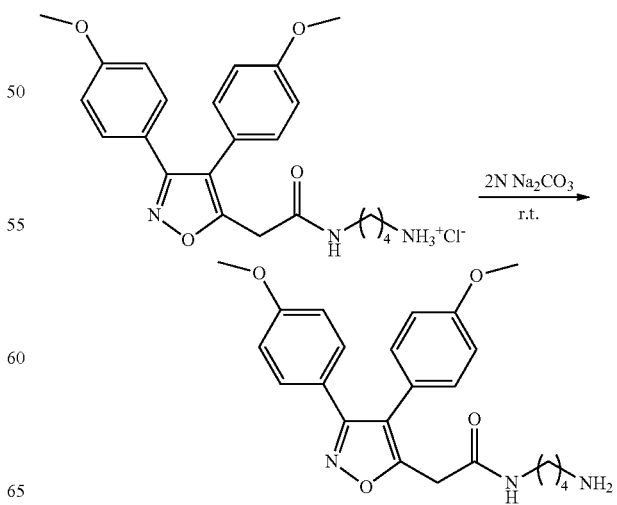

2-(3,4-Bis(4-methoxyphenyl)isoxazol-5-yl)-N-(4-aminobutyl)acetamide. N-(4-Aminobutyl)-2-(3,4-bis(4-methoxyphenyl)isoxazol-5-yl)acetamide hydrochloride was solubilized in a mixture of EtOAc (3 mL) and 2N $Na_2CO_3$. The suspension was stirred for 15 minutes at room temperature. Then, the two phases were separated and the organic portion was treated with 2N di $Na_2CO_3$ (3×30 ml). The combined organic phases were, then treated with anhydrous $Na_2SO_4$, filtered and the solvent distilled under reduced pressure. A yellow oil was obtained. $^1$H NMR (400 MHz, $CDCl_3$, δ): 7.35-7.40 (m, 2H, aromatic protons); 7.30-7.20 (bs, 3H, NH); 7.14-7.18 (m, 2H, aromatic protons); 6.81-6.92 (m, 4H, aromatic protons); 3.82 (s, 3H, $OCH_3$); 3.80 (s, 3H, $OCH_3$); 3.67 (s, 2H, $CH_2CO$); 3.24-3.30 (q, 2H, $CH_2$); 2.69-2.73 (t, 2H, $CONHCH_2$); 1.45-1.61 (m, 4H, $CCH_2CH_2C$).

1251 $cm^{-1}$. $^1$H NMR (400 MHz, $CDCl_3$, δ): 7.37-7.40 (m, 2H, aromatic protons); 7.14-7.18 (m, 2H, aromatic protons); 6.89-6.92 (m, 2H, aromatic protons); 6.82-6.89 (m, 2H, aromatic protons); 6.17-6.22 (m, 1H, CONH); 5.63 (m, 1H, NHCO); 5.31-5.40 (m, 8H, CH=CH); 3.83 (s, 3H, $OCH_3$); 3.80 (s, 3H, $OCH_3$); 3.68 (s, 2H, $CH_2CONH$); 3.24-3.30 (m, 4H, $CONHCH_2CH_2CH_2CH_2NHCO$); 2.79-2.84 (m, 6H, CH=CHCH_2); 2.01-2.18 (m, 6H, $NHCOCH_2CH_2CH_2$, $CH_3CH_2CH_2CH_2CH_2$, arachidonic acid); 1.64-1.74 (m, 2H, $NHCOCH_2CH_2$, arachidonic acid); 1.42-1.54 (m, 4H, $CONHCH_2CH_2CH_2CH_2NHCO$); 1.19-1.37 (m, 6H, $CH_3CH_2CH_2CH_2$, arachidonic acid); 0.85-0.90 (t, 3H, $CH_3$, arachidonic acid); ESI-MS m/z (%): $C_{43}H_{57}N_3O_5$ $(M+Na)^+$: 718.5; $(M-H)^+$: 694.3.

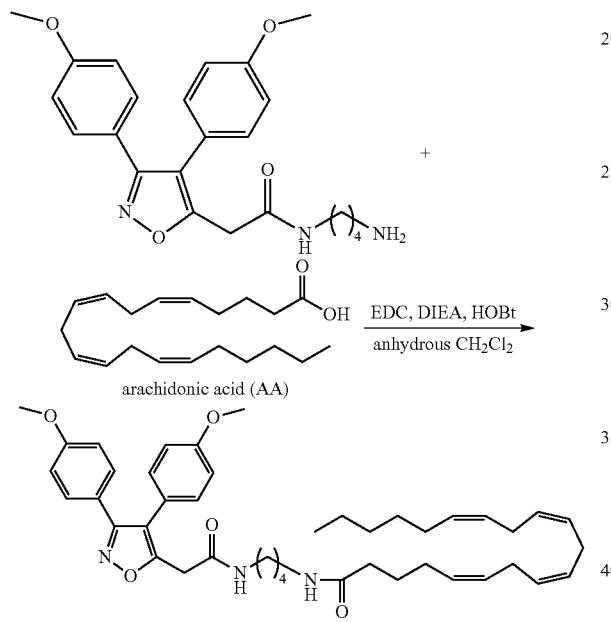

arachidonic acid (AA)

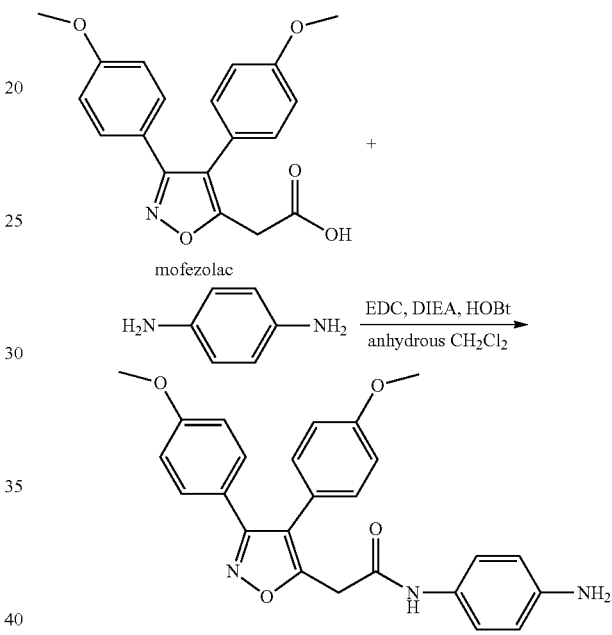

mofezolac (5Z, 8Z, 11Z, 14Z)—N-(4-(2-(3,4-bis(4-methoxyphenyl) isoxazol-5-yl)acetamido)butyl)icosa-5,8,11,14-tetraenamide. In an argon-flushed three-necked round bottom flask, equipped with a magnetic stirrer, an ice-bath, a dropping funnel and an argon inlet, arachidonic acid (0.027 ml, d=0.922 g/ml, 0,082 mmol) was solubilized in anhydrous $CH_2Cl_2$ (8 ml). Then, 1-hydrossibenzotriazole monohydrate (HOBt $H_2O$, 28 mg, 0.164 mmol) e 1-(3-dimetilamminopropil)-3-etilcarbodimmide (EDC HCl, 31.4 mg, 0.164 mmol). The reaction mixture was stirred at 0° C. for 2 h. Then, 2-(3,4-bis(4-methoxyphenyl) isoxazol-5-yl)-N-(4-aminobutyl)acetamide (67 mg, 0.164 mmol) and N,N-diisopropylethylamine (0.029 ml, 0.164 mmol) were added. The reaction mixture was allowed to reach room temperature and then stirred for 16 h (overnight). The 2-(3,4-bis(4-methoxyphenyl)isoxazol-5-yl)-N-(4-aminobutyl)acetamide disappearance was monitored by TLC (silica gel; $CHCl_3$/MeOH=9:1). The reaction mixture was treated with sat. aq. $NaHCO_3$ (3×30 ml) and then with sat. aq. $NH_4Cl$ (3×30 ml). The obtained organic phase was dried with anhydrous $Na_2SO_4$, filtered and the solvent removed under reduced pressure and room temperature. The product was isolated by column chromatography (silica gel; $CHCl_3$/MeOH=9:1). 73% Yield. Mp 97-99° C. FT-IR (KBr): 3439, 2929, 1649, N-(4-Aminophenyl)-2-(3,4-bis(4-methoxyphenyl)isxsazol-5-yl)acetamide (10). In an argon-flushed three-necked round bottom flask, equipped with a magnetic stirrer, an ice-bath, a dropping funnel and an argon inlet, mofezolc (50 mg, 0.147 mmol) was solubilized in anhydrous $CH_2Cl_2$ (4 ml). Then, 1-hydrossibenzotriazole monohydrate (HOBt $H_2O$, 20 mg, 0.147 mmol) e 1-(3-dimethylaminopropyl)-3-ethylcarbodimide hydrochloride (EDC HCl, 28 mg, 0.147 mmol). The reaction mixture was stirred at 0° C. for 2 h. In another flask, p-phenyllenediamine (16 mg, 0.147) and N,N-diisopropylethylamine (0.025 ml, 0.147 mmol) were solubilized in anhydrous $CH_2Cl_2$ (2 ml) under argon atmosphere, stirred for 30 minutes at room temperature and then very slowly added through a dropping funnel to the first flask. The whole reaction mixture was stirred at room temperature for 16 h (overnight). After, the solvent was removed under reduced pressure and product isolated by column chromatography (silica gel; $CHCl_3$/MeOH=9:1) as a yellow solid. 50% Yield. Mp 202-204° C. $^1$H NMR (400 MHz, $CDCl_3$, δ): 7.40-7.42 (m, 2H, aromatic protons); 7.30 (s, 1H, NH); 7.19-7.25 (m, 4H, aromatic protons); 6.92-6.94 (m, 2H, aromatic protons); 6.85-6.87 (m, 2H, aromatic protons); 6.64-6.66 (m, 2H, aromatic protons); 3.84 (s, 3H, $OCH_3$); 3.83 (s, 2H, $CH_2CO$); 3.82 (s, 3H, $OCH_3$); 3.62 (s, 2H, $NH_2$); ESI-MS m/z (%): $C_{25}H_{23}N_3O_4$ $(M+Na)^+$: 452.2.

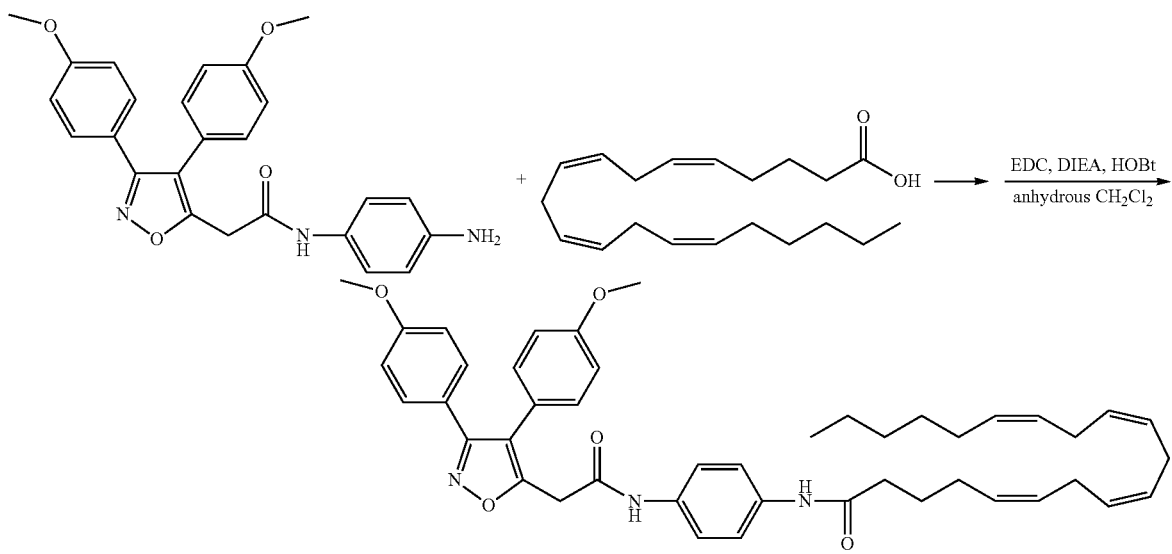

(5Z, 8Z, 11Z, 14Z)—N-(4-(2-(3,4-bis (4-metossyfenil) isossazol-5-il) acetammido) fenil) icosa-5,8,11,14-tetra-enammide. In an argon-flushed three-necked round bottom flask, equipped with a magnetic stirrer, an ice-bath, a dropping funnel and an argon inlet, arachidonic acid (0.012 ml, 0.038 mmol) was solubilized in anhydrous $CH_2Cl_2$ (2 ml). Then, 1-hydrossibenzotriazole monohydrate (HOBt $H_2O$, 20 mg, 0.147 mmol) and 1-(3-dimethylaminopropyl)-3-ethylcarbodimide hydrochloride (EDC HCl, 28 mg, 0.147 mmol) were added. The reaction mixture was stirred at 0° C. for 2 h. In another flask equipped with a magnetic stirrer, N-(4-aminophenyl)-2-(3,4-bis(4-methoxyphenyl)isxsazol-5-yl) acetamide (16 mg, 0.147) and N,N-diisopropylethylamine (0.025 ml, 0.147 mmol) were solubilized in anhydrous $CH_2Cl_2$ (2 ml) under argon atmosphere and stirred for 30 minutes at room temperature and then very slowly added through a dropping funnel to the first flask. The whole reaction mixture was stirred at room temperature for 16 h (overnight). Then, the reaction mixture was treated with sat. aq. $NaHCO_3$ (3×30 ml). The obtained organic phase was dried with anhydrous $Na_2SO_4$, filtered and the solvent removed under reduced pressure and room temperature. The product was isolated by column chromatography (silica gel; $CHCl_3/MeOH=9:1$). 85% Yield. Mp 133-135° C. $^1$H NMR (400 MHz, $CDCl_3$, δ): 7.42 (s, 1H, CONH). 7.40-7.48 (m, 4H, aromatic protons); 7.19-7.20 (m, 2H, aromatic protons); 7.09 (s, NHCO); 6.93-6.94 (m, 2H, aromatic protons); 6.85-6.87 (m, 2H, aromatic protons); 5.35-5.42 (m, 8H, CH═CH); 3.85 (s, 2H, $CH_2CONH$); 3.84 (s, 3H, $OCH_3$); 3.81 (s, 3H, $OCH_3$); 2.80-2.85 (m, 6H, CH═$CHCH_2$, arachidonic acid); 2.05-2.35 (m, 6H, $NHCOCH_2CH_2CH_2$, $CH_3CH_2CH_2CH_2CH_2$, arachidonic acid); 1.80-1.85 (m, 2H, $NHCOCH_2CH_2$, arachidonic acid); 1.24-1.37 (m, 6H, $CH_3CH_2CH_2CH_2$ arachidonic acid); 0.88-0.90 (m, 3H, $CH_3$, arachidonic acid); ESI-MS: m/z (%): $C_{45}H_{53}N_3O_5$ $(M+Na)^+$: 738.5.

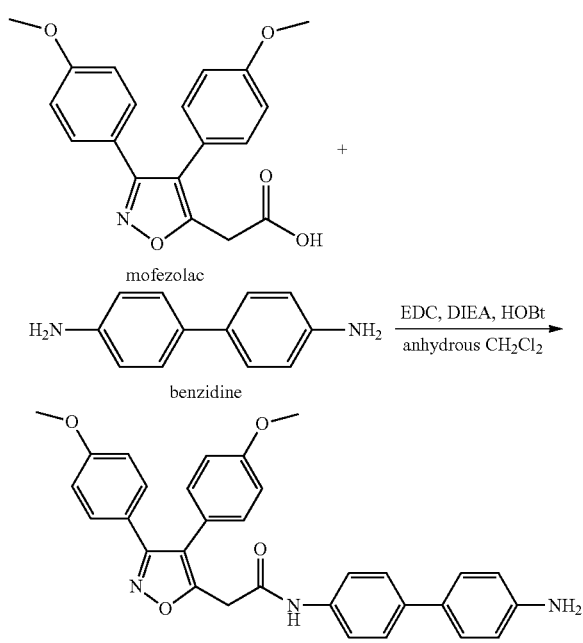

N-(4'-Amino-[1,1'-biphenyl]-4-yl)-2-(3,4-bis(4-mehoxyphenyl)isoxazol-5-yl)acetamide (11). In an argon-flushed three-necked round bottom flask, equipped with a magnetic stirrer, an ice-bath, a dropping funnel and an argon inlet, mofezolac (50 ml, 0.143 mmol) was solubilized in anhydrous $CH_2Cl_2$ (4 ml). Then, 1-hydrossibenzotriazole monohydrate (HOBt $H_2O$, 20 mg, 0.147 mmol) and 1-(3-dimethylaminopropyl)-3-ethylcarbodimide hydrochloride (EDC HCl, 28 mg, 0.147 mmol) were added. The reaction mixture was stirred at 0° C. for 2 h. In another flask equipped with a magnetic stirrer, benzidine (27 mg, 0.147) and N,N-diisopropylethylamine (0.025 ml, 0.147 mmol) were solubilized in anhydrous $CH_2Cl_2$ (2 ml) under argon atmosphere and stirred for 30 minutes at room temperature and then very slowly added through a dropping funnel to the first flask. The whole reaction mixture was stirred at room temperature for 16 h (overnight). Then, the reaction mixture was treated with sat. aq. NaHCO$_3$ (3×30 ml). The obtained organic phase was dried with anhydrous Na$_2$SO$_4$, filtered and the solvent removed under reduced pressure and room temperature. The product was isolated by column chromatography (silica gel; CHCl$_3$/MeOH=10:1). 27% Yield. Mp 204-206° C. $^1$H NMR (400 MHz, CDCl$_3$, δ): 7.54 (bs, 1H, NH); 7.49-7.52 (m, 4H, aromatic protons); 7.38-7.42 (m, 4H, aromatic protons); 7.20-7.22 (m, 4H, aromatic protons); 6.93-6.95 (m, 2H, aromatic protons); 6.85-6.87 (m, 2H, aromatic protons); 6.74-6.76 (m, 2H, aromatic protons); 3.88 (s, 2H, CH$_2$CO); 3.84 (s, 3H, OCH$_3$); 3.81 (s, 3H, OCH$_3$); 3.63-3.66 (bs, 2H, NH$_2$). $^{13}$C NMR (500 MHz, CDCl$_3$, δ): 9.3; 17.9; 24.6; 24.9; 27.1; 30.5; 50.5; 58.3; 109.2; 109.7; 110.6; 113.07; 115.6; 116.1; 116.4; 122.05; 123; 125.07; 125.9; 126.3; 130.8; 133.07; 141.06; 154.8; 155.9; 156.5; 157.3; 159.6. ESI-MS: m/z (%): C$_{31}$H$_{27}$N$_3$O$_4$ (M+Na)$^+$: 528.2.

and the solvent removed under reduced pressure and room temperature. The product was isolated by column chromatography (silica gel; CHCl$_3$/MeOH=10:1). 31% Yield. Mp 132-134° C. $^1$H NMR (400 MHz, CDCl$_3$, δ): 7.65 (s, 1H, CONH); 7.50-7.57 (m, 8H, aromatic protons); 7.40-7.42 (m, 2H, aromatic protons); 7.20-7.23 (m, 3H, 2 aromatic protons and NHCO); 6.93-6.95 (m, 2H, aromatic protons); 6.85-6.87 (m, 2H, aromatic protons); 5.33-5.43 (m, 8H, CH=CH, arachidonic acid); 3.88 (s, 2H, CH$_2$CONH); 3.84 (s, 3H, OCH$_3$); 3.81 (s, 3H, OCH$_3$); 2.80-2.83 (m, 6H, CH=CHCH$_2$, arachidonic acid); 2.01-2.07, 2.18-2.20, 2.37-2.40 (m, 6H, NHCOCH$_2$CH$_2$CH$_2$, CH$_3$CH$_2$CH$_2$CH$_2$CH$_2$, arachidonic acid); 1.83-1.85 (m, 2H, NHCOCH$_2$CH$_2$, arachidonic acid); 1.26-1.38 (m, 6H, CH$_3$CH$_2$CH$_2$CH$_2$, arachidonic acid); 0.87-0.92 (m, 3H, CH$_3$, arachidonic acid). $^{13}$C NMR (500 MHz, CDCl$_3$, δ): 14.07; 14.1; 22.5; 22.6;

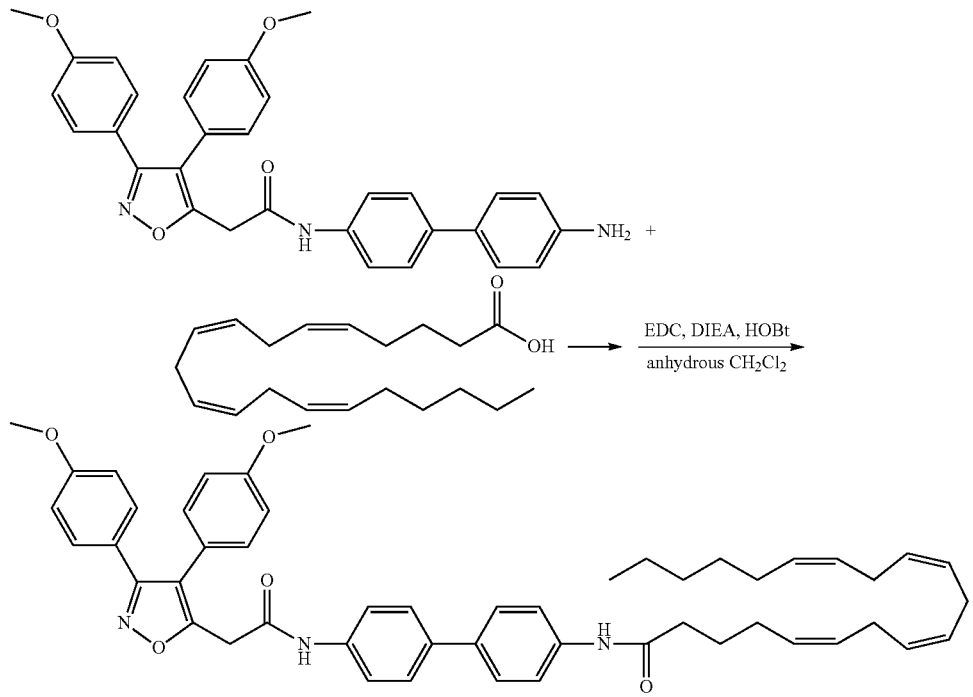

(5Z,8Z,11Z,14Z)—N-(4'-(2-(3,4-bis(4-methoxyphenyl)isoxazol-5-yl)acetamido)-[1,1'-biphenyl]-4-yl)icosa-5,8,11,14-tetraenamide (13). In an argon-flushed three-necked round bottom flask, equipped with a magnetic stirrer, an ice-bath, a dropping funnel and an argon inlet, arachidonic acid (0.011 ml, 0.033 mmol) was solubilized in anhydrous CH$_2$Cl$_2$ (2 ml). Then, 1-hydrossibenzotriazole monohydrate (HOBt H$_2$O, 6 mg, 0.039 mmol) and 1-(3-dimethylaminopropyl)-3-ethylcarbodimide hydrochloride (EDC HCl, 8 mg, 0.039 mmol) were added. The reaction mixture was stirred at 0° C. for 2 h. In another flask equipped with a magnetic stirrer, N-(4'-amino-[1,1'-biphenyl]-4-yl)-2-(3,4-bis(4-methoxyphenyl)isoxazol-5-yl)acetamide (20 mg, 0.039) and N,N=diisopropylethylamine (0,007 ml, 0,039 mmol) were solubilized in anhydrous CH$_2$Cl$_2$ (2 ml) under argon atmosphere and stirred for 30 minutes at room temperature and then very slowly added through a dropping funnel to the first flask. The whole reaction mixture was stirred at room temperature for 16 h (overnight). Then, the reaction mixture was treated with sat. aq. NaHCO$_3$ (3×30 ml). The obtained organic phase was dried with anhydrous Na$_2$SO$_4$, filtered 25.2; 25.6; 25.7; 26.5; 27.1; 27.2; 29.2; 29.3; 29.4; 29.5; 29.6; 29.7; 30; 31.5; 31.9; 32.8; 35.2; 37; 55.2; 55.3; 63.1; 114; 114.5; 117.8; 120.1; 120.4; 120.8; 121.1; 127.2; 127.3; 127.5; 127.8; 128.1; 128.2; 128.6; 129; 129.8; 129.9; 130.5; 131.1; 136.2; 136.3; 137; 137.1; 159.6; 160.7; 161.3; 162; 164.5; 171. ESI-MS m/z (%): C$_{51}$H$_{57}$N$_3$O$_5$ (M+Na)$^+$: 814.5.

4. Inhibition of Ovine COX-1 and COX-2 Catalytic Activity

The target compounds were evaluated for their ability to inhibit ovine COX-1 and COX-2 enzyme catalytic activity (percent inhibition at 50 mm, unless otherwise indicated). IC$_{50}$ values were determined only for compounds that showed a reasonable COX-1 inhibitory activity (>50%) at 50 mm. Each reported IC$_{50}$ value and the percentage of inhibition (measured at 50 mm as the tested compound concentration) is the average of the results of three separate assays (triplicate). Enzyme inhibition was determined using a colorimetric COX (ovine) inhibitor screening assay kit (Cayman Chemicals, Ann Arbor, MI, USA) following the manufacturer's instructions. Stock solutions of test compounds were dissolved in a minimum volume of DMSO.

| Compound | COX-1 IC$_{50}$ (μM) [% inhibition at 50 μM] | COX-2 IC$_{50}$ (μM) [% inhibition at 50 μM] |
| --- | --- | --- |
| 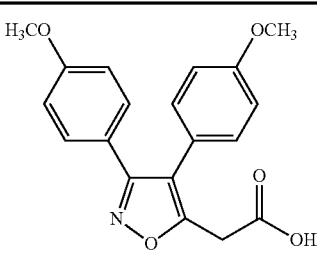 mofezolac | 0.0079 [100] | >50 [38] |
| 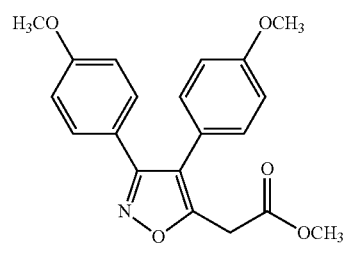 mofezolac methyl ester | n.d. | n.d. |
| 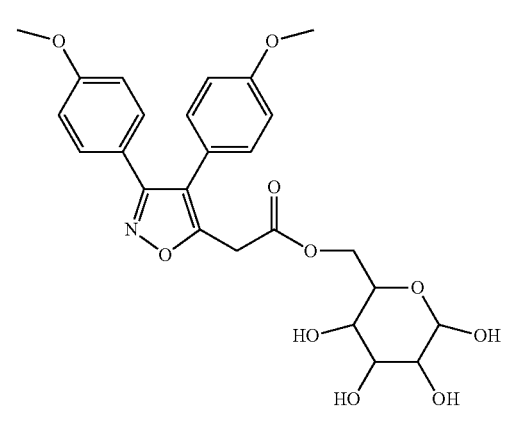 GALMOF$_0$ | 0.1 [100] | 0.7 [87] |
| 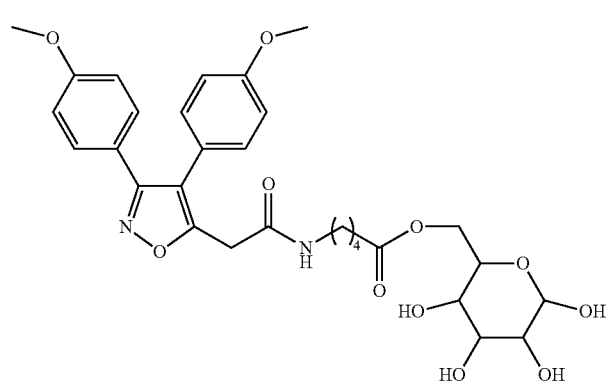 GALMOF$_5$ | >50 [38] | >50 [24] |

-continued
| Compound | COX-1 IC$_{50}$ (μM) [% inhibition at 50 μM] | COX-2 IC$_{50}$ (μM) [% inhibition at 50 μM] |
|---|---|---|
| 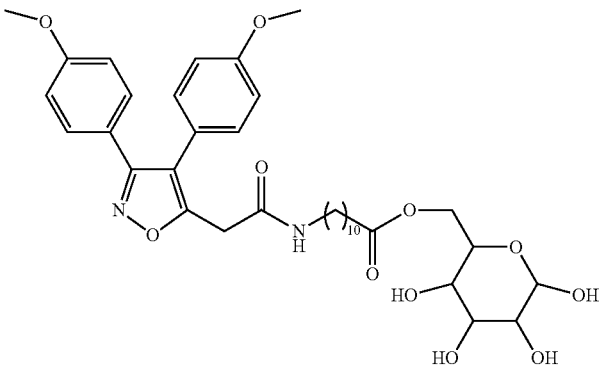<br>GALMOF$_{11}$ | 0.1 [90] | 0.27 [64] |
| 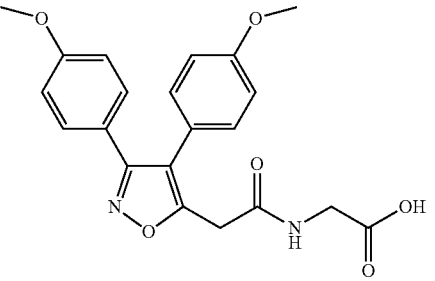<br>MPA 206 | [23] | [17] |
| 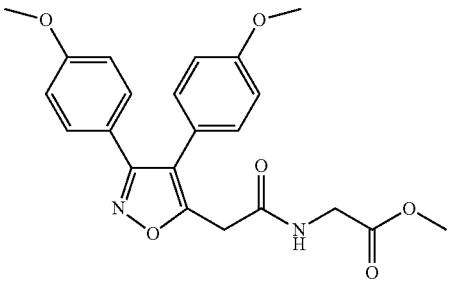<br>MPA195 | 0.07 [95] | 4.4 [80] |
| 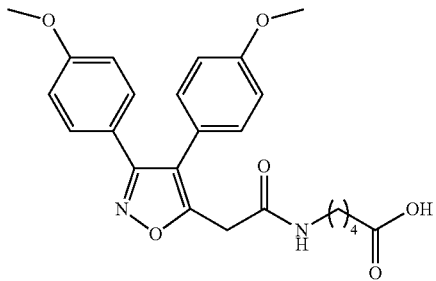<br>MPA199 | 3.3 [74] | >50 [22] |

-continued
| Compound | COX-1 IC$_{50}$ (μM) [% inhibition at 50 μM] | COX-2 IC$_{50}$ (μM) [% inhibition at 50 μM] |
|---|---|---|
| 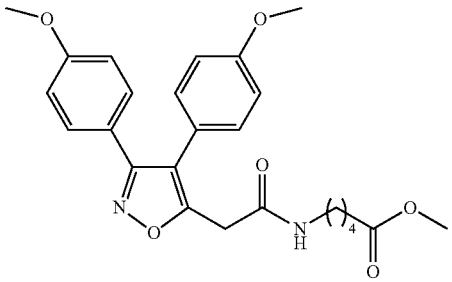 MPA190 | 0.1 [91] | 2 [65] |
| 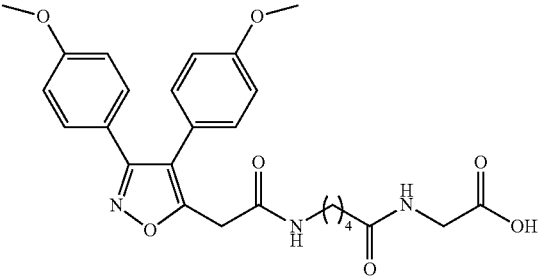 MPA239 | >50 [23] | >50 [8] |
| 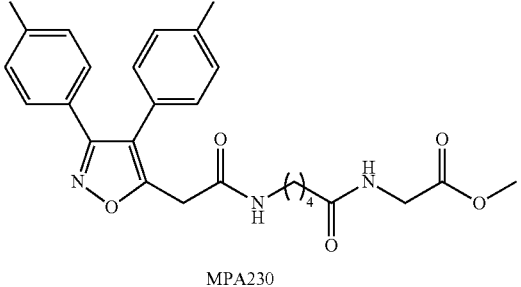 MPA230 | 0.7 [76] | 57 [49] |
| 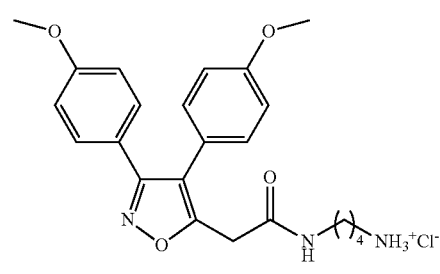 MPA270 | 1.1 [94] | n.d. |

-continued
| Compound | COX-1 IC$_{50}$ (μM) [% inhibition at 50 μM] | COX-2 IC$_{50}$ (μM) [% inhibition at 50 μM] |
|---|---|---|
| 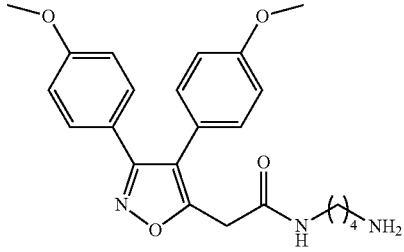  MPA 290 | 0.95 [100] | 3.5 [51] |
| 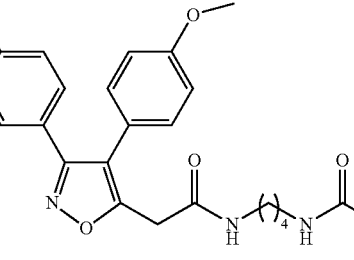  MPA236 | 50 [43] | 0.1 [49] |
|   MPA 548 | 39 [54] | not active |
| 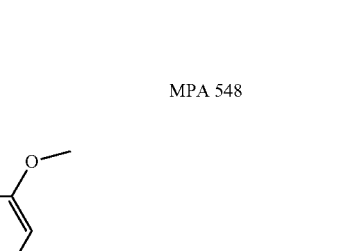  MPA 551 | not active | not active |

| Compound | COX-1 IC$_{50}$ (μM) [% inhibition at 50 μM] | COX-2 IC$_{50}$ (μM) [% inhibition at 50 μM] |
|---|---|---|
| 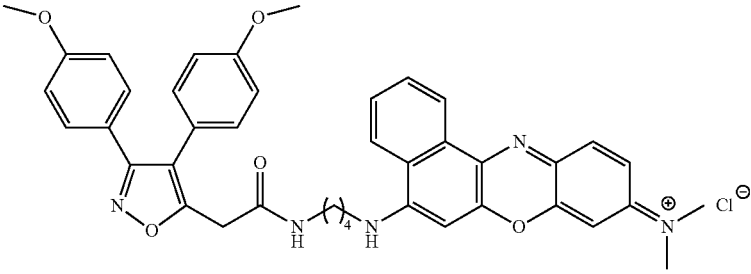<br>Mof-C4-Nile blue | nd | nd |
| 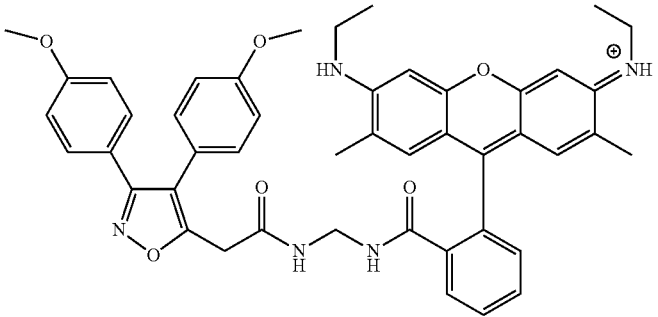<br>MPA 306 | | |
| 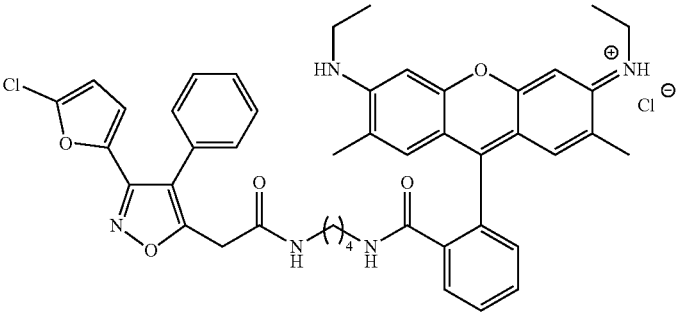<br>MPA15 (DQ3) | 6.0 [69] | –[0] |
| 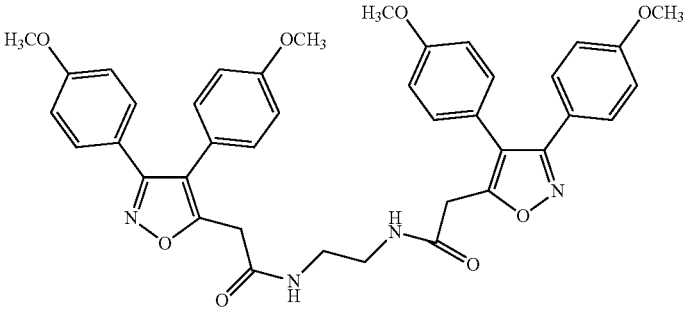<br>MPA361 | 0.013 [75] | 0.12 [45] |

-continued
| Compound | COX-1 IC$_{50}$ (μM) [% inhibition at 50 μM] | COX-2 IC$_{50}$ (μM) [% inhibition at 50 μM] |
|---|---|---|
| 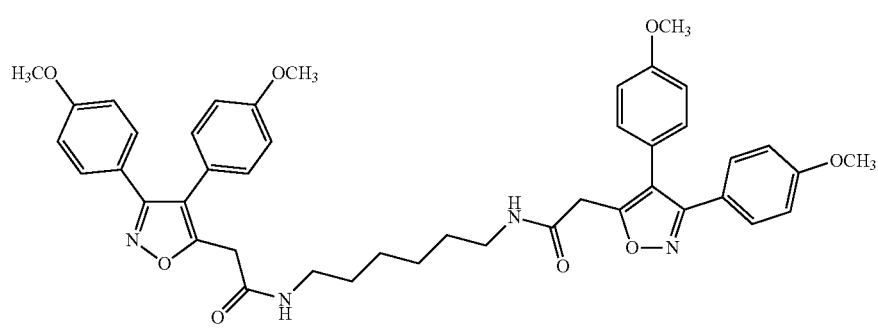 MPA448 | 9 [50] | >50 [22] |
| 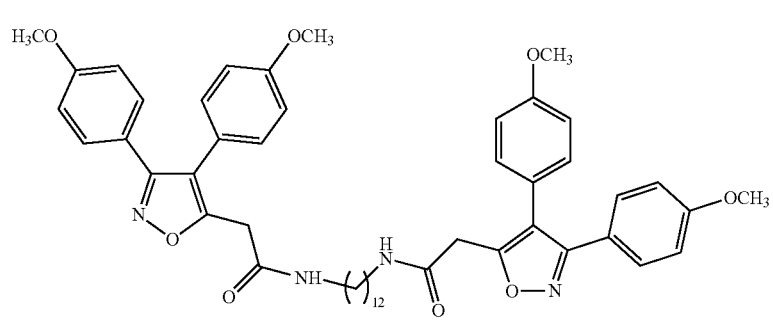 MPA434 | 7.1 [40] | >50 |
| 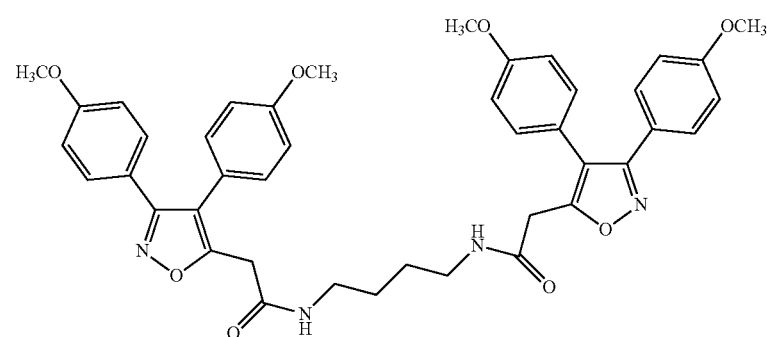 MPA354 | 5.5 [74] | >50 |
| 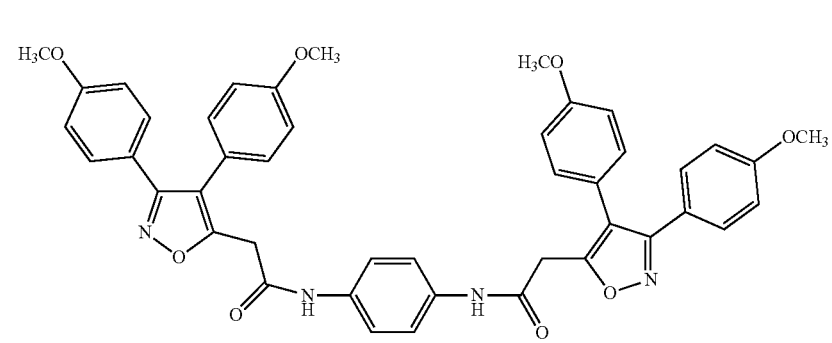 MPA415 | 0.15 [85] | >50 |

-continued
| Compound | COX-1 IC$_{50}$ (μM) [% inhibition at 50 μM] | COX-2 IC$_{50}$ (μM) [% inhibition at 50 μM] |
|---|---|---|
| 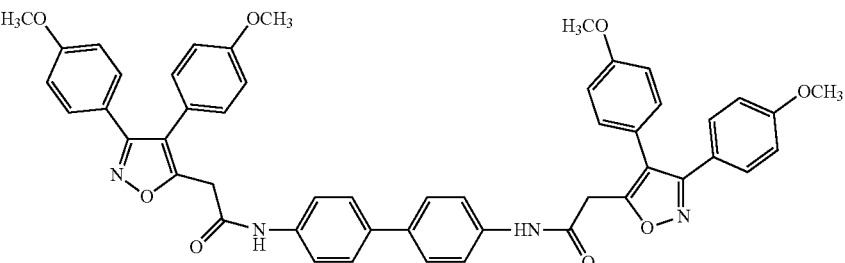 MPA 462 | 0.08 [73] | >50 |
| 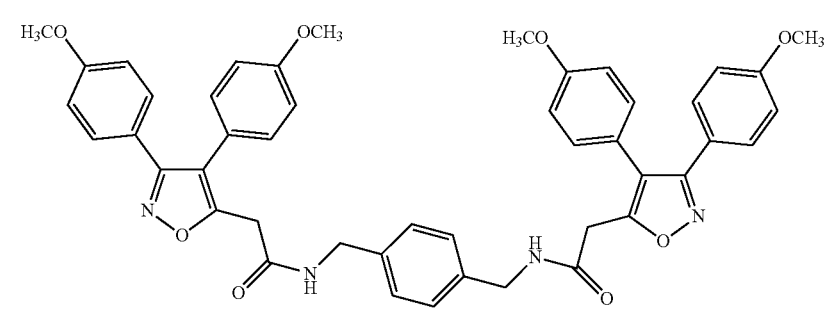 MPA 422 | >50 | >50 |
| 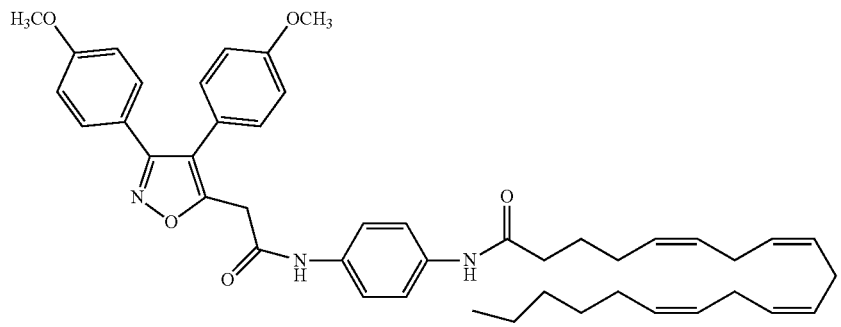 MPA439 | 0.049 [66] | >50 [40] |
| 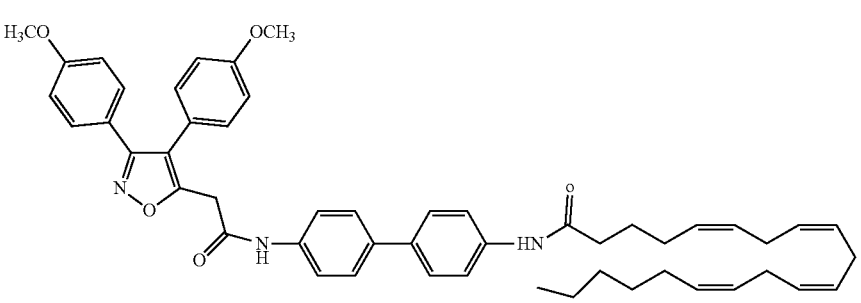 MPA450 | 17 [50] | 0.09 [60] |

| Compound | COX-1 IC$_{50}$ (μM) [% inhibition at 50 μM] | COX-2 IC$_{50}$ (μM) [% inhibition at 50 μM] |
|---|---|---|
| 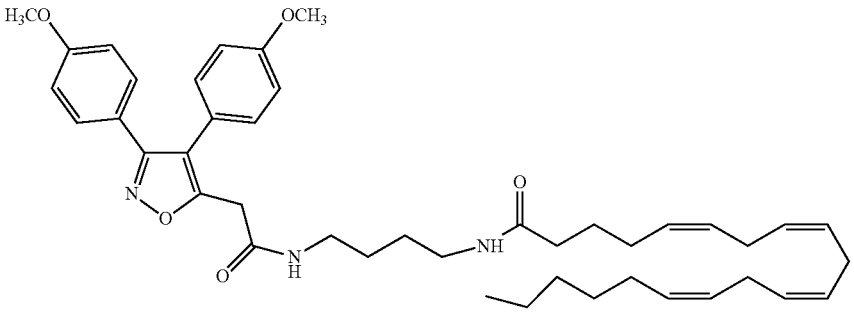 MPA 362 | 16 [57] | 0.8 [61] | nd = not determined

Further experimental data on in vitro and in vivo models of neuroinflammation

1. Material and Methods

Reagents

P6 (3-(5-chlorofuran-2-yl)-5-methyl-4-phenylisoxazole) was synthesized according to Di Nunno L. et al. (2004), whereas mofezolac was synthesized following Micetich's protocol (Micetich, 1981). All the other reagents and solvents were purchased from Sigma-Aldrich (Milan, Italy) and used without any further purification.

Lipopolysaccharide (LPS) from *Escherichia coli* serotype 0127:B8 was purchased from Sigma-Aldrich (Milan, Italy). The goat polyclonal a p-IκB (sc-7977) antibody (Ab) was purchased from Santa Cruz Biotechnology (DBA, Milan, Italy), COX-1 (Ab 695), COX-2 (Ab 15191) Abs were obtained from Abcam (Cambridge, UK). Goat anti-rabbit IgG (sc-2004), goat anti-mouse IgG (sc-2005) and donkey anti-goat IgG (sc-2020) were purchased from Santa Cruz Biotechnology; mouse primary monoclonal antibody (mAb) anti-glial fibrillary acidic protein (GFAP) (Merck Millipore, Milan, Italy), mouse mAb anti-ionized calcium-binding adapter molecule-1 (Iba-1) (Merck Millipore). Elisa kit for PGE$_2$ evaluation was purchased from Cayman Chemical (Ann Arbor, MI, USA). MTT [3-(4,5-dimethylthiazol-2-yl)-2,5-diphenyltetrazolium bromide], 3,3'-diaminobenzidine and tribromoethanol were obtained from Sigma-Aldrich, Milan, Italy.

Cell Cultures and Treatment

BV2 microglia cells (ICLC HTL 03001-Interlab Cell Line Collection) were grown in high glucose Dulbecco's modified Eagle's medium (DMEM) supplemented with 10% foetal bovine serum, 100 units/ml penicillin, and 100 μg/mL streptomycin. They were maintained at 37° C. in a humidified 5% CO$_2$/95% environmental air.

Then, microglial cells were plated, at a density of 25×10$^4$/well in 6-well plates (Falcon) and treated with the chosen COX inhibitors (P6, mofezolac) when they reached 80% confluence. Preliminary experiments were conducted to establish the optimal concentration and exposure times necessary for LPS (1 μg/mL) treatment, which were found to be in accordance with other reports (Bi et al., 2014; Haw et al., 2014), as well as to establish the optimal dose of the COX inhibitors and exposure times to detect their effects on LPS-stimulated BV2 microglial cell function. In this regard, a set of experiments was carried out in which microglial cells were 1 h pre-treated with the selective COX-1 inhibitors P6 (0.5 and 1.0 μM) or mofezolac (0.1 and 0.5 μM). Cells were then incubated for different times at 37° C. with LPS, as pro-inflammatory stimulus. Experiments included cells grown in medium alone (control).

Cell Viability Test

Cell viability of microglial cells was quantified using the MTT reduction assay. The cells (8×10$^3$/well) were grown in 96-well plates (Becton Dickinson Labware) in complete medium and treated with different concentration of COX inhibitors, in presence or absence of LPS. Untreated cells were used as a control. A PBS 1× solution of MTT (5 mg/mL) was prepared and added to the cell medium at a final concentration of 0.5 mg/mL. Cells were incubated for 4 h at 37° C. and 5% CO$_2$ to allow the MTT metabolism. The formazan crystals formed (from MTT) into the cells were solubilized with DMSO (Sigma-Aldrich). The levels of MTT formazan were determined measuring the optical density at λ=560 nm and subtracting the background (λ=670 nm) with a Victor Multiplate Reader (Wallac). Optical density was directly correlated to cell quantity.

Immunoblotting Assay

After treatment of cultures as previously described, cells were harvested and lysed by ice-cold lysis buffer [1% Triton X-100, 20 mM Tris-HCl, 137 mM NaCl, 10% glycerol, 2 mM EDTA, 1 mM phenylmethylsulfonyl fluoride (PMSF), 20 μM leupeptin hemisulfate salt, 0.2 U/mL aprotinin (all from Sigma-Aldrich)] for 30 min on an ice-bath.

Substantia nigra pars compacta (SNpc), Hippocampus, Frontal lobe and Caudate from mice brains were minced in ice-cold PBS, washed and then homogenized in a buffer containing lysis buffer (50 mM Tris pH 8, 0.02 g/mL NaCl, 0.2% SDS, 1% Triton-X, 4 U/ml aprotinin, 2 mM leupeptin, 100 mM phenylmethanesulfonyl fluoride).

The tissue and cell culture lysates were vortexed for 15-20 s and, then, centrifuged at 12,800×g for 20 min. The protein concentration in the supernatant was spectrophotometrically determined by Bradford's protein assay (Bradford, 1976). Protein samples were diluted with sample buffer (0.5 M Tris-HCl pH=6.8, 10% glycerol, 10% (w/v) SDS, 5% 2-mercaptoethanol, 0.05% (w/v) bromophenol blue) and then boiled for 3 min. Proteins (25 μg/lane) and prestained standards (BioRad Laboratories, Hercules, CA, USA) were loaded on 7% or 12% SDS precast polyacrylamide gels (BioRad Laboratories).

After electrophoresis, the resolved proteins were transferred from the gel to nitrocellulose membranes. A blotting buffer [20 mMTris/150 mM glycine, pH=8.0, 20% (v/v) methanol] was used for gel and membrane saturation and blotting. Then, membranes were incubated in the dark with 1 µg/mL mouse monoclonal antibody (MoAb) anti-COX-1 and rabbit polyclonal Ab anti-COX-2 (1:1000) (both from AbCam, Cambridge, UK), rabbit polyclonal Ab anti p-IkB-α (1:200), mouse polyclonal Ab anti β-actin (1:500) (all from Santa Cruz Biotechnology), mouse MoAb anti-glial fibrillary acidic protein (GFAP) (1:200) and mouse mAb anti-ionized calcium-binding adapter molecule-1 (Iba-1) (1:200) (both from Merck Millipore) overnight at 4° C. The membranes were washed with 0.1% Tween 20-PBS (for 20 min, 3 times) and then incubated with the secondary antibody diluted 1:2000 for 60 min. Bands were visualized by chemiluminescence detection (Invitrogen, Milan, Italy). The β-actin level was used as a protein loading control. For tissue analysis, obtained bands were normalized to the level of β-actin performed for each cerebral area tested. For cell cultures the bands were normalized to the β-actin level in each experimental condition.

Animals and Treatment Protocols

This study was carried out in strict accordance with the European Council Directive 86/609/EEC and the Italian animal welfare legislation (art. 4 and 5 of D.L. 116/92). Seventy adult male 129/SV mice (22-24 g body mass, 8-10 weeks of age) were purchased from Harlan-Italy and were kept under environmentally controlled conditions (20±2° C., 50-80% humidity, 12 h light/dark cycle, food and water ad libitum).

Mice received either the selective COX-1 inhibitor mofezolac (6 mg/kg, i.p.; indicated as M in all the Figures) or vehicle (40% DMSO in 0.1 M phosphate buffer, pH=7.4; VM in all the Figures) once a day for 10 days. Mofezolac amount to be injected was chosen taken into account previous study and its COXs $IC_{50}$ values [14]. On the seventh day, mice were anesthetized with tribromoethanol (250 mg/Kg, i.p.) and positioned in a stereotactic apparatus (Kopf Instruments, Tujunga, CA, USA). Vehicle (sterile saline, 5 µl; V-LPS in all the Figures) or 5 µg LPS in 5 µL of sterile saline (LPS in all the Figures) was administered into the cerebral lateral ventricle using a fine needle glass syringe (Hamilton, Lyon, France) and a syringe pump (KD Scientific, Holliston, MA, USA) at a rate of 1 µL/min. This LPS dose and time point (72 h) induced the best neuroinflammatory response following a titration preliminary study (data not shown). Sterotaxic injections coordinates were: 2.3 mm dorsal/ventral, 1.0 mm lateral, and 0.5 mm anterior/posterior from the bregma. Mofezolac was given 30 min prior to LPS injection (M+LPS in all the Figures).

Immunohistochemical Staining

Mice were transcardially perfused with tris-buffered saline (pH=7.6) followed by 4% paraformaldehyde in PBS pH=7.4 at 4° C. Brains were subsequently post-fixed in the same fixative, paraffin embedded and 10 µm slices were obtained with a rotative microtome (Leica, Milan, Italy). Immunohistochemistry was performed following a standard avidin-biotin complex procedure. Briefly, specimens were incubated with mouse primary monoclonal antibody (mAb) anti-glial fibrillary acidic protein (GFAP) at a ratio of 1:1000 (Merck Millipore, Milan, Italy), or a mouse mAb anti-ionized calcium-binding adapter molecule-1 (Iba-1) at a ratio of 1:500 (Merck Millipore) overnight at 4° C. and then with an anti-mouse biotinylated secondary Ab (Dako, Milan, Italy), at a 1:1000 dilution for 1 h at room temperature. The antigen-Ab complexes were visualized by sections incubation for 1 h with extravidin peroxidase (Sigma-Aldrich) diluted 1:1500 and 3,3'-diaminobenzidine oxidation in the presence of $H_2O_2$.

$PGE_2$ Assay

Microglial cells were cultured in 6-well plates at a density of $3 \times 10^6$ cells/well. Then, the cells were pre-treated with selective COX-1 inhibitors P6 or mofezolac for 1 h and, subsequently stimulated with LPS (1 µg/mL). The cultures were maintained at 37° C. for 24 and 48 h in a humidified air containing a 5% $CO_2$. $PGE_2$ levels were determined in the supernatant using a competitive binding immunoassay (Cayman Chemical, Ann Arbor, MI, USA) following the manufacturer's instructions. Unstimulated cells were included as a control. $PGE_2$ amount determination in the brain was performed in the tissue extracts, according to the manufacturer's instructions. The optical density was measured at $\lambda=405$-420 nm with precision microplate reader and the amount of $PGE_2$ (ng/mL) was calculated using a $PGE_2$ standard curve.

Densitometric Analysis

The bands obtained after immunoblotting and RT-PCR were submitted to densitometric analysis using ID Image Analysis Software (Kodak Digital Science). Results were expressed as arbitrary units.

Statistical Analysis

Student's t test and analysis of variance (one-way ANOVA) on the results of at least five independent biological replicates were performed. Values of $p<0.05$ were considered statistically significant.

2. Results

BV2 Microglial Cell Viability Assay

MTT assay was used to quantitatively evaluate cell viability. This was performed to verify whether the tested selective COX-1 inhibitors (P6 and mofezolac) caused toxicity in LPS-treated BV2 cell line. Preliminarily, the effect of two different concentrations of P6 (0.5 and 1 µM) and mofezolac (0.1 and 0.5 µM) on BV2 microglial cell viability was evaluated. No cell toxicity was exerted by either P6, mofezolac, LPS alone or a combination of LPS and each of the two inhibitors at 24 h. The two concentrations of P6 and mofezolac were chosen based on the basis of previous studies and their COXs IC50 values (Calvello et al., 2012).

Cell viability was found to be significantly ($p \leq 0.001$) lower, after 48 h of LPS treatment (percentage cell viability equal to 78.4±0.15 vs 99.8±0.07 of the control), than untreated cells (control). None of the inhibitors used at the above indicated doses were toxic to BV2 microglial cells, when used in the absence of LPS (percentage cell viability ranging between 95.5±0.22 and 98.2±0.16 vs control). In addition, inhibitors used at the same doses, resulted protective toward BV2 microglial cells after 48 h LPS treatment (1 µg/mL), being the percentage of cell viability comparable to that observed in control.

Evaluation of Mice Glial Activation

Figure 2S:
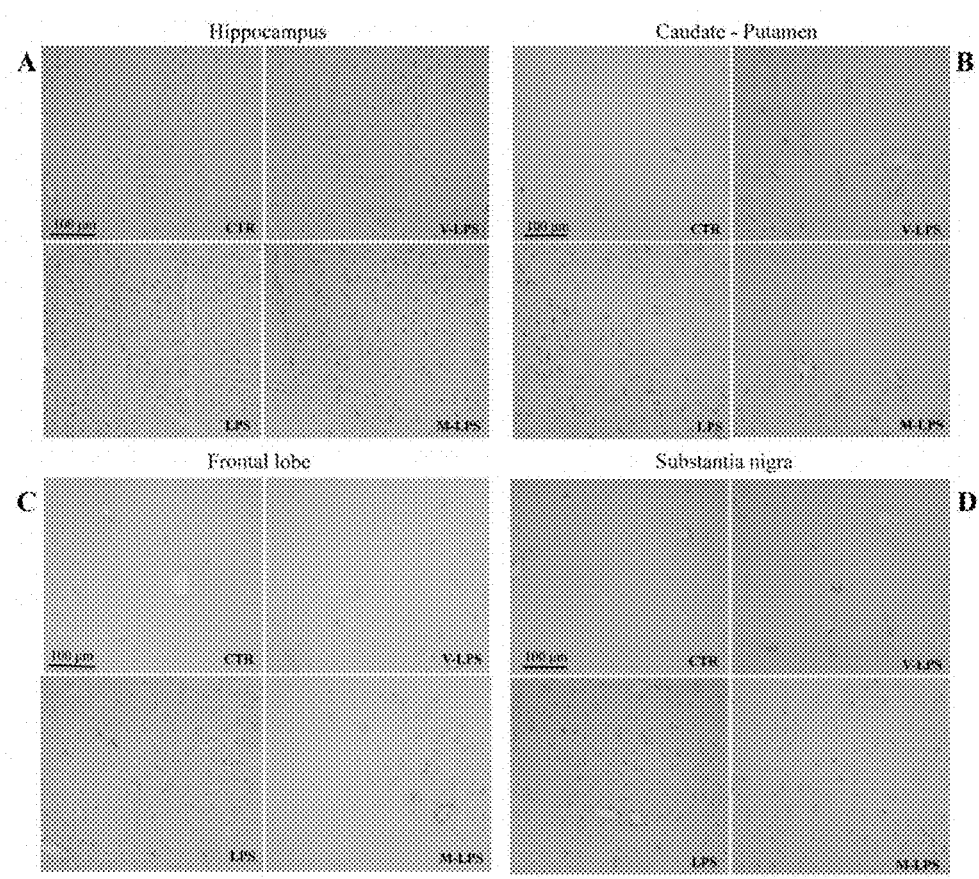
FIG. 2S. GFAP immunoreactivity in the hippocampus (A), caudate-putamen (B), frontal lobe (C) and substantia nigra (D), in slices of control (CTR), vehicle of LPS (v-LPS), LPS, mofezolac and LPS (M-LPS) treated mice.

Astroglial activation was characterized by immunoreactivity and immunoblotting analysis of the GFAP expression, a marker used to distinguish astrocytes from other glial cells of the CNS. LPS treatment determined an increase of immunoreactive cell bodies in comparison to untreated mice suggesting astrocyte activation in different brain regions. In particular, the caudate, frontal lobe, hippocampus and substantia nigra were selected in order to evaluate the astrocyte activation after different animal treatment [FIG. 2S (A-D)]. Images report GFAP reactivity in samples of mice control group (CTR), mice treated with LPS-vehicle (V-LPS), LPS alone (LPS) or in combination with mofezolac (M+LPS). In CTR sections, there is a physiological astroglial distribution with few immunoreactive elements surrounding the blood vessels as part of the brain-blood barrier, that means that there are no sign of reactive astrogliosis. In V-LPS treated mice, the expression is similar to CTRL, with perivascular immunoreactivity and the presence of a few astrocytes in the tissue, due to inflammation probably caused from the injection. In LPS-treated mice images show a marked increase of the immunoreactive elements, whereas in vivo administration of mofezolac reduced the presence of GFAP immunoreactive cells in all the tested brain areas [FIG. 2S (A-D)].

Figure 3S:
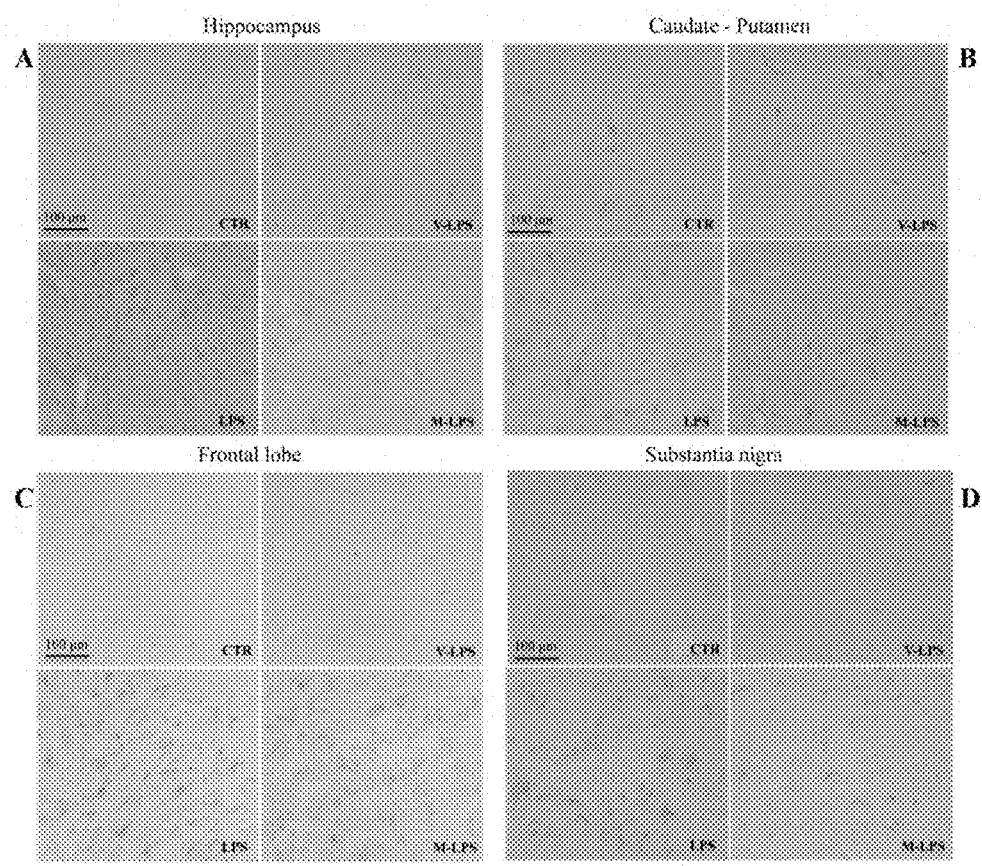
FIG. 3S. Iba-1 immunoreactivity in the hippocampus (A), caudate-putamen (B), frontal lobe (C) and substantia nigra (D), in slices of control (CTR), vehicle of LPS (v-LPS), LPS, mofezolac and LPS (M-LPS) treated mice.
Figure 4S:
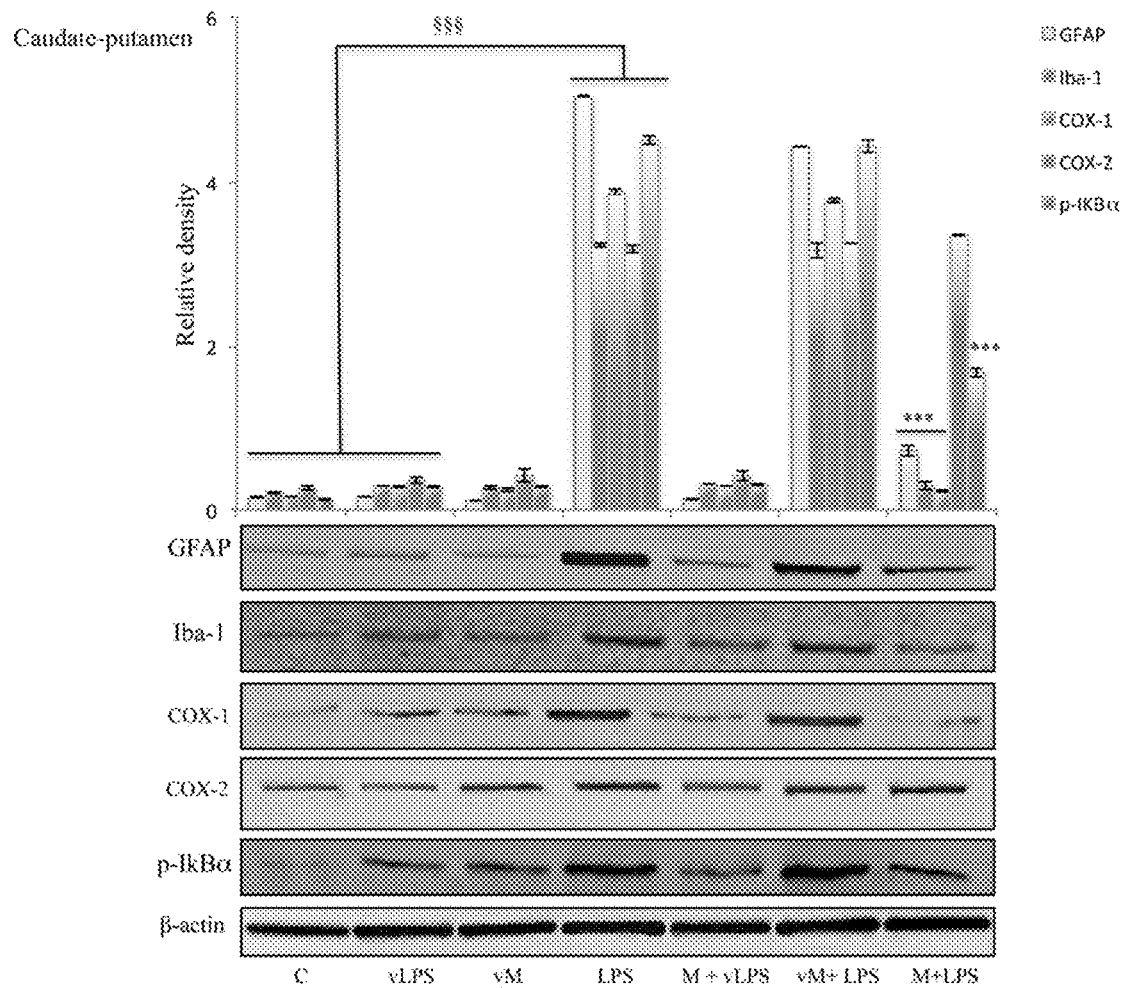
FIG. 4S. Effect of mofezolac on GFAP, Iba-1, COXs and pIkBα expression in caudate-putamen from mice treated with LPS alone and LPS in the presence of mofezolac. The quantification of relative band intensities was expressed as relative density, after normalization against β-actin densitometry. Values represents the means±SE of three independent experiments. C=control, vLPS=vehicle of LPS, vM=vehicle of mofezolac, M+vLPS=mofezolac and vehicle of LPS, vM+LPS=vehicle of mofezolac and LPS, M+LPS=mofezolac and LPS. § § § $p \le 0.001$ compared with control or vLPS; ***$p \le 0.001$ compared with LPS alone.
Figure 5S:
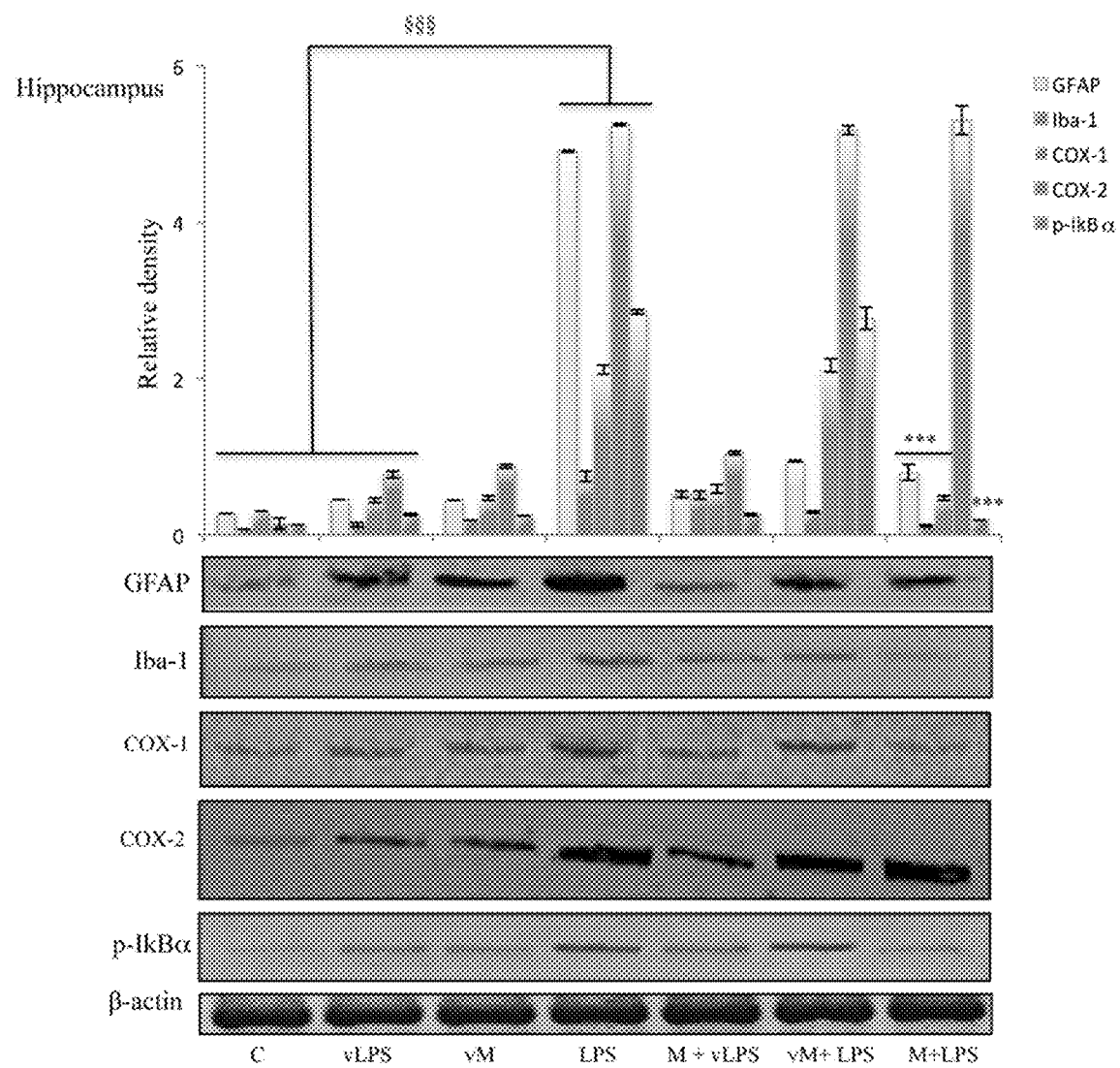
FIG. 5S. Effect of mofezolac on GFAP, Iba-1, COXs and pIkBα expression in hippocampus from mice treated with LPS alone and LPS in the presence of mofezolac. The quantification of relative band intensities was expressed as relative density, after normalization against β-actin densitometry. Values represents the means±SE of three independent experiments. C=control, vLPS=vehicle of LPS, vM=vehicle of mofezolac, M+vLPS=mofezolac and vehicle of LPS, vM+LPS=vehicle of mofezolac and LPS, M+LPS=mofezolac and LPS. § § § $p \le 0.001$ compared with control or vLPS; ***$p \le 0.001$ compared with LPS alone.
Figure 6S:
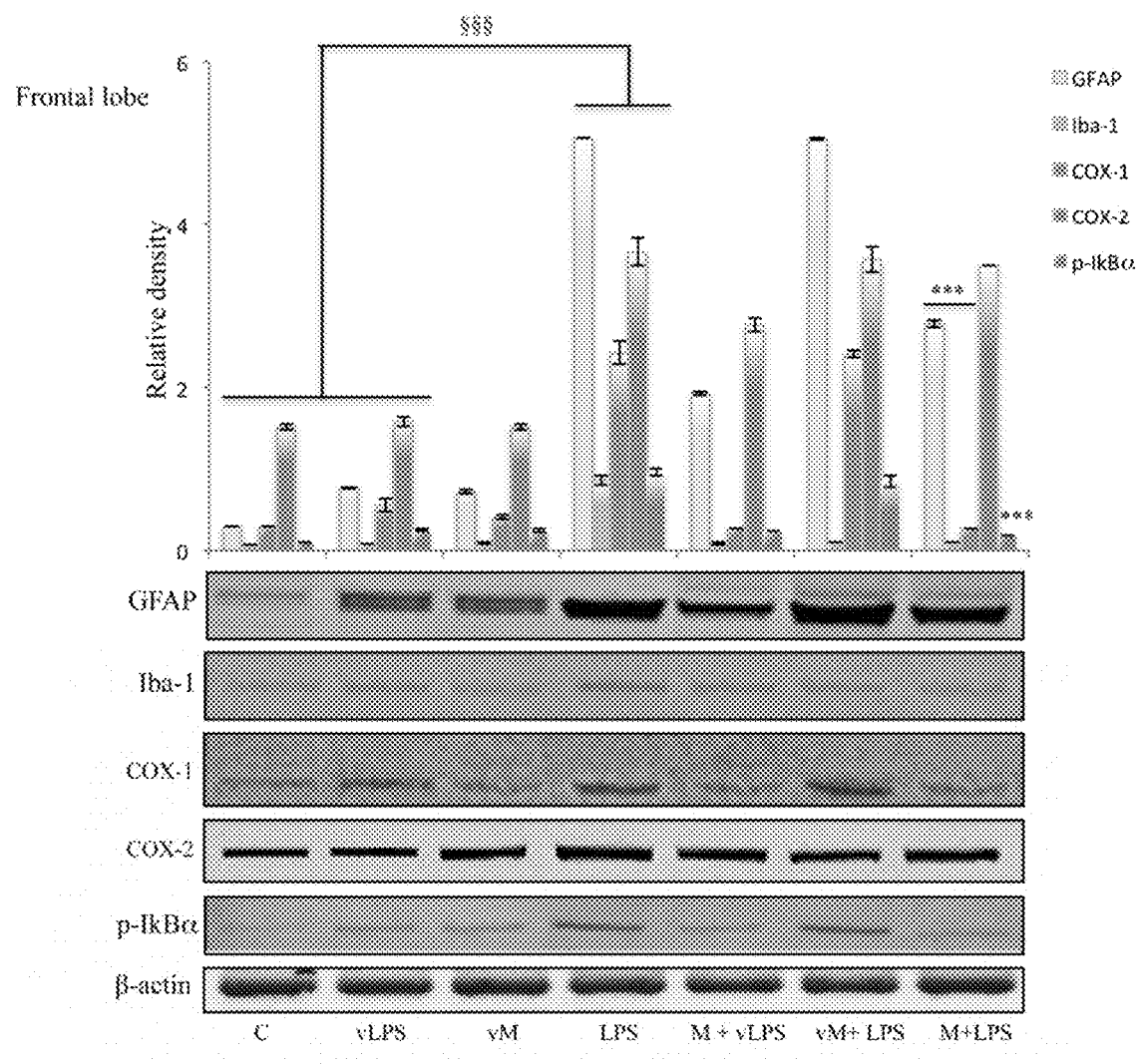
FIG. 6S. Effect of mofezolac on GFAP, Iba-1, COXs and pIkBα expression in frontal lobe from mice treated with LPS alone and LPS in the presence of mofezolac. The quantification of relative band intensities was expressed as relative density, after normalization against β-actin densitometry. Values represents the means±SE of three independent experiments. C=control, vLPS=vehicle of LPS, vM=vehicle of mofezolac, M+vLPS=mofezolac and vehicle of LPS, vM+LPS=vehicle of mofezolac and LPS, M+LPS=mofezolac and LPS. § § § $p \le 0.001$ compared with control or vLPS; ***$p \le 0.001$ compared with LPS alone.
Figure 7S:
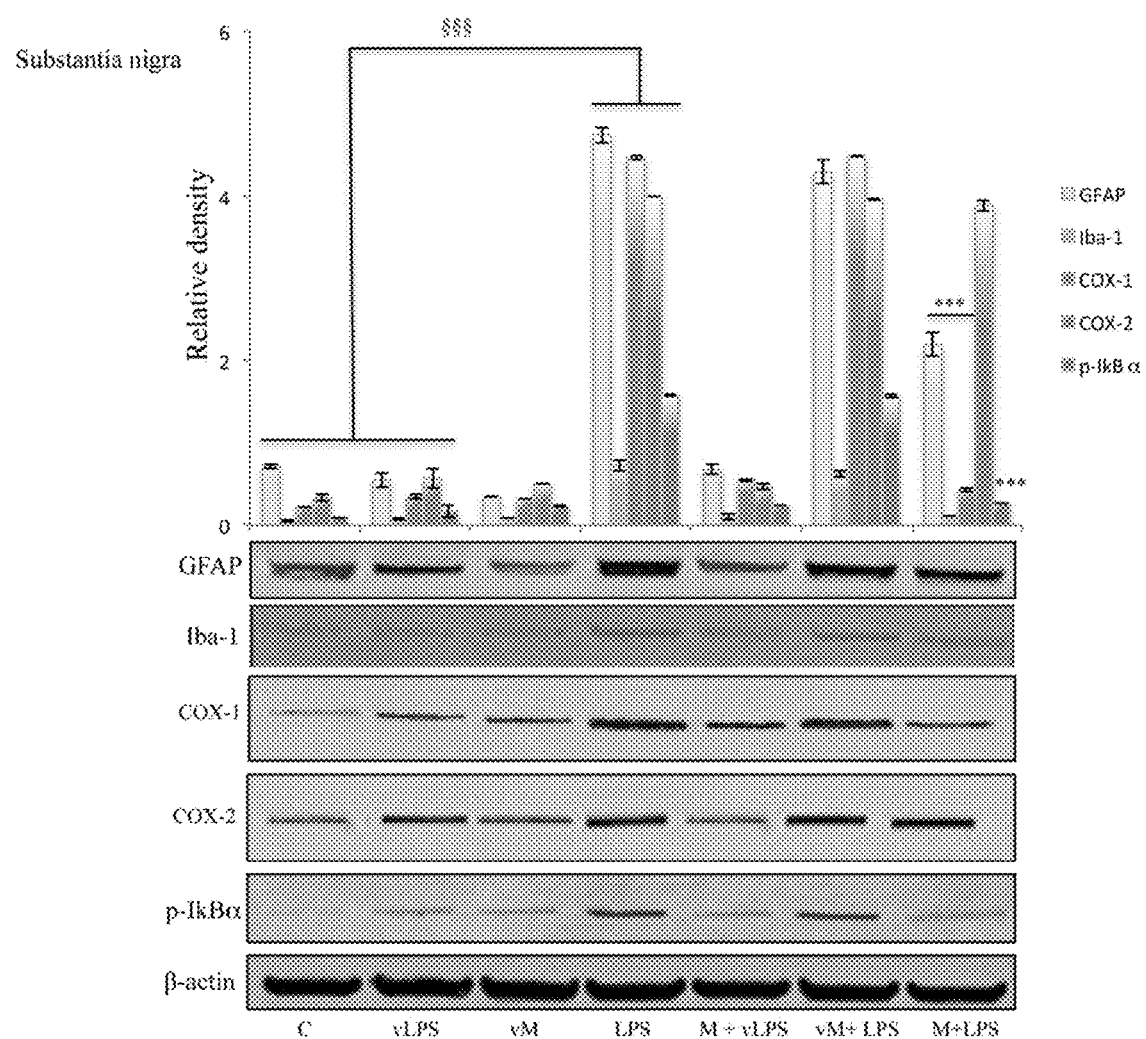
FIG. 7S. Effect of mofezolac on GFAP, Iba-1, COXs and pIkBα expression in substantia nigra from mice treated with LPS alone and LPS in the presence of mofezolac. The quantification of relative band intensities was expressed as relative density, after normalization against β-actin densitometry. Values represents the means±SE of three independent experiments. C=control, vLPS=vehicle of LPS, vM=vehicle of mofezolac, M+vLPS=mofezolac and vehicle of LPS, vM+LPS=vehicle of mofezolac and LPS, M+LPS=mofezolac and LPS. § § § $p \le 0.001$ compared with control or vLPS; ***$p \le 0.001$ compared with LPS alone.

Iba-1 immunoreactivity, a marker of activated microglia, was also evaluated [FIG. 3S]. LPS-treated mice Iba-1 positive cells were more numerous, showing a more intense immunoreactivity, as well as a ramified phenotype, in comparison to untreated mice [FIG. 3S (A-D)]. Mofezolac administration determined the reduction of Iba-1 immunoreactivity in LPS-injected mice in all the tested brain areas [FIG. 3S (A-D)], suggesting that mofezolac reduces, at least in part, the microglial activation induced by the neurotoxic insult.

Immunoblotting analysis was also performed to semi-quantitatively evaluate both astrocyte and microglia activation in samples derived from mice groups previously described. In LPS-treated mice a significant increase of GFAP expression was detected in all the brain regions tested when compared to controls or vehicle-LPS (FIGS. 4S-7S). Similar results were obtained for Iba-1 expression analysis (FIGS. 4S-7S). There is an evident increase of expression percentage for GFAP and Iba-1 in all the brain regions of mice treated with LPS compared to the control mice (Table 1).

TABLE 1

Increase percentage (%) of GFAP and Iba-1 expression and reduction percentage (%) of COX-1 and COX-2 expression, and PGE2 release by mofezolac in various brain regions of LPS-treated mice versus control.

| Brain region | GFAP expression increase (%) | Iba1 expression increase (%) | COX-1 expression reduction (%) | COX-2 expression reduction (%) | PGE$_2$ release reduction (%) |
|---|---|---|---|---|---|
| Caudate | 77 | 55 | 95 | 0 | 67 |
| Frontal lobe | 76 | 59 | 94 | 0 | 49 |
| Hippocampus | 56 | 79 | 82 | 0 | 48 |
| Substantia nigra | 38 | 68 | 89 | 0 | 39 |

Conversely, in mofezolac-treated animals previously injected with LPS the GFAP as well as Iba-1 levels resulted significantly reduced in comparison to the animals that received LPS alone (FIGS. 4S-7S).

Figure 8S:
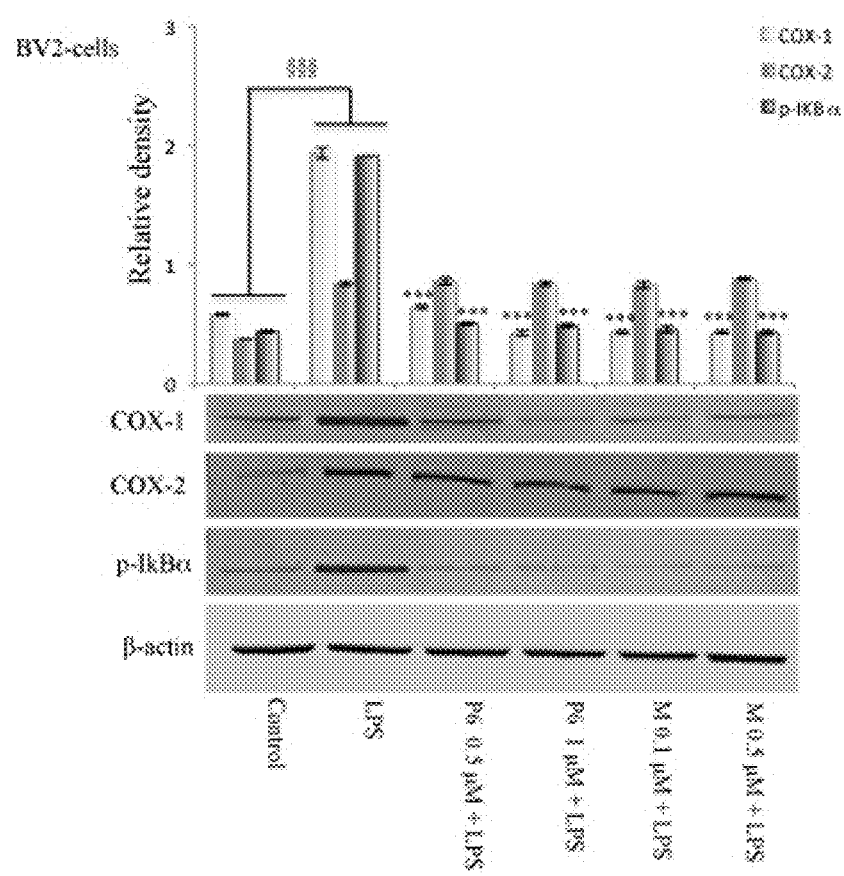
FIG. 8S. Effects of COX-1 inhibitors on the COXs expression and NF-kB phosphorylation induced by LPS in BV2 microglial cells. Total protein was subjected to SDS-PAGE, followed by immunoblotting using pIkBα antibody. The quantification of relative band intensities was expressed as relative density, after normalization against β-actin densitometry. Each bar represents the means±SE of three independent experiments. BV2 microglial cells incubated with medium alone (control) or treated with LPS alone or in presence of the P6 and mofezolac (M) for 48 h. § § § p 0.001 vs control, ***$p \le 0.001$ vs LPS alone.

Effect of the COX-1 inhibitors, P6 and mofezolac, on COXs expression in BV2 microglial cell line and mice brains The effect of mofezolac and P6 on COX-1 expression in LPS-treated microglial cells was evaluated by western blotting analysis. After 24 h, no significant difference between LPS-stimulated cells in the presence or absence of both COX-1 inhibitors was observed (data not shown). Interestingly, LPS-stimulated BV2 cells exhibited, at 48 h, increased levels of COX-1 expression in comparison to untreated cells (FIG. 8S). The COX-1 expression levels evaluated at 48 h of incubation with LPS was significantly reduced in 1 h pre-treated cells with either selective COX-1 inhibitors P6 or mofezolac (FIG. 8S). Therefore, COX-1 expression was found to be time-dependently reduced by both selective inhibitors tested (Table 1).

The expression of COX-2 in the same cell lysates was also evaluated. Interestingly, COX-2 protein levels were unaffected by the presence of P6 or mofezolac. In these conditions, COX-2 expression resulted comparable to the level observed in cells stimulated with LPS alone (FIG. 8S).

Therefore, in LPS-treated BV2 microglial cell line P6 and mofezolac were able to reduce COX-1 expression without affecting COX-2. In fact, P6 administration in LPS-activated cells reduced COX-1 expression of 67% and 79% at the 0.5 μM and 1.0 μM, respectively. Moreover, mofezolac reduced COX-1 expression (78%) independently from its concentration (Table 1).

COXs expression was also in vivo evaluated, assaying different brain regions (FIG. 4S-7S). LPS-challenged mice exhibited increased levels of COX-1 both in comparison to controls and vehicle-LPS (vLPS) administered animals in all the different areas tested (FIG. 4S-7S). Interestingly, LPS challenged mice that received mofezolac treatment exhibited a significantly reduction of COX-1 expression in all brain areas tested, where reduction percentage ranged from 82 to 95% (Table 1). Protein levels comparable to controls were detected in mice treated with vehicle of LPS+mofezolac, whereas in mice treated with the vehicle of mofezolac+LPS, COX-1 levels resulted comparable to those detected in LPS-treated mice (FIGS. 4S-7S).

Immunoblotting assay on tissues of the same brain areas was performed to test the in vivo effects of mofezolac administration on COX-2 expression extent. COX-2 resulted overexpressed in all tested brain regions in LPS-administrated mice. Interestingly, mofezolac exhibited no effect on COX-2 modulation in LPS-treated mice, being the protein levels almost comparable to LPS-treated mice (FIG. 4S-7S).

Effect of COX-1 Inhibitors on PGE2 Bio-Synthesis in BV2 Microglial Cells and Mouse Brain The PGE2 bio-synthesis extent was evaluated in supernatants of cell cultures at 48 h incubation time (Table 2A). PGE2 production in LPS-stimulated cells was significantly higher than its basal level present in the untreated cells (control). Interestingly, both COX-1 inhibitors were able to reduce in a dose-dependent manner PGE2 release in LPS-treated cells (Table 2A).

A) Effect of COX-1 inhibitors P6 and mofezolac (M) on PGE$_2$ release (ng/ml) at 48 h in LPS-stimulated BV2 microlial cells.

| Control | LPS | 0.5 μM P6 + LPS | 1 μM P6 + LPS | 0.1 μM M + LPS | 0.5 μM M + LPS |
|---|---|---|---|---|---|
| 0.22 ± 0.0.25 | 0.97 ± 0.021 [a] | 0.21 ± 0.010 [b] | 0.12 ± 0.008 [b] | 0.06 ± 0.004 [b] | 0.03 ± 0.002 [b] |

B) Effect of mofezolac (M) on PGE$_2$ release (ng/mg tissue) in specimens from LPS-treated mice.

| Specimen | Control | Vehicle LPS | LPS | M+LPS |
|---|---|---|---|---|
| Caudate-Putamen | 0.15 ± 0.050 | 0.73 ± 0.045 [c] | 5.61 + 0.136 [c] | 1.84 + 0.035 [d] |

In particular, P6 determined a reduction of 78 and 88% at 0.5 and 1 μM, respectively, whereas in the presence of mofezolac the PGE2 production reduced of 94 and 97% at 0.5 and 1 μM, respectively.

In the tested brain regions of LPS-treated mice, PGE2 levels were significantly increased with respect to control animals or mice receiving the vehicle of LPS (Table 2B). Interestingly, a significant reduction of PGE2 levels was detected in mofezolac treated mice before LPS challenging (Table 2B). PGE2 reduction by mofezolac in brain tissues of LPS-treated mice ranged from 39% to 67% (Table 1).

TABLE 2

In vitro and in vivo PGE2 release affected by COX-1 inhibitors P6 and Mofezolac (M).

| | | | | |
|---|---|---|---|---|
| Hippocampus | 0.31 ± 0.036 | 0.69 ± 0.032 [c] | 4.55 ± 0.046 [c] | 2.33 ± 0.032 [d] |
| Frontal lobe | 0.33 ± 0.026 | 0.68 ± 0.026 [c] | 4.60 ± 0.055 [c] | 2.40 ± 0.046 [d] |
| Substantia nigra | 0.42 ± 0.021 | 0.74 ± 0.059 [c] | 5.48 ± 0.115 [c] | 3.31 ± 0.079 [d] |

[a] $p \leq 0.01$ compared with the control value;
[b] $p \leq 0.01$ vs LPS alone;
[c] $p \leq 0.001$ vs untreated animals (control);
[d] $p \leq 0.01$ vs LPS-treated animals.

Effect of COX-1 Inhibitors on NF-kB Activation in LPS-Treated BV2 Microglial Cells and Mouse Brain Since the phosphorylation and degradation of IkBα, the inhibitory complex of NF-kB, is an essential step for NF-kB activation, the expression levels of the phosphorylated form of IkBα (p-IkBα were evaluated (FIG. 8). In this context, BV2 microglial cells exposed to LPS exhibited a significant increase of p-IkBα in comparison with no stimulated cells (control) (FIG. 8). Densitometric analysis revealed little p-IkBα in the untreated cells, whereas pre-treatment with all tested COX-1 inhibitors, significantly reduced IkBα phosphorylation in LPS-stimulated cells (FIG. 8).

Similar results were obtained in in vivo model. In fact, in all tested brain areas of LPS-treated mice an increase of p-IkBα in comparison to control animals as well as to vehicle of LPS (vLPS) administered mice, was detected. Conversely, in mice receiving mofezolac (M), a significant reduction of p-IkBα in all tested areas was detected (FIGS. 4-7).

p-IkBα levels comparable to controls were detected in mice treated with vehicle of LPS+mofezolac, whereas in mice treated with vehicle of mofezolac+LPS, p-IkBα levels were comparable to those detected in LPS-treated mice (FIGS. 4-7).

Conclusions

These results demonstrated that both P6 and mofezolac were able to reduce COX-1 derived PGE2 release down-regulating NF-kB activation pathway, thus providing mechanistic insights into the suppressive effect of these COX-1 inhibitors on LPS-induced neuroinflammatory response by microglia.

In conclusion, this work consolidated the hypothesis that selective COX-1 inhibitors can positively modify the inflammatory response in LPS-induced neuroinflammatory models. Overall these results, from in vitro and in vivo experiments, indicate the capability of two highly selective COX-1 inhibitors P6 and mofezolac to modulate the NF-kB signaling pathway. These findings emphasize the neuroprotective effect and therapeutic potential of COX-1 inhibitors such as P6 and mofezolac useful in the control of neuroinflammatory diseases.

The invention claimed is:

1. A compound having formula I

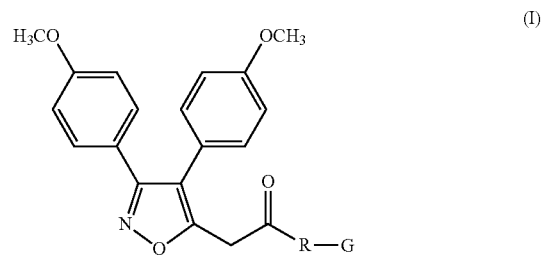

wherein R is a linker selected from benzidine, phenylenediamine, α,α'-diamino-p-xylenealkyldiamine, O—(CH2)n, NH—(CH2)nCO, NH—(CH2)n or NH—(CH2)nNH, wherein n is from 0 to 12, and wherein G is a fluorescent moiety selected from nile blue and analogues thereof.

2. The compound according to claim 1 wherein R is NH—$(CH_2)_n$NH, and wherein n is 2, 4, 6 or 12.

3. The compound according to claim 1, having a formula:

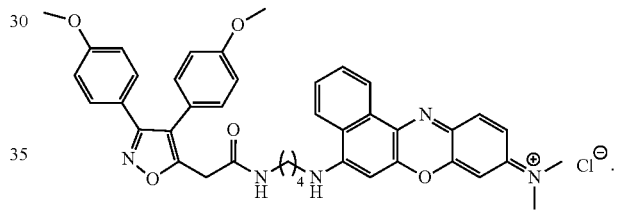

4. The compound according to claim 1, wherein the compound is isotopically radiolabeled with an isotope.

5. An in vivo or ex vivo method of imaging cancer comprising administering the compound according to claim 1 to a subject in need thereof.

6. A diagnostic imaging composition comprising the compound according to claim 1 as an imaging agent and a carrier.

7. An in vivo or ex vivo method of diagnosing cancer comprising administering the diagnostic imaging composition according to claim 6, to a subject in need thereof.

8. An in vitro method of diagnosing cancer comprising contacting an effective amount of the compound according to claim 1 with a sample of cells.

9. The in vitro method according to claim 8, further comprising a step of fluorescence analysis of said sample of cells.

10. The compound according to claim 4, wherein the isotope is selected from $^{3}H$, $^{11}C$, $^{14}C$, $^{13}N$, $^{15}O$, and $^{18}F$.

11. The in vivo or ex vivo method according to claim 5, wherein the cancer is ovarian cancer.

12. The in vivo or ex vivo method according to claim 7, wherein the cancer is ovarian cancer.

* * * * *